(12) United States Patent
Tang et al.

(10) Patent No.: US 6,706,709 B2
(45) Date of Patent: Mar. 16, 2004

(54) INDOLINONE DERIVATIVES AS PROTEIN KINASE/PHOSPHATASE INHIBITORS

(75) Inventors: Peng Cho Tang, Moraga, CA (US); G. Davis Harris, San Francisco, CA (US); Xiaoyuan Li, Los Altos, CA (US)

(73) Assignee: Sugen, Inc., South San Francisco, CA (US)

(*) Notice: Subject to any disclaimer, the term of this patent is extended or adjusted under 35 U.S.C. 154(b) by 34 days.

(21) Appl. No.: 09/871,700

(22) Filed: Jun. 4, 2001

(65) Prior Publication Data

US 2002/0052369 A1 May 2, 2002

Related U.S. Application Data

(60) Provisional application No. 60/209,162, filed on Jun. 2, 2000.

(51) Int. Cl.$^7$ .................. A61F 31/5377; C07D 413/14
(52) U.S. Cl. .................. 514/235.2; 544/143; 544/144; 548/455
(58) Field of Search ............... 514/235.2, 412; 544/143, 144; 548/455

(56) References Cited

U.S. PATENT DOCUMENTS

| | | |
|---|---|---|
| 2,968,557 A | 1/1961 | Burgandt et al. |
| 4,002,749 A | 1/1977 | Rovnyak |
| 4,053,613 A | 10/1977 | Rovnyak et al. |
| 4,642,309 A | 2/1987 | Michel et al. |
| 4,826,847 A | 5/1989 | Michel et al. |
| 5,051,417 A | 9/1991 | Nadler et al. |
| 5,124,347 A | 6/1992 | Connor et al. |
| 5,196,446 A | 3/1993 | Levitzki et al. |
| 5,302,606 A | 4/1994 | Spada et al. |
| 5,322,950 A | 6/1994 | Sircar et al. |
| 5,374,652 A | 12/1994 | Buzzetti et al. |
| 5,382,593 A | 1/1995 | Le Baut et al. |
| 5,389,661 A | 2/1995 | Sircar et al. |
| 5,397,787 A | 3/1995 | Buzzetti et al. |
| 5,409,949 A | 4/1995 | Buzzetti et al. |
| 5,792,783 A | 8/1998 | Tang et al. |
| 5,834,504 A | 11/1998 | Tang et al. |
| 5,849,710 A | 12/1998 | Battistini et al. |
| 5,880,141 A | 3/1999 | Tang et al. |
| 5,883,113 A | 3/1999 | Tang et al. |
| 5,883,116 A | 3/1999 | Tang et al. |
| 5,886,020 A | 3/1999 | Tang et al. |
| 6,133,305 A | 10/2000 | Tang et al. |

FOREIGN PATENT DOCUMENTS

| | | |
|---|---|---|
| AU | 286870 | 5/1967 |
| CA | 2012634 | 9/1991 |
| DE | 2159360 | 11/1971 |
| DE | 2159361 | 11/1971 |
| DE | 2159362 | 11/1971 |
| DE | 2159363 | 11/1971 |
| DE | 2321656 | 4/1973 |
| DE | 3426419 | 1/1986 |
| EP | 0351213 | 1/1990 |
| EP | 0252713 | 9/1990 |
| EP | 0525472 | 2/1993 |
| EP | 0632102 | 1/1995 |
| EP | 0662473 | 7/1995 |
| EP | 0769947 | 5/1997 |
| EP | 0788890 | 8/1997 |
| EP | 0934931 | 8/1999 |
| EP | 1082305 A1 | 3/2001 |
| FR | 1398224 | 3/1965 |
| FR | 1599772 | 8/1970 |
| FR | 2689397 | 10/1993 |
| GB | 809691 | 3/1959 |
| GB | 835473 | 5/1960 |
| JP | 6239564 | 2/1987 |
| JP | 6229570 | 7/1987 |
| JP | 63141955 | 6/1988 |
| JP | 558894 | 3/1993 |
| WO | 91/13055 | 9/1991 |
| WO | 92/07830 | 5/1992 |
| WO | 92/20642 | 11/1992 |
| WO | 93/01182 | 1/1993 |
| WO | 94/14808 | 7/1994 |
| WO | 95/01349 | 1/1995 |
| WO | 95/17181 | 6/1995 |
| WO | 96/22976 | 8/1995 |
| WO | 96/00226 | 1/1996 |
| WO | 96/16964 | 6/1996 |
| WO | 96/32380 | 10/1996 |
| WO | 96/40116 | 12/1996 |
| WO | 97/25986 | 7/1997 |
| WO | 98/07695 | 2/1998 |
| WO | 98/24432 | 6/1998 |
| WO | 98/38984 | 9/1998 |
| WO | 98/50356 | 11/1998 |
| WO | WO98/50356 A | 11/1998 |
| WO | 99/10325 | 3/1999 |
| WO | 99/52869 | 10/1999 |
| WO | 99/61422 | 12/1999 |
| WO | 99/65869 | 12/1999 |

(List continued on next page.)

OTHER PUBLICATIONS

Andreani et al., "Potential Antitumor Agents. 25[1]. Synthesis and Cytotoxic Activity of 3–(2–Chloro–3–Indolymethylene)1, 3–Dihydroindol–2–Ones," *Anticancer Research* 16:3585–3588 (1996) © Elsevier, Paris.

(List continued on next page.)

*Primary Examiner*—Alan L. Rotman
*Assistant Examiner*—Kamal Saeed
(74) *Attorney, Agent, or Firm*—Beth A. Burrous; Foley & Lardner

(57) ABSTRACT

The present invention relates to certain 2-indolinone compounds which modulate the activity of protein kinases ("PKs") and phosphatases. The compounds of this invention are therefore useful in treating disorders related to abnormal PK activity. Pharmaceutical compositions comprising these compounds, methods of treating diseases utilizing pharmaceutical compositions comprising these compounds and methods of preparing them are also disclosed.

8 Claims, No Drawings

FOREIGN PATENT DOCUMENTS

| WO | 00/08202 | 2/2000 |
|---|---|---|
| WO | WO00/08202 A | 2/2000 |
| WO | 00/35906 | 6/2000 |
| WO | 00/35908 | 6/2000 |
| WO | 00/35909 | 6/2000 |
| WO | 00/38519 | 7/2000 |
| WO | WO00/56709 A | 9/2000 |
| WO | 00/56709 | 9/2000 |
| WO | 01/60814 | 8/2001 |
| WO | WO02/02551 A | 1/2002 |
| WO | 02/02551 A1 | 1/2002 |

OTHER PUBLICATIONS

Andreani et al., "Synthesis and cardiotonic activity of 2–indolinones," *Eur. J. Med. Chem.* 25:187–190 (1990).

Andreani et al., "Synthesis and cardiotonic activity of 2–indolinones bearing pyridyl groups," *Eur. J. Med. Chem.* 28:653–657 (1993) © Elsevier, Paris.

Andreani et al., "Synthesis and cardiotonic activity of pyridylmethylene–2–indolinones," *Eur. J. Med. Chem.* 27:167–170 (1992) © Elsevier, Paris.

Andreani et al., "Synthesis and potential coanthracyclinic activity of substituted 3–(5–imidazo[2,1–b]thiazolylmethylene)–2–indolinones," *Eur. J. Med. Chem.* 32:919–924 (1997)© Elsevier, Paris.

Andreani et al., "Synthesis of lactams with potential cardiotonic activity," *Eur. J. Med. Chem.* 28:825–829 (1993).

Andreani et al., "In Vivo Cardiotonic Activity of Pyridylmethylene–2–indolinones," *Arzneimittel–Forschung Drug Research* 48:727–729 (1998)©.

Bahner and Brotherton, "9–(4–Aminobenzylidene)fluorenes," *J. Med. Chem.* 12:722–723 (1969).

Bahner et al., "Benzylideneindenes with Oxygen Attached to the Indene Ring," *J. Med. Chem.* 12:721–722 (1969).

Bamfield et al., "Diels–Alder Reactions of Oxindolylideneacetone," *J. Chem. Soc. (C)* 1028–1030 (1966) ©.

Borsche et al., "Ober vielkernige kondensierte Systeme mit heterocyclischen Ringen. XIII.," *Liebigs Ann. Chem.* 550:160–174 (1941).

Buzzetti et al., "Cinnamamide Analogs as Inhibitors of Protein Tyrosine Kinases," *Il Farmaco* 48:615–636 (1993).

Chatten et al., "Substituted Oxindoles. Part VI. Polarographic Reduction of Substituted trans–3–Benzylideneindol–2(3H)–ones," *J. Ch m. Soc. Perkin II:* 469–473 (1973).

Coda et al., "(Z)– and (E)–Arylidene–1, 3–dihydroindol–2–ones: Configuration, Conformation and Infrared Carbonyl Stretching Frequ ncies," *J. Chem. Soc. Perkin Trans. II:* 615–619 (1984).

Coda et al., "3–(4–methylbenzilidene)–1, 3–dihydroindol–2–one," *Journal of the Chemical Society, Perkin Transactions 2* 4:615–620 (1984) Database Crossfire, Beilstein Reference No. 6–21.

Decodts et al., "Suicide inhibitors of proteases. Lack of activity of halomethyl derivatives of some aromatic lactams," *Eur. J. Med. Chem* 18: 107–111 (1983).

Desimoni et al., "Catalysis with Inorganic Cations. V$^1$ Intramolecular Hetero Diels–Alder versus Ene Reactions: Effect of Magnesium perchlorate on Chemoselectivity," *Tetrahedron* 52(36) 12009–12018 (1196) © Pergamon.

Elliott and Rivers, "Reduction of Some Oxindolylidene Derivatives to 3–Substituted Oxindoles by Sodium Borohydride," *J. Med. Chem.* 29:2438–2440 (1964).

Elliott et al., "1–methyl–2–(3–oxindolidenmethyl)–pyridinium," *Journal of Organic Chemistry* 29:2438–2440 (1964) Database Crossfire, Beilstein Reference No. 5–24.

Gazit et al., "Tyrphostins. 2. Heterocyclic and α–Substituted Benzylidenemalononitrile Tyrphostins as Potent Inhibitors of EGF Receptor and ErbB2/neu Tyrosine Kinases," *J. Med. Chem.* 34:1896–1907 (1991) copyright Am. Clem. Soc.

Hirao et al., "Rhodium–Catalyzed Carbonylation of 2–Alkynylaniline: Syntheses of 1,3–Dihydroindol–2–ones," *Tetrahedron Letters* 36(35) 1995 ©Pergamon.

Hodges et al., "Chemical and biological properties of some oxindolidyl–3–methines," *Canadian J. Chemistry* 46:2189–2194 (1968).

Howard, Harry R., "Lactam Derivatives," U.S. Provisional Patent Application No. 60/015134.

Howard et al., "Synthesis and aldose reductase inhibitory activity of substituted 2(1H)–benzimidazolone– and oxindole–1–acetic acids," *Eur. J. Med. Chem.* 27:779–789 (1992) © Elsevier, Paris.

Katritzky et al., "Color and Constitution. Part 8[1]. Some Novel Dyestuffs Containing Indoxyl Residues," *J. Heterocyclic Chem.* 25:1287–1292 (1988).

Kobayashi et al., "Anti–tumor Activity of Indole Derivatives," *Yakugaku Zasshi* 97:1033–1039 (1977).

Kovac and Stetinova, "Furan derivatives. LXXX. Synthesis and properties of substituted furfurylidenoxindoles," *Chem. rvesu* 30:484–492 (1976).

Levitzki and Gazit, "Tyrosine Kinase Inhibition: An Approach to Drug Development," *Science* 267:1782–1788 (1995).

Mariani et al., "Inhibition of angiogenesis by FCE 26806, a potent tyrosine kinase inhibitor," *Experimental Therapeutics—Proceedings of the American Association for Cancer Research* 35:381 at abstract No. 2268 (Mar. 1994).

Mohammadi et al., "Structures of the Tyrosine Kinase Domain of Fibroblast Growth Factor Receptor in Complex with Inhibitors," *Science* 276:955–960 (1997) © American Association for the Advancement of Science.

Neber and Röcker, "On the action of benzaldehydes on the free o–aminophenylacetic acid (II)," *Chem. Ber.* 56:1710–1716 (1923) (German and English Translation).

Nodiff et al., "Antimalarial Phenanthrene Amino Alcohols. 3. Halogen–containing 9–phenanthrenemethanols," *Chemical Abstracts,* vol. 83, abstract No. 188214 (1975).

O'Sullivan and Rothery, "The Preparation and Possible Clinical Significance of 4'–Dialkylaminoisoindogenides," *Clinica Chimica Acta* 62:181–182 (1975) ©Elsevier Scientific Publishing Company.

Pavlenko et al., "Introduction of aminomethyl groups into heterocyclic CH–acid molecules," *Dopov. Akad. Nauk Ukr Rsrs, Ser. B; Geol., Khim. Biol. Naukl* 7:64–66 (1980) We should add thqat we are Sub. Abstract.

Plowman et al., "Receptor Tyrosine Kinases as Targets for Drug Intervention," *DN&P* 7:334–339 (1994).

Quallich et al., A General Oxindole Synthesis, *J. Synthetic Organic Chemistry:* 51—51 (1993).

Schuchter et al., "Successful Treatment of Murine Melanoma with Bryostatin 1," *Cancer Research* 51:682–687 (1991).

Shiraishi et al., "Specific Inhibitors of Tyrosine–Specific Protein Kinase, Synthetic 4–Hydroxycinnamamide Derivatives," *Biochemical and Biophysical Research Communications* 147:322–328 (1987)© Academic Press.

Shiraishi et al., "Specific Inhibitors of Tyrosine–specific Protein Kinases: Properties of 4–Hydroxycinnamamide Derivatives in Vitro," *Cancer Research* 49:2374–2378 (1989).

Singh et al., "Indolinone Derivatives as Potential Antimicrobial Agents," *Zentralbl, Mikrobiol.* 144:105–109 (1989) copyright VEB Gustav Fischer Verlag Jena.

Spada, et al., "Small molecule inhibitors of tyrosine kinase activity," *Expert Opinion on Therapeutic Patents* 5:805–817 (1995) ©Ashley Publications.

Sun et al., "Design, Synthesis, and Evaluations of Substituted 3–[(3– or 4–Carboxyethylpyrrol–2–yl) methylidenyl] indolin–2–ones as Inhibitors of VEGF, FGF, and PDGF Receptor Tyrosine Kinases," *Journal of Medicinal Chemistry* 42: 5120–5130 (1999) ©American Chemical Society.

Sun et al, "Synthesis and Biological Evaluations of 3–Substituted Indolin–2–ones: A Novel Class of Tyrosine Kinase Inhibitors That Exhibit Selectivity toward Particular Receptor Tyrosine Kinases," *J. Med. Chem.* 41:2588–2603 (1998) ©The American Chemical Society.

Tacconi and Marinone, "Preparazione e caratteristiche di alcuni 3–ossindolidenderivati," *Ricerca Scientifica* 38:1239–1244 (1968).

Tacconi et al., "(Z)– and (E)–3–Alkylidene–1, 3–dihydroindol–2–ones: Influence of Configuration on the Transmission of the Inductive Effect to the Carbonyl Group," *J.C.S. Perkin II* 150–154 (1976).

Thompson et al., "Facile Dimerisation of 3–Benzylideneindoline–2–thiones," *J. Chem. Soc. Perkin Trans.* (*I*) 1835–1837 (1993).

Traxler, "Protein tyrosine kinase inhibitors in cancer treatment," *Expert Opinion on Therapeutic Patents* 7(6):571–588 (1997) © Ashley Publications Ltd.

Wahl et al., "3–benzilidene–5–m thyl–1, 3–dihydroindol–2–one," *Ann. Chim.* 350 (1926), Database Crossfire, Beilstein Reference No. 2–21–00–00290.

Wahl, Beilst in Reg. No. 191439, *Bull. Soc. Chim. Fr.,* p. 1038 (1909).

Wahl, Beilstein Reg. No. 231732, *Bull. Soc. Chim. Fr.,* pp. 1035–1038 (1909).

Walker et al., "Synthesis of New 3–(Pyridylmethylene)–, 3–(Pyridylmethyl)–, 3–(Piperidylmethyl)–, and 3–(β–Alkylaminoethyl)–2–Indolinones. The Reduction of Isoindogenides, Nitro Compounds, and Pyridines in a Series of 2–Indolinones," *J. Med. Chem.* 8:626–637 (1965).

Wright et al., "Cyclic Hydroxamic Acids Derived from Indole," *J. Am. Chem. Soc.* 78:221–224 (1956).

Wright et al., "Inhibition of Angiogenesis in Vitro and in Ovo With an Inhibitor of Cellular Protein Kinases, MDL 27032," *J. Cellular Physiology* 152:448–457 (1992).

Zhang et al., "Microtubule Effects of Welwistatin, a Cyanobacterial Indolinone that Circumvents Multiple Drug Resistance," *Molecular Pharmacology* 49:228–234 (1996) copyright The American Society for Pharmacology and Experimental Pharmaceutics.

Zhungietu et al., "Reaction of Indoles and 2–Ketoindolines With Some Aldehydes," *Chemical Abstracts,* vol. 78, abstract No. 111201 (1990).

English Translation of Hungarian Patent No. 3899/92.

XP–002190338 (Dobeneck, et al., *Chem. Ber.* 102: 1347–1356 (1969)).

von Dobeneck, H. et al., "α–β'–Diindolylmethane und –methene. Der Urorosein–Chromophor," *Chemische Berichte,* 102(4):1347–1356 (1969).

INDOLINONE DERIVATIVES AS PROTEIN KINASE/PHOSPHATASE INHIBITORS

CROSS-REFERENCE

This application claims priority under 35 U.S.C. 119(e) to U.S. Provisional Applications Ser. No. 60/209,162, filed Jun. 2, 2000, the disclosure of which is incorporated herein by reference in its entirety.

BACKGROUND OF THE INVENTION

1. Field of Invention

The present invention relates to certain 2-indolinone compounds which modulate the activity of protein kinases ("PKs") and phosphatases. The compounds of this invention are therefore useful in treating disorders related to abnormal PK activity. Pharmaceutical compositions comprising these compounds, methods of treating diseases utilizing pharmaceutical compositions comprising these compounds and methods of preparing them are also disclosed.

2. State of the Art

Cellular signal transduction is a fundamental mechanism whereby extracellular stimuli are relayed to the interior of cells and subsequently regulate diverse cellular processes. One of the key biochemical mechanisms of signal transduction involves the reversible phosphorylation of proteins. Phosphorylation of polypeptides regulates the activity of mature proteins by altering their structure and function. Phosphate most often resides on the hydroxyl moiety (—OH) of serine, threonine, or tyrosine amino acids in proteins.

Enzymes that mediate phosphorylation of cellular effectors generally fall into two classes. The first class consists of protein kinases which transfer a phosphate moiety from adenosine triphosphate to protein substrates. The second class consists of protein phosphatases which hydrolyze phosphate moieties from phosphoryl protein substrates. The converse functions of protein kinases and protein phosphatases balance and regulate the flow of signals in signal transduction processes.

Protein kinases and protein phosphatases are generally divided into two groups—receptor and non-receptor type proteins. Most receptor-type protein tyrosine phosphatases contain two conserved catalytic domains, each of which encompasses a segment of 240 amino acid residues. Saito et al., 1991, *Cell Growth and Diff.* 2:59–65. Receptor protein tyrosine phosphatases can be subclassified further based upon the amino acid sequence diversity of their extracellular domains. Saito et al, supra; Krueger et al., 1992, *Proc. Natl. Acad. Sci. USA* 89:7417–7421.

Protein kinases and protein phosphatases are also typically divided into three classes based upon the amino acids they act upon. Some catalyze the addition or hydrolysis of phosphate on serine or threonine only, some catalyze the addition or hydrolysis of phosphate on tyrosine only, and some catalyze the addition or hydrolysis of phosphate on serine, threonine, and tyrosine.

Tyrosine kinases can regulate the catalytic activity of other protein kinases involved in cell proliferation. Protein kinases with inappropriate activity are also involved in some types of cancer. Abnormally elevated levels of cell proliferation are associated with receptor and non-receptor protein kinases with unregulated activity.

In addition to their role in cellular proliferation, protein kinases are thought to be involved in cellular differentiation processes. Cell differentiation occurs in some cells upon nerve growth factor (NGF) or epidermal growth factor (EGF) stimulation. Cellular differentiation is characterized by rapid membrane ruffling, cell flattening, and increases in cell adhesion. Chao, 1992, *Cell* 68:995–997.

In an effort to discover novel treatments for cancer and other diseases, biomedical researchers and chemists have designed, synthesized, and tested molecules that inhibit the function of protein kinases. Some small organic molecules form a class of compounds that modulate the function of protein kinases. Examples of molecules that have been reported to inhibit the function of protein kinases are bis-monocyclic, bicyclic or heterocyclic aryl compounds (PCT WO 92/20642), vinylene-azaindole derivatives (PCT WO 94/14808), 1-cyclopropyl-4-pyridyl-quinolones (U.S. Pat. No. 5,330,992), styryl compounds (by Levitzki, et al., U.S. Pat. No. 5,217,999, and entitled "Styryl Compounds which Inhibit EGF Receptor Protein Tyrosine Kinase), styryl-substituted pyridyl compounds (U.S. Pat. No. 5,302,606), certain quinazoline derivatives (EP Application No. 0 566 266 A1), seleoindoles and selenides (PCT WO 94/03427), tricyclic polyhydroxylic compounds (PCT WO 92/21660), and benzylphosphonic acid compounds (PCT WO 91/15495).

The compounds that can traverse cell membranes and are resistant to acid hydrolysis are potentially advantageous therapeutics as they can become highly bioavailable after being administered orally to patients. However, many of these protein kinase inhibitors only weakly inhibit the function of protein kinases. In addition, many inhibit a variety of protein kinases and will therefore cause multiple side-effects as therapeutics for diseases.

Despite the significant progress that has been made in developing compounds for the treatment of cancer, there remains a need in the art to identify the particular structures and substitution patterns that form the compounds capable of modulating the function of particular protein kinases.

SUMMARY OF THE INVENTION

In a first aspect, the invention provides an indolinone compound having a structure set forth in formula (I):

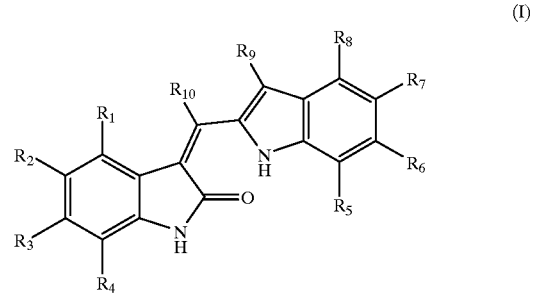

(I)

wherein:
(a) $R_4$–$R_6$, and $R_8$–$R_{10}$ are hydrogen;
(b) $R_1$, $R_2$, and $R_3$ are each independently selected from the group consisting of hydrogen, halogen, carboxylic acid, optionally substituted ester, optionally substituted amide, optionally substituted alkyl, optionally substituted alkoxy, trihalomethyl, optionally substituted aryl, and optionally substituted heteroaryl; and
(c) $R_7$ is selected from the group consisting of substituted alkyl, and substituted alkoxy;
or a pharmaceutically acceptable salt thereof.

Preferably, (a) $R_1$ is selected from the group consisting of hydrogen and optionally substituted alkyl, more preferably hydrogen;

(b) $R_2$ and $R_3$ are each independently selected from the group consisting of hydrogen, halo, carboxylic acid, optionally substituted heteroaryl, and optionally substituted phenyl. Preferably $R_2$ is hydrogen, halo, phenyl, or carboxylic acid, more preferably hydrogen, phenyl, —COOH, chloro, fluoro or bromo. Preferably, $R_3$ is hydrogen, halo, carboxylic acid, optionally substituted pyridyl, and phenyl optionally substituted with lower alkoxy or halo, more preferably phenyl, —COOH, pyridin-3-yl, 3-, or 4-methoxyphenyl or 4-fluorophenyl; and (c) $R_7$ is selected from the group consisting of lower alkyl substituted with a heteroaliphatic ring or dialkylamino; or lower alkoxy substituted with a heteroaliphatic ring or dialkylamino, preferably $R_7$ is lower alkyl substituted with a heteroaliphatic ring or dialkylamino; more preferably $R^7$ is 3-diethylaminopropyl or 3-pyrrolidin-1-yl-propyl, 2-dimethylaminoethoxy, 2-diethylaminoethoxy, 2-pyrrolidin-1-yl-ethoxy, or 2-morpholin-4-yl-ethoxy.

In a second aspect, the invention provides for an indolinone compound having a structure set forth in formula (II):

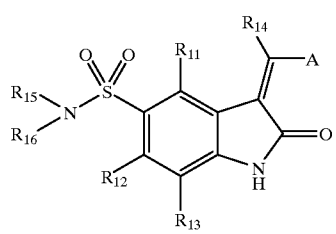

(II)

wherein:

(a) $R_{11}$–$R_{14}$ are hydrogen;

(b) $R_{15}$ and $R_{16}$ are each independently selected from the group consisting of hydrogen, optionally substituted alkyl, optionally substituted aryl, and optionally substituted heteroaryl, or $R_{15}$ and $R_{16}$ taken together with the nitrogen atom to which they are attached form a ring structure selected from the group consisting of a five-membered or six-membered heteroaromatic ring, a five-membered or six-membered heteroaliphatic ring, a nine-membered fused bicyclic heteroaromatic ring, and a ten-membered fused bicyclic heteroaromatic ring; and (c) A is selected from the group consisting of formula (III), (IV), and (V):

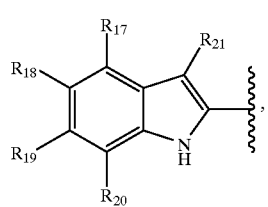

(III)

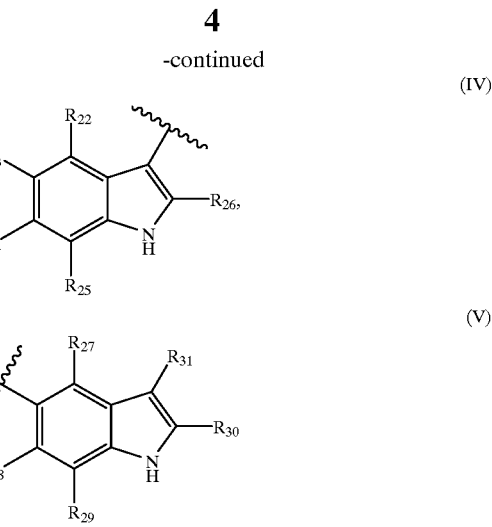

wherein:

(i) $R_{19}$–$R_{25}$ and $R_{27}$–$R_{31}$ are hydrogen;

(ii) $R_{17}$ and $R_{18}$ are each independently selected from the group consisting of hydrogen, optionally substituted alkyl, and optionally substituted alkoxy provided that both $R_{17}$ and $R_{18}$ are not hydrogen; and (iii) $R_{26}$ is selected from the group consisting of optionally substituted alkyl;

or a pharmaceutically acceptable salt thereof.

In one preferred embodiment:

(i) $R_{15}$ is hydrogen or alkyl, more preferably hydrogen or methyl;

(ii) $R_{16}$ is hydrogen, alkyl, phenyl optionally substituted with one or two substituents selected from halo or unsubstituted lower alkyl or 5 or 6 membered heteroaryl; more preferably hydrogen, methyl, isopropyl, phenyl, pyridin-3-yl, 3-chlorophenyl, or 4-chloro-2-fluorophenyl; or (iii) $R_{15}$ and $R_{16}$ together with the nitrogen to which they are attached form 2,3-dihydroindol-1-yl, 2,3-dihydro-2H-quinolin-1-yl, or 2,3-dihydro-2H-isoisoquinolin-2-yl ring wherein said rings are optionally substituted with halo or alkyl, preferably $R_{15}$ and $R_{16}$ together with the nitrogen atom to which they are attached form 2,3-dihydroindol-1-yl, 2,3-dihydro-2H-quinolin-1-yl, 5-bromo-2,3-dihydro-2H-quinolin-1-yl, or 2,3-dihydro-2H-isoisoquinolin-2-yl;

(iv) A is group of formula III where:
$R_{17}$ is hydrogen, methyl, or methoxy, preferably hydrogen; and
$R_{18}$ is selected from the group consisting of lower alkoxy substituted with heteroalicyclic, preferably 2-pyrrolidin-1-yl-ethoxy and 2-morpholin-4-yl-ethoxy.

Another preferred group of compound is that wherein:

(i) $R_{15}$ is hydrogen or alkyl, preferably hydrogen or methyl;

(ii) $R_{16}$ is hydrogen, alkyl, phenyl optionally substituted with one or two substituents selected from halo or unsubstituted lower alkyl, or 5 or 6 membered heteroaryl; preferably hydrogen, methyl, isopropyl, phenyl, pyridin-3-yl, 3-chlorophenyl, or 4-chloro-2-fluorophenyl; or $R_{15}$ and $R_{16}$ together with the nitrogen to which they are attached form 2,3-dihydroindol-1-yl, 2,3-dihydro-2H-quinolin-1-yl, or 2,3-dihydro-2H-isoisoquinolin-2-yl ring wherein said rings are optionally substituted with halo or alkyl, preferably 3-dihydroindol-1-yl, 2,3-dihydro-2H-quinolin-1-yl, 5-bromo-2,3-dihydro-2H-quinolin-1-yl, or 2,3-dihydro-2H-isoisoquinolin-2-yl; and (iii) A is group of formula IV where $R_{26}$ is selected from the group consisting of optionally substituted alkyl, preferably hydrogen or methyl.

Another preferred group of compounds is that wherein:

(i) $R_{15}$ is hydrogen or alkyl, preferably hydrogen or methyl;

(iii) $R_{16}$ is hydrogen, alkyl, phenyl optionally substituted with one or two substituents selected from halo or unsubstituted lower alkyl or 5 or 6 membered heteroaryl; more preferably hydrogen, methyl, isopropyl, phenyl, pyridin-3-yl, 3-chlorophenyl, or 4-chloro-2-fluorophenyl; or $R_{15}$ and $R_{16}$ together with the nitrogen to which they are attached form 2,3-dihydroindol-1-yl, 2,3-dihydro-2H-quinolin-1-yl, or 2,3-dihydro-2H-isoquinolin-2-yl ring wherein said rings are optionally substituted with halo or alkyl, preferably $R_{15}$ and $R_{16}$ together with the nitrogen atom to which they are attached form 2,3-dihydroindol-1-yl, 2,3-dihydro-2H-quinolin-1-yl, 5-bromo-2,3-dihydro-2H-quinolin-1-yl, or 2,3-dihydro-2H-isoisoquinolin-2-yl;

(ii) A is group of formula V.

As used herein, the term "optionally substituted alkyl" refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, non-branched, or cyclic. Preferably, the alkyl group has 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). More preferably, it is a medium size alkyl having 1 to 10 carbon atoms. Most preferably, it is a lower alkyl having 1 to 4 carbon atoms. The alkyl group is optionally substituted with one, two, or three substituents individually and independently selected from cycloalkyl, aryl, heteroaryl, heteroalicyclic, hydroxy, alkoxy, aryloxy, mercapto, alkylthio, arylthio, cyano, or halo. The term "substituted alkyl" means that the alkyl group as defined above carries at least one of the substituents listed above.

The term "optionally substituted aryl" refer to an aromatic carbocyclic group of 6 to 12 ring atoms which has at least one ring having a conjugated π electron system (e.g., phenyl, napthyl, tetrahydronaphthyl, and the like) which is optionally substituted with one, two, or three substituents independently selected from optionally susbstituted alkyl, halogen, trihalomethyl, hydroxy, alkoxy, carboxyl amino, amido, nitro, and ester.

"Optionally substituted phenyl" refers to a phenyl group that is optionally substituted with one, two, or three substituents independently selected from optionally susbstituted alkyl, halogen, trihalomethyl, hydroxy, alkoxy, carboxyl amino, amido, nitro, and ester.

The term "cycloalkyl" refers to a saturated, cyclic group of 3 to 6 carbon atoms (e.g., cyclopropyl, cyclobutyl, cyclopentyl or cyclohexyl) which is optionally substituted with one, two, or three substituents independently selected from optionally susbstituted alkyl, halogen, trihalomethyl, hydroxy, alkoxy, carboxyl amino, amido, nitro, and ester.

The term "optionally susbtituted heteroaryl or heteroaromatic ring" refers to a ring system of 5 to 10 ring atoms in which one, two, three, or four of the atoms forming the backbone is a heteroatom selected from nitrogen, oxygen, or sulfur, the remaining being carbon e.g., pyridine, furan, pyrrole, indole, pyrazine, pyrimidine, tetrazole, imidazole, and the like. The heteroaromatic/heteroaryl ring may be single or fused bicyclic ring and wherein one of the rings may be partially or fully saturated e.g., 2,3-dihydroindole, 2,3-dihydroquinoline, 2,3-dihydroisoquinoline, and the like. The heteroaryl/heteroaromatic ring is optionally substituted with one, two, or three substituents independently selected from optionally susbstituted alkyl, halogen, trihalomethyl, hydroxy, alkoxy, carboxyl amino, amido, nitro, and ester.

The term "optionally susbtituted heteroaliphatic or heteroalicyclic" refers to a saturated ring system of 5 to 9 ring atoms in which in which one, two, three, or four of the atoms forming the backbone is a heteroatom selected from nitrogen, oxygen, or sulfur, the remaining being carbon e.g., piperazine, piperidine, pyrrolidine, morpholine, tetrahydrofuran and the like. The heteroaliphatic ring is optionally substituted with one, two, or three substituents independently selected from optionally susbstituted alkyl, halogen, trihalomethyl, hydroxy, alkoxy, carboxyl amino, amido, nitro, and ester.

The term "halogen" refers to an atom selected from the group consisting of fluorine, chlorine, bromine, and iodine.

The term "trihalomethyl" refers to the —C(X)$_3$ group, where X is a halogen group as defined above e.g., trifluoromethyl, trichloromethyl, tribromomethyl, and the like.

The term "optionally substituted alkoxy" is a group of formula —O-alkyl wherein alkyl is as defined above. The term "substituted alkoxy" means that the alkyl group as defined above carries at least one of the substituents listed above. The term "alkoxy" means that the alkyl chain in the alkoxy group as defined above is not substituted.

When X is hydrogen, then the alkoxy group becomes a "hydroxy" group, i.e., —OH.

A "nitro" is a substituent of formula —NO$_2$.

The term "alkylthio" refers to —SR group where R is unsubstituted alkyl as defined above e.g., methylthio, ethylthio, and the like.

The term "aryloxy" refers to —OR group where R is aryl group as defined above, e.g., phenoxy, and the like.

The term "arylthio" refers to —SR group where R is aryl group as defined above e.g., phenylthio, and the like.

The term "dialkylamino" means —NRR where each R is an unsubstituted alkyl group of 1–6 carbon atoms e.g., dimethylamino, diethylamino, and the like.

The term "optionally substituted ester" refers to —COOR where R is an alkyl group as defined above.

The term "optionally substituted amide" refers to —CONR$^a$R$^b$ where R$^a$ and R$^b$ are hydrogen or unsubstituted lower alkyl.

"Pharmaceutically acceptable salt" refers to those salts which retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, citric acid, maleic acid, succinic acid, tartaric acid, and the like.

Some of the preferred compounds of the invention that have the generic structure of formula I are listed in Table 1.

TABLE 1

| Compound Number | Compound Name |
|---|---|
| IN-001 | 3-[5-(3-diethylamino-propyl)-1H-indol-2-ylmethylene]-1,3-dihydro-indol-2-one |
| IN-002 | 5-bromo-3-[5-(3-diethylamino-propyl)-1H-indol-2-ylmethylene]-1,3-dihydro-indol-2-one |
| IN-003 | 3-[5-(3-diethylamino-propyl)-1H-indol-2-ylmethylene]-6-phenyl-1,3-dihydro-indol-2-one |
| IN-004 | 3-[5-(3-diethylamino-propyl)-1H-indol-2-ylmethylene]-5-phenyl-1,3-dihydro-indol-2-one |
| IN-005 | 3-[5-(2-dimethylamino-ethoxy)-1H-indol-2-ylmethylene]-5-phenyl-1,3-dihydro-indol-2-one |
| IN-006 | 5-phenyl-3-[5-(2-pyrrolidin-1-yl-ethoxy)-1H-indol-2-ylmethylene]-1,3-dihydro-indol-2-one |
| IN-007 | 3-[5-(2-morpholin-4-yl-ethoxy)-1H-indol-2-ylmethylene]-1,3-dihydro-indol-2-one |
| IN-008 | 5-bromo-3-[5-(2-morpholin-4-yl-ethoxy)-1H-indol-2-ylmethylene]-1,3-dihydro-indol-2-one |
| IN-009 | 3-[5-(2-morpholin-4-yl-ethoxy)-1H-indol-2-ylmethylene]-6-phenyl-1,3-dihydro-indol-2-one |
| IN-010 | 3-[5-(2-dimethylamino-ethoxy)-1H-indol-2-ylmethylene]-1,3-dihydro-indol-2-one |
| IN-011 | 5-bromo-3-[5-(2-dimethylamino-ethoxy)-1H-indol-2-ylmethylene]-1,3-dihydro-indol-2-one |
| IN-012 | 3-[5-(2-dimethylamino-ethoxy)-1H-indol-2-ylmethylene]-6-phenyl-1,3-dihydro-indol-2-one |
| IN-013 | 3-[5-(2-pyrrolidin-1-yl-ethoxy)-1H-indol-2-ylmethylene]-1,3-dihydro-indol-2-one |
| IN-014 | 5-bromo-3-[5-(2-pyrrolidin-1-yl-ethoxy)-1H-indol-2-ylmethylene]-1,3-dihydro-indol-2-one |
| IN-015 | 6-phenyl-3-[5-(2-pyrrolidin-1-yl-ethoxy)-1H-indol-2-ylmethylene]-1,3-dihydro-indol-2-one |
| IN-016 | 3-[5-(2-diethylamino-ethoxy)-1H-indol-2-ylmethylene]-1,3-dihydro-indol-2-one |
| IN-017 | 5-bromo-3-[5-(2-diethylamino-ethoxy)-1H-indol-2-ylmethylene]-1,3-dihydro-indol-2-one |
| IN-018 | 3-[5-(2-diethylamino-ethoxy)-1H-indol-2-ylmethylene]-6-phenyl-1,3-dihydro-indol-2-one |
| IN-019 | 3-[5-(2-diethylamino-ethoxy)-1H-indol-2-ylmethylene]-5-phenyl-1,3-dihydro-indol-2-one |
| IN-020 | 3-[5-(3-pyrrolidin-1-yl-propyl)-1H-indol-2-ylmethylene]-1,3-dihydro-indol-2-one |
| IN-021 | 2-oxo-3-[5-(3-pyrrolidin-1-yl-propyl)-1H-indol-2-ylmethylene]-2,3-dihydro-1H-indol-5-carboxylic acid |
| IN-022 | 2-oxo-3-[5-(2-pyrrolidin-1-yl-ethoxy)-1H-indol-2-ylmethylene]-2,3-dihydro-1H-indole-5-carboxylic acid |
| IN-023 | 2-oxo-3-[5-(2-pyrrolidin-1-yl-ethoxy)-1H-indol-2-ylmethylene]-2,3-dihydro-1H-indole-6-carboxylic acid |
| IN-024 | 4-(2-hydroxy-ethyl)-3-[5-(2-pyrrolidin-1-yl-ethoxy)-1H-indol-2-ylmethylene]-1,3-dihydro-indol-2-one |
| IN-025 | 6-pyridin-3-yl-3-[5-(2-pyrrolidin-1-yl-ethoxy)-1H-indol-2-ylmethylene]-1,3-dihydro-indol-2-one |
| IN-026 | 6-(4-methoxy-phenyl)-3-[5-(2-pyrrolidin-1-yl-ethoxy)-1H-indol-2-ylmethylene]-1,3-dihydro-indol-2-one |
| IN-027 | 6-(3-methoxy-phenyl)-3-[5-(2-pyrrolidin-1-yl-ethoxy)-1H-indol-2-ylmethylene]-1,3-dihydro-indol-2-one |
| IN-028 | 6-(2-methoxy-phenyl)-3-[5-(2-pyrrolidin-1-yl-ethoxy)-1H-indol-2-ylmethylene]-1,3-dihydro-indol-2-one |
| IN-029 | 6-(4-fluoro-phenyl)-3-[5-(2-pyrrolidin-1-yl-ethoxy)-1H-indol-2-ylmethylene]-1,3-dihydro-indol-2-one |
| IN-030 | 3-[5-(2-morpholin-4-yl-ethoxy)-1H-indol-2-ylmethylene]-2-oxo-2,3-dihydro-1H-indole-5-carboxylic acid |
| IN-031 | 3-[5-(2-morpholin-4-yl-ethoxy)-1H-indol-2-ylmethylene]-2-oxo-2,3-dihydro-1H-indole-6-carboxylic acid |
| IN-032 | 3-[5-(2-morpholin-4-yl-ethoxy)-1H-indol-2-ylmethylene]-5-phenyl-1,3-dihydro-indol-2-one |
| IN-033 | 4-(2-hydroxy-ethyl)-3-[5-(2-morpholin-4-yl-ethoxy)-1H-indol-2-ylmethylene]-1,3-dihydro-indol-2-one |
| IN-034 | 3-[5-(2-morpholin-4-yl-ethoxy)-1H-indol-2-ylmethylene]-6-pyridin-3-yl-1,3-dihydro-indol-2-one |
| IN-035 | 6-(4-methoxy-phenyl)-3-[5-(2-morpholin-4-yl-ethoxy)-1H-indol-2-ylmethylene]-1,3-dihydro-indol-2-one |

TABLE 1-continued

| Compound Number | Compound Name |
|---|---|
| IN-036 | 6-(3-methoxy-phenyl)-3-[5-(2-morpholin-4-yl-ethoxy)-1H-indol-2-ylmethylene]-1,3-dihydro-indol-2-one |
| IN-037 | 6-(2-methoxy-phenyl)-3-[5-(2-morpholin-4-yl-ethoxy)-1H-indol-2-ylmethylene]-1,3-dihydro-indol-2-one |
| IN-038 | 6-(4-fluoro-phenyl)-3-[5-(2-morpholin-4-yl-ethoxy)-1H-indol-2-ylmethylene]-1,3-dihydro-indol-2-one |

The above compounds have the structure of formula X, with the $R_{101}$, $R_{102}$, $R_{103}$, and $R_{112}$ substituents as defined in Table 2.

TABLE 2

(X)

| Compound Number | $R_{101}$ | $R_{102}$ | $R_{103}$ | $R_{112}$ |
|---|---|---|---|---|
| IN-001 | H | H | 3-diethylamino-propyl | H |
| IN-002 | Br | H | 3-diethylamino-propyl | H |
| IN-003 | H | Phenyl | 3-diethylamino-propyl | H |
| IN-004 | Phenyl | H | 3-diethylamino-propyl | H |
| IN-005 | Phenyl | H | 2-dimethylamino-ethoxy | H |
| IN-006 | Phenyl | H | 2-pyrrolidin-1-yl-ethoxy | H |
| IN-007 | H | H | 2-morpholin-4-yl-ethoxy | H |
| IN-008 | Br | H | 2-morpholin-4-yl-ethoxy | H |
| IN-009 | H | Phenyl | 2-morpholin-4-yl-ethoxy | H |
| IN-010 | H | H | 2-dimethylamino-ethoxy | H |
| IN-011 | Br | H | 2-dimethylamino-ethoxy | H |
| IN-012 | H | Phenyl | 2-dimethylamino-ethoxy | H |
| IN-013 | H | H | 2-pyrrolidin-1-yl-ethoxy | H |
| IN-014 | Br | H | 2-pyrrolidin-1-yl-ethoxy | H |
| IN-015 | H | Phneyl | 2-pyrrolidin-1-yl-ethoxy | H |
| IN-016 | H | H | 2-diethylamino-ethoxy | H |
| IN-017 | Br | H | 2-diethylamino-ethoxy | H |
| IN-018 | H | Phenyl | 2-diethylamino-ethoxy | H |
| IN-019 | Phenyl | H | 2-diethylamino-ethoxy | H |
| IN-020 | H | H | 3-pyrrolidin-1-yl-propyl | H |
| IN-021 | —COOH | H | 3-pyrrolidin-1-yl-propyl | H |
| IN-022 | —COOH | H | 2-pyrrolidin-1-yl-ethoxy | H |

TABLE 2-continued (X)

Structure showing an indolinone with R101, R102, R103, R112 substituents on formula with R103 on indole ring.

| Compound Number | R101 | R102 | R103 | R112 |
|---|---|---|---|---|
| IN-023 | H | —COOH | 2-pyrrolidin-1-yl-ethoxy | H |
| IN-024 | H | H | 2-pyrrolidin-1-yl-ethoxy | 2-hydroxy-ethyl |
| IN-025 | H | Pyridin-3-yl | 2-pyrrolidin-1-yl-ethoxy | H |
| IN-026 | H | 4-Methoxy Phenyl | 2-pyrrolidin-1-yl-ethoxy | H |
| IN-027 | H | 3-Methoxy Phenyl | 2-pyrrolidin-1-yl-ethoxy | H |
| IN-028 | H | 2-Methoxy Phenyl | 2-pyrrolidin-1-yl-ethoxy | H |
| IN-029 | H | 4-Fluoro Phenyl | 2-pyrrolidin-1-yl-ethoxy | H |
| IN-030 | —COOH | H | 2-morpholin-4-yl-ethoxy | H |
| IN-031 | H | —COOH | 2-morpholin-4-yl-ethoxy | H |
| IN-032 | Phenyl | H | 2-morpholin-4-yl-ethoxy | H |
| IN-033 | H | H | 2-morpholin-4-yl-ethoxy | 2-hydroxy-ethyl |
| IN-034 | H | Pyridin-3-yl | 2-morpholin-4-yl-ethoxy | H |
| IN-035 | H | 4-Methoxy Phenyl | 2-morpholin-4-yl-ethoxy | H |
| IN-036 | H | 3-Methoxy Phenyl | 2-morpholin-4-yl-ethoxy | H |
| IN-037 | H | 2-Methoxy Phenyl | 2-morpholin-4-yl-ethoxy | H |
| IN-038 | H | 4-Fluoro Phenyl | 2-morpholin-4-yl-ethoxy | H |

Some of the compounds of the invention that have the generic structure of formula II are listed in Table 3.

TABLE 3

| Compound Number | Compound Name |
|---|---|
| IN-039 | 2-oxo-3-[5-(2-pyrrolidin-1-yl-ethoxy)-1H-indol-2-ylmethylene]-2,3-dihydro-1H-indole-5-sulfonic acid amide |
| IN-040 | 3-[5-(2-morpholin-4-yl-ethoxy)-1H-indol-2-ylmethylene]-2-oxo-2,3-dihydro-1H-indole-5-sulfonic acid amide |
| IN-041 | 2-oxo-3-[5-(2-pyrrolidin-1-yl-ethoxy)-1H-indol-2-ylmethylene]-2,3-dihydro-1H-indole-5-sulfonic acid methylamide |
| IN-042 | 2-oxo-3-[5-(2-pyrrolidin-1-yl-ethoxy)-1H-indol-2-ylmethylene]-2,3-dihydro-1H-indole-5-sulfonic acid dimethylamide |
| IN-043 | 2-oxo-3-[5-(2-pyrrolidin-1-yl-ethoxy)-1H-indol-2-ylmethylene]-2,3-dihydro-1H-indole-5-sulfonic acid isopropylamide |
| IN-044 | 2-oxo-3-[5-(2-pyrrolidin-1-yl-ethoxy)-1H-indol-2-ylmethylene]-2,3-dihydro-1H-indole-5-sulfonic acid phenylamide |
| IN-045 | 2-oxo-3-[5-(2-pyrrolidin-1-yl-ethoxy)-1H-indol-2-ylmethylene]-2,3-dihydro-1H-indole-5-sulfonic acid pyridin-3-ylamide |
| IN-046 | 5-(2,3-dihydro-indole-1-sulfonyl)-3-[5-(2-pyrrolidin-1-yl-ethoxy)-1H-indol-2-ylmethylene]-1,3-dihydro-indol-2-one |
| IN-047 | 2-oxo-3-[5-(2-pyrrolidin-1-yl-ethoxy)-1H-indol-2-ylmethylene]-2,3-dihydro-1H-indole-5-sulfonic acid (3-chloro-phenyl)-amide |
| IN-048 | 2-oxo-3-[5-(2-pyrrolidin-1-yl-ethoxy)-1H-indol-2-ylmethylene]-2,3-dihydro-1H-indole-5-sulfonic acid (3-chloro-phenyl)-methyl-amide |
| IN-049 | 2-oxo-3-[5-(2-pyrrolidin-1-yl-ethoxy)-1H-indol-2-ylmethylene]-2,3-dihydro-1H-indole-5-sulfonic acid (4-chloro-2-fluoro-phenyl)-amide |
| IN-050 | 5-(3,4-dihydro-2H-quinoline-1-sulfonyl)-3-[5-(2-pyrrolidin-1-yl-ethoxy)-1H-indol-2-ylmethylene]-1,3-dihydro-indol-2-one |
| IN-051 | 5-(3,4-dihydro-1H-isoquinoline-2-sulfonyl)-3-[5-(2-pyrrolidin-1-yl-ethoxy)-1H-indol-2-ylmethylene]-1,3-dihydro-indol-2-one |
| IN-052 | 5-(5-bromo-2,3-dihydro-indole-1-sulfonyl)-3-[5-(2-pyrrolidin-1-yl-ethoxy)-1H-indol-2-ylmethylene]-1,3-dihydro-indol-2-one |
| IN-053 | 3-[5-(2-morpholin-4-yl-ethoxy)-1H-indol-2-ylmethylene]-2-oxo-2,3-dihydro-1H-indole-5-sulfonic acid methylamide |
| IN-054 | 3-[5-(2-morpholin-4-yl-ethoxy)-1H-indol-2-ylmethylene]-2-oxo-2,3-dihydro-1H-indole-5-sulfonic acid dimethylamide |
| IN-055 | 3-[5-(2-morpholin-4-yl-ethoxy)-1H-indol-2-ylmethylene]-2-oxo-2,3-dihydro-1H-indole-5-sulfonic acid isopropylamide |
| IN-056 | 3-[5-(2-morpholin-4-yl-ethoxy)-1H-indol-2-ylmethylene]-2-oxo-2,3-dihydro-1H-indole-5-sulfonic acid phenylamide |
| IN-057 | 3-[5-(2-morpholin-4-yl-ethoxy)-1H-indol-2-ylmethylene]-2-oxo-2,3-dihydro-1H-indole-5-sulfonic acid pyridin-3-ylamide |
| IN-058 | 5-(2,3-dihydro-indole-1-sulfonyl)-3-[5-(2-morpholin-4-yl-ethoxy)-1H-indol-2-ylmethylene]-1,3-dihydro-indol-2-one |
| IN-059 | 3-[5-(2-morpholin-4-yl-ethoxy)-1H-indol-2-ylmethylene]-2-oxo-2,3-dihydro-1H-indole-5-sulfonic acid (3-chloro-phenyl)-amide |
| IN-060 | 3-[5-(2-morpholin-4-yl-ethoxy)-1H-indol-2-ylmethylene]-2-oxo-2,3-dihydro-1H-indole-5-sulfonic acid (3-chloro-phenyl)-methyl-amide |
| IN-061 | 3-[5-(2-morpholin-4-yl-ethoxy)-1H-indol-2-ylmethylene]-2-oxo-2,3-dihydro-1H-indole-5-sulfonic acid (4-chloro-2-fluoro-phenyl)-amide |
| IN-062 | 5-(3,4-dihydro-2H-quinoline-1-sulfonyl)-3-[5-(2-morpholin-4-yl-ethoxy)-1H-indol-2-ylmethylene]-1,3-dihydro-indol-2-one |
| IN-063 | 5-(3,4-dihydro-1H-isoquinoline-2-sulfonyl)-3-[5-(2-morpholin-4-yl-ethoxy)-1H-indol-2-ylmethylene]-1,3-dihydro-indol-2-one |
| IN-064 | 5-(5-bromo-2,3-dihydro-indole-1-sulfonyl)-3-[5-(2-morpholin-4-yl-ethoxy)-1H-indol-2-ylmethylene]-1,3-dihydro-indol-2-one |
| IN-065 | 3-(1H-indol-3-ylmethylene)-2-oxo-2,3-dihydro-1H-indole-5-sulfonic acid amide |
| IN-066 | 3-(2-methyl-1H-indol-3-ylmethylene)-2-oxo-2,3-dihydro-1H-indole-5-sulfonic acid amide |
| IN-067 | 3-(1H-indol-5-ylmethylene)-2-oxo-2,3-dihydro-1H-indole-5-sulfonic acid amide |
| IN-068 | 3-(1H-indol-3-ylmethylene)-2-oxo-2,3-dihydro-1H-indole-5-sulfonic acid methylamide |
| IN-069 | 3-(2-methyl-1H-indol-3-ylmethylene)-2-oxo-2,3-dihydro-1H-indole-5-sulfonic acid methylamide |
| IN-070 | 3-(1H-indol-5-ylmethylene)-2-oxo-2,3-dihydro-1H-indole-5-sulfonic acid methylamide |
| IN-071 | 3-(1H-indol-2-ylmethylene)-2-oxo-2,3-dihydro-1H-indole-5-sulfonic acid methylamide |
| IN-072 | 3-(1H-indol-3-ylmethylene)-2-oxo-2,3-dihydro-1H-indole-5-sulfonic acid dimethylamide |
| IN-073 | 3-(2-methyl-1H-indol-3-ylmethylene)-2-oxo-2,3-dihydro-1H-indole-5-sulfonic acid dimethylamide |

TABLE 3-continued

| Compound Number | Compound Name |
|---|---|
| IN-074 | 3-(1H-indol-5-ylmethylene)-2-oxo-2,3-dihydro-1H-indole-5-sulfonic acid dimethylamide |
| IN-075 | 3-(1H-indol-2-ylmethylene)-2-oxo-2,3-dihydro-1H-indole-5-sulfonic acid dimethylamide |
| IN-076 | 3-(4-methoxy-1H-indol-2-ylmethylene)-2-oxo-2,3-dihydro-1H-indole-5-sulfonic acid methylamide |

Some of the above compounds have the structure of formula XI, with the $R_{104}$, $R_{105}$, $R_{106}$, and $R_{113}$ substituents as defined in Table 4, while others have the structure of formula XII, with the $R_{107}$, $R_{108}$, and $R_{109}$ substituents as defined in Table 5, and still others have the structure of formula XIII, with the $R_{110}$ and $R_{111}$ substituents as defined in Table 6.

TABLE 4

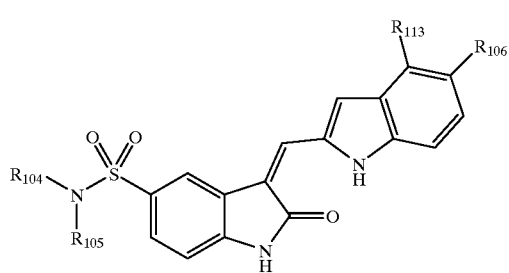

(XI)

| Compound Number | $R_{104}$ | $R_{105}$ | $R_{106}$ | $R_{113}$ |
|---|---|---|---|---|
| IN-039 | H | H | 2-pyrrolidin-1-yl-ethoxy | H |
| IN-040 | H | H | 2-morpholin-4-yl-ethoxy | H |
| IN-041 | H | CH₃ | 2-pyrrolidin-1-yl-ethoxy | H |
| IN-042 | CH₃ | CH₃ | 2-pyrrolidin-1-yl-ethoxy | H |
| IN-043 | H | Isopropyl | 2-pyrrolidin-1-yl-ethoxy | H |
| IN-044 | H | Phenyl | 2-pyrrolidin-1-yl-ethoxy | H |
| IN-045 | H | Pyridin-3-yl | 2-pyrrolidin-1-yl-ethoxy | H |
| IN-046 | $R_{104}$ and $R_{105}$ taken together form a 2,3-dihydroindol-1-yl ring | | 2-pyrrolidin-1-yl-ethoxy | H |
| IN-047 | H | 3-Chloro-phenyl | 2-pyrrolidin-1-yl-ethoxy | H |
| IN-048 | CH₃ | 3-Chloro-phenyl | 2-pyrrolidin-1-yl-ethoxy | H |
| IN-049 | H | 4-Chloro-2-fluorophenyl | 2-pyrrolidin-1-yl-ethoxy | H |
| IN-050 | $R_{104}$ and $R_{105}$ taken together form a 3,4-dihydro-2H-quinolin-1-yl ring | | 2-pyrrolidin-1-yl-ethoxy | H |
| IN-051 | $R_{104}$ and $R_{105}$ taken together form a 3,4-dihydro-2H-isoquinolin-2-yl ring | | 2-pyrrolidin-1-yl-ethoxy | H |
| IN-052 | $R_{104}$ and $R_{105}$ taken together form a 5-bromo-2,3-dihydro-indol-1-yl ring | | 2-pyrrolidin-1-yl-ethoxy | H |
| IN-053 | H | CH₃ | 2-morpholin-4-yl-ethoxy | H |

TABLE 4-continued

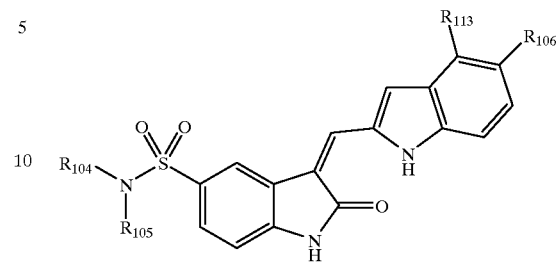

(XI)

| Compound Number | $R_{104}$ | $R_{105}$ | $R_{106}$ | $R_{113}$ |
|---|---|---|---|---|
| IN-054 | CH₃ | CH₃ | 2-morpholin-4-yl-ethoxy | H |
| IN-055 | H | Isopropyl | 2-morpholin-4-yl-ethoxy | H |
| IN-056 | H | Phenyl | 2-morpholin-4-yl-ethoxy | H |
| IN-057 | H | Pyridin-3-yl | 2-morpholin-4-yl-ethoxy | H |
| IN-058 | $R_{104}$ and $R_{105}$ taken together form a 2,3-dihydroindol-1-yl ring | | 2-morpholin-4-yl-ethoxy | H |
| IN-059 | H | 3-Chloro-phenyl | 2-morpholin-4-yl-ethoxy | H |
| IN-060 | CH₃ | 3-Chloro-phenyl | 2-morpholin-4-yl-ethoxy | H |
| IN-061 | H | 4-Chloro-2-fluorophenyl | 2-morpholin-4-yl-ethoxy | H |
| IN-062 | $R_{104}$ and $R_{105}$ taken together form a 3,4-dihydro-2H-quinolin-1-yl ring | | 2-morpholin-4-yl-ethoxy | H |
| IN-063 | $R_{104}$ and $R_{105}$ taken together form a 3,4-dihydro-2H-isoquinolin-2-yl ring | | 2-morpholin-4-yl-ethoxy | H |
| IN-064 | $R_{104}$ and $R_{105}$ taken together form a 5-bromo-2,3-dihydro-indol-1-yl ring | | 2-morpholin-4-yl-ethoxy | H |
| IN-071 | H | CH₃ | H | H |
| IN-075 | CH₃ | CH₃ | H | H |
| IN-076 | H | CH₃ | H | Methoxy |

TABLE 5

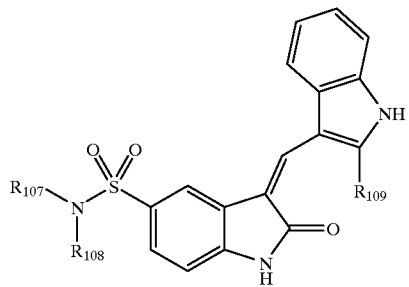

(XII)

| Compound Number | $R_{107}$ | $R_{108}$ | $R_{109}$ |
|---|---|---|---|
| IN-065 | H | H | H |
| IN-066 | H | H | CH₃ |
| IN-068 | CH₃ | H | H |
| IN-069 | CH₃ | H | CH₃ |
| IN-072 | CH₃ | CH₃ | H |

TABLE 5-continued (XII)

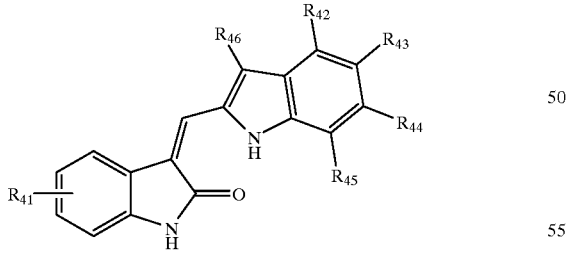

| Compound Number | $R_{107}$ | $R_{108}$ | $R_{109}$ |
|---|---|---|---|
| IN-073 | $CH_3$ | $CH_3$ | $CH_3$ |

TABLE 6

(XIII)

| Compound Number | $R_{110}$ | $R_{111}$ |
|---|---|---|
| IN-067 | H | H |
| IN-070 | $CH_3$ | H |
| IN-074 | $CH_3$ | $CH_3$ |

In a further aspect, the invention relates to an indolinone compound having a structure set forth in formula VI:

(VI)

where
(a) $R_{41}$ is selected from the group consisting of hydrogen, amide, and sulfonamide;
(b) $R_{42}$ and $R_{44}$ are each independently selected from the group consisting of hydrogen, halogen, and alkoxy;
(c) $R_{43}$ is selected from the group consisting of hydrogen, alkyl, halogen, hydroxy, alkoxy, perhaloalkoxy, nitro, sulfone, and sulfonamide;
(d) $R_{45}$ is selected from the group consisting of hydrogen, alkyl, nitro, and amide; and
(e) $R_{46}$ is selected from the group consisting of hydrogen, alkyl, carboxylic acid, and amine.

Preferably, for the compounds of formula VI,
(a) $R_{42}$ and $R_{44}$ are each independently selected from the group consisting of hydrogen, chloro, and methoxy;
(b) $R_{43}$ is selected from the group consisting of, hydrogen, fluoro, chloro, bromo, methoxy, hydroxy, methyl, ethyl, nitro, trifluoromethoxy, $—SO_2CH_3$, and $—NHSO_2CH_3$,
(c) $R_{45}$ is selected from the group consisting of hydrogen, methyl, $—NO_2$, and $—NHC(O)C(CH_3)_3$, and
(d) $R_{46}$ is selected from the group consisting of hydrogen, methyl, $—CH_2N(CH_3)_2$, $—CH_2N(CH_2CH_3)_2$, $—CH_2CH_2C(O)OH$, and $—CH_2CH_2CH_2C(O)OH$.

The preferred compounds of the invention that have the structure set forth in formula VI are selected from the group consisting of (1)

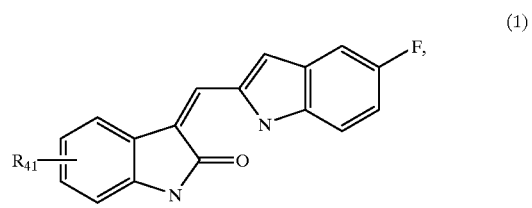

(2)

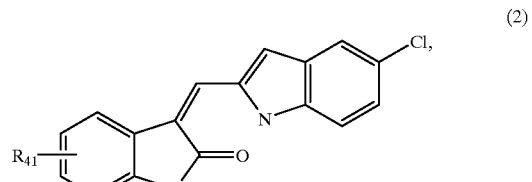

(3)

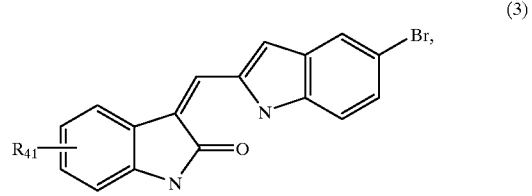

(4)

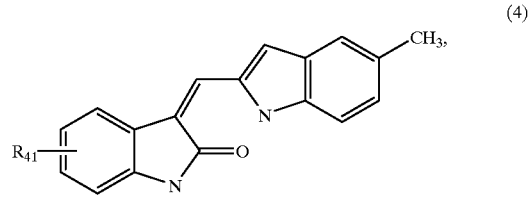

(5)

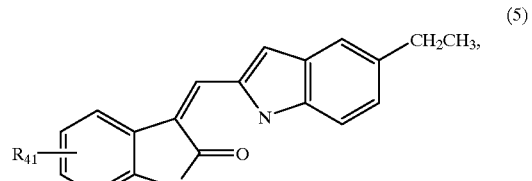

(6)

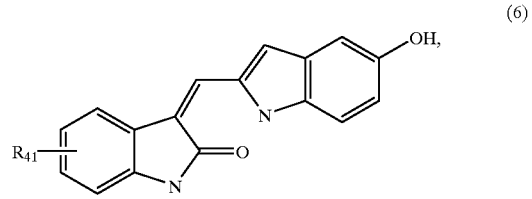

-continued
(7)
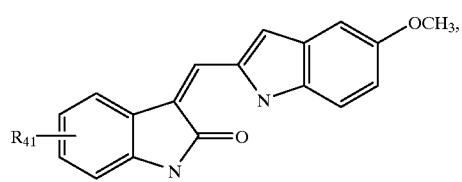
(8)
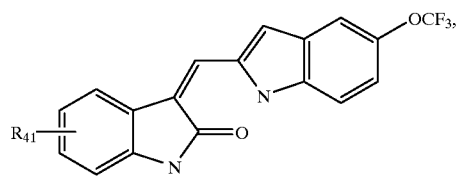
(9)
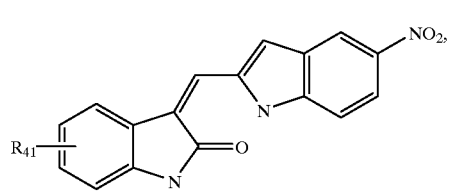
(10)
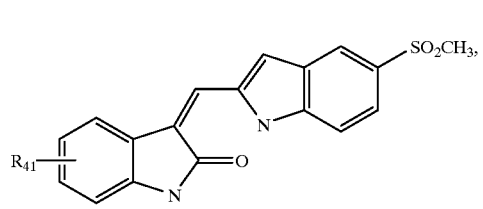
(11)
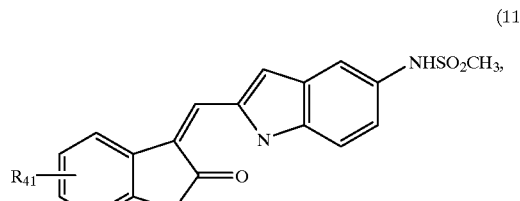
(12)
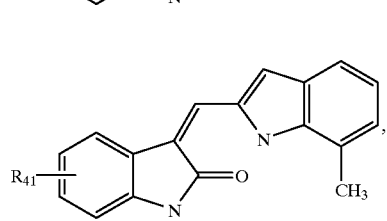
(13)
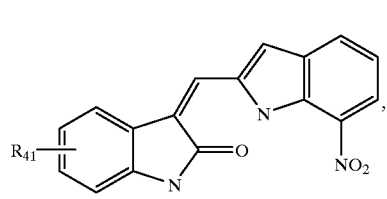
(14)
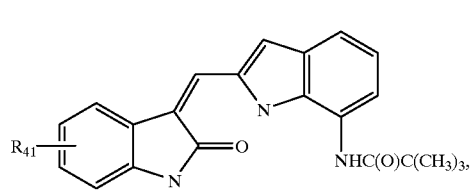
-continued
(15)
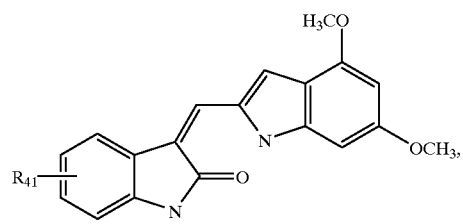
(16)
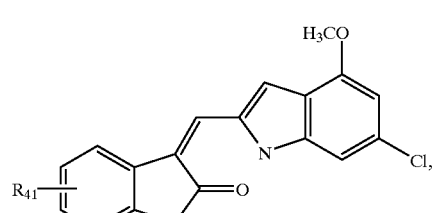
(17)
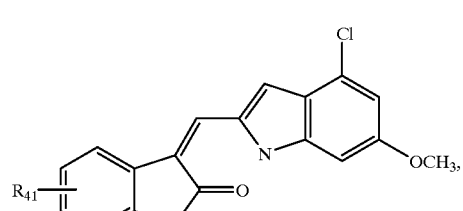
(18)
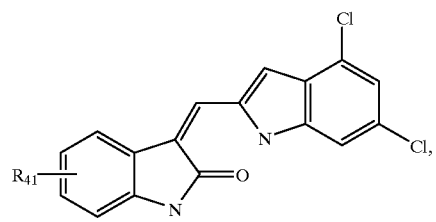
(19)
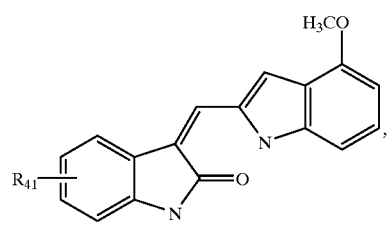
(20)
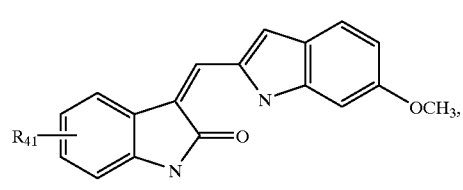
(21)
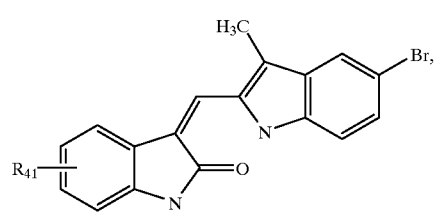

-continued

(22)
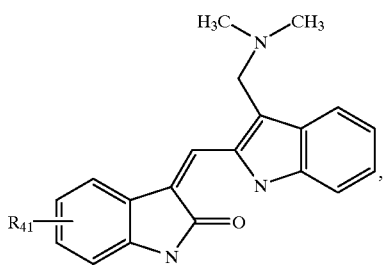

(23)
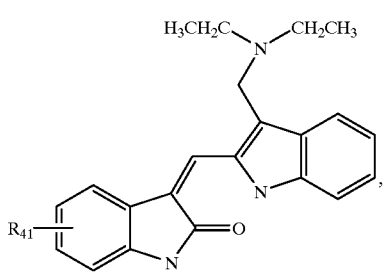

(24)
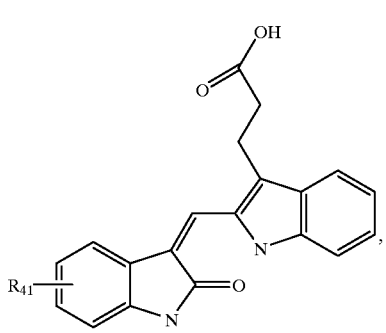

(25)
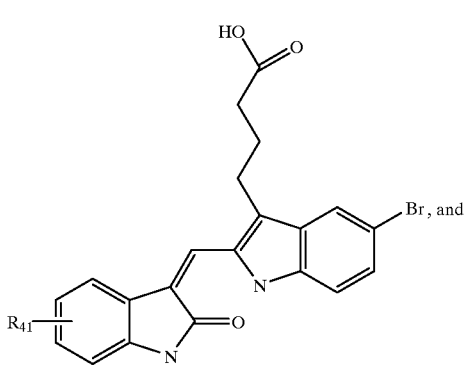

(26)
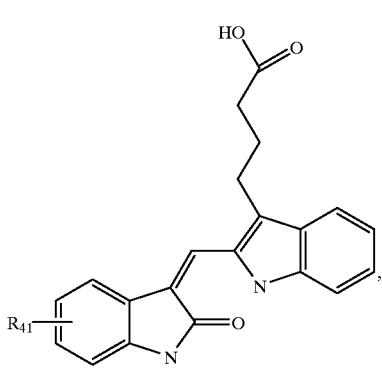

where $R_{41}$ is selected from the group consisting of —$SO_2N(X_1)_2$, —$NHSO_2X_1$, —$NHC(O)X_1$, where $X_1$ is hydrogen or alkyl.

In another aspect, the invention relates to a combinatorial library of at least five indolinone compounds that can be formed by reacting an oxindole with an aldehyde where the oxindole has a structure set forth in formula VII or VIII:

(VII)
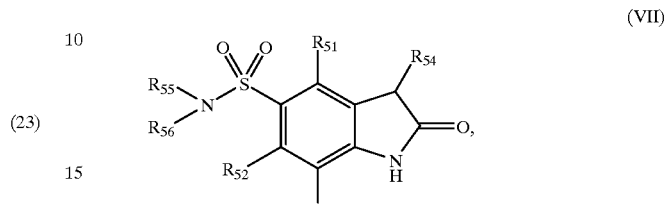

(VIII)
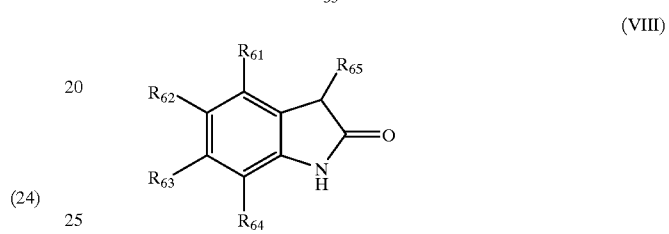

where
(a) $R_{51}$–$R_{54}$, $R_{64}$, and $R_{65}$ are hydrogen;
(b) $R_{55}$ and $R_{56}$ are each independently selected from the group consisting of hydrogen, optionally substituted alkyl, optionally substituted aryl, and optionally substituted heteroaryl, or when taken together $R_{55}$ and $R_{56}$ form an optionally substituted five-membered or six-membered heteroaliphatic ring;
(c) $R_{61}$–$R_{63}$ are each independently selected from the group consisting of hydrogen, halogen, carboxylic acid, optionally substituted aryl, optionally substituted heteroaryl, and amide; and where the aldehyde has a structure set forth in formula IX (IX)
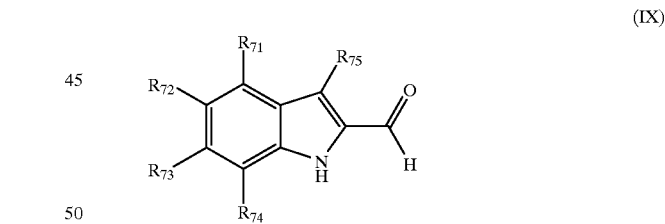

where
(d) $R_{71}$ and $R_{73}$–$R_{75}$ are hydrogen;
(e) $R_{72}$ is selected from the group consisting of hydrogen, optionally substituted alkyl, and optionally substituted alkoxy.

A "combinatorial library" refers to all the compounds formed by the reaction of each compound of one dimension with a compound in each of the other dimensions in a multi-dimensional array of compounds. In the context of the present invention, the array is two dimensional and one dimension represents all the oxindoles of the invention and the second dimension represents all the aldehydes of the invention. Each oxindole may be reacted with each and every aldehyde in order to form an indolinone compound. All indolinone compounds formed in this way are within the scope of the present invention. Also within the scope of the present invention are smaller combinatorial libraries formed by the reaction of some of the oxindoles with all of the aldehydes, all of the oxindoles with some of the aldehydes, or some of the oxindoles with some of the aldehydes.

Preferably in the combinatorial library of the invention:
(a) $R_{55}$ and $R_{56}$ are each independently selected from the group consisting of hydrogen, methyl, isopropyl, 2-methoxyethyl, benzyl, 4-fluorobenzyl, 2-methoxyphenyl, 3-fluorophenyl, 4-fluorophenyl, 3-chlorophenyl, 3-pyridyl, or when taken together $R_{55}$ and $R_{56}$ form a ring selected from the group consisting of pyrrolidine, 4-methylpiperazine;
(b) $R_{61}$–$R_{63}$ are each independently selected from the group consisting of hydrogen, bromo, phenyl, 2-methoxyphenyl, 3-methoxyphenyl, 4-methoxyphenyl, 3-pyridyl, —COOH, —C(O)NHCH$_2$CH$_3$, —C(O)NHCH$_2$C(O)OH, —C(O)NHCH(CH$_3$)C(O)OH, —C(O)NHCH(CH(CH$_3$)$_2$)C(O)OH, and

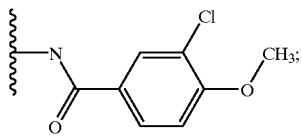

(c) $R_{72}$ is selected from the group consisting of hydrogen 2-diethylamino-ethoxy, 3-diethylamino-1-yl-propyl, and 3-pyrrolidin-1-yl-propyl.

Even more preferably, in the combinatorial library of the invention the aldehyde is selected from the group consisting of 2-formyl-1H-indole, 2-formyl-5-(3-diethylamino-propyl)-1H-indole, 2-formyl-5-(2-dimethylaminoethoxy)-1H-indole, 2-formyl-5-(2-dimethylaminethoxy)-1H-indole, 2-formyl-5-(2-morpholin-4-yl-ethoxy)-1H-indole, 2-formyl-5-(2-pyrrolidine-1-yl-ethoxy)-1H-indole, 2-methyl-1H-indole-3-carbaldehy
and the oxindole is selected from the group consisting of 2-oxo-2,3-dihydro-1H-indole-5-sulfonic acid amide, 2methylamide, 2-oxo-2,3-dihydro-1H-indole-5-sulfonic acid dimethylamide, 2-oxo-2,3-dihydro-1H-indole-5-sulfonic acid (4-chloro-2-fluoro-phenyl)-ethyl-amide, 5-(2,3-dihydro-indole-1-sulfonyl)-1,3-dihydro-indol-2-one, 2-oxo-2,3-dihydro-1H-indole-5-sulfonic acid (4-chloro-2-fluoro-phenyl)-methyl-amide, 2-oxo-2,3-dihydro-1H-indole-5-sulfonic acid (4-chloro-2-fluoro-phenyl)-amide, 5-phenyl-1,3-dihydro-indol-2-one, 2-oxo-2,3-dihydro-1H-indole-5-sulfonic acid [2-(4-methoxy-phenyl)-2-oxo-ethyl]-amide, 2-oxo-2,3-dihydro-1H-indole-5-sulfonic acid (3-methoxy-phenyl)-amide, N-(2-oxo-2,3-dihydro-1H-indol-5-yl)-benzamide, cyclopentanecarboxylic acid (2-oxo-2,3-dihydro-1H-indol-5-yl)-amide, (2-oxo-2,3-dihydro-1H-indol-5-yl)-carbamic acid benzyl ester, 2-oxo-2,3-dihydro-1H-indole-5-sulfonic acid-4-fluoro-benzylamide, 2-oxo-2,3-dihydro-1H-indole-5-sulfonic acid [3-(2-oxo-pyrrolidin-1-yl)-propyl]-amide, 2-oxo-2,3-dihydro-1H-indole-5-sulfonic acid (1,2,3,4-tetrahydro-naphthalen-1-yl)-amide, 2-oxo-2,3-dihydro-1H-indole-5-sulfonic acid (furan-2-ylmethyl)-amide, 3-(2-oxo-2,3-dihydro-1H-indole-5-sulfonylamino)-thiophene-2-carboxylic acid methyl ester, 2-oxo-2,3-dihydro-1H-indole-5-sulfonic acid (3-chloro-phenyl)-amide, 2-oxo-2,3-dihydro-1H-indole-5-sulfonic acid m-tolylamide, 2-oxo-2,3-dihydro-1H-indole-5-sulfonic acid (2-hydroxy-ethyl)-amide, 4-(2-oxo-2,3-dihydro-1H-indole-5-sulfonyl)-piperazine-1-carboxylic acid ethyl ester, 4-(2-oxo-2,3-dihydro-1H-indole-5-sulfonyl)-piperazine-1-carbaldehyde, 2-oxo-2,3-dihydro-1H-indole-5-sulfonic acid (2-methoxy-ethyl)-amide, 2-oxo-2,3-dihydro-1H-indole-5-sulfonic acid propylamide, 5-(4-methyl-piperazine-1-sulfonyl)-1,3-dihydro-indol-2-one, 2-oxo-2,3-dihydro-1H-indole-5-sulfonic acid benzylamide, 2-oxo-2,3-dihydro-1H-indole-5-sulfonic acid (2-methoxy-phenyl)-amide, 2-oxo-2,3-dihydro-1H-indole-5-sulfonic acid cyclopropylamide, 2-oxo-2,3-dihydro-1H-indole-5-sulfonic acid pyridin-3-ylamide, 2-oxo-2,3-dihydro-1H-indole-5-sulfonic acid phenylamide, 5-(pyrrolidine-1-sulfonyl)-1,3-dihydro-indol-2-one, 5-(4-acetyl-piperazine-1-sulfonyl)-1,3-dihydro-indol-2-one, 2-oxo-2,3-dihydro-1H-indole-5-sulfonic acid cyclohexylamide, 2-oxo-2,3-dihydro-1H-indole-5-sulfonic acid (2-morpholin-4-yl-ethyl)-amide, 2-oxo-2,3-dihydro-1H-indole-5-sulfonic acid cyclobutylamide, 2-oxo-2,3-dihydro-1H-indole-5-sulfonic acid (1-phenyl-ethyl)-amide, 2-oxo-2,3-dihydro-1H-indole-5-sulfonic acid cyclopentylamide, 5-(2-pyrrolidin-1-yl-acetyl)-1,3-dihydro-indol-2-one, N-(2-oxo-2,3-dihydro-1H-indole-5-yl)-acetamide, (2-oxo-2,3-dihydro-1H-indole-5-yl)-carbamic acid tert-butyl ester, 2-oxo-2,3-dihydro-1H-indole-5-sulfonic acid isopropylamide, toluene-4-sulfonic acid 2-(2-oxo-2,3-dihydro-1H-indole-4-yl)-ethyl ester, 2-oxo-2,3-dihydro-1H-indole-4-carboxylic acid ethylamide, 4-phenyl-1,3-dihydro-indol-2-one, 2-oxo-2,3-dihydro-1H-indole-4-carboxylic acid (4-methoxy-phenyl)-amide, 4-(2-morpholin-4-yl-ethyl)-1,3-dihydro-indol-2-one, 4-(2-pyrrolidin-1-yl-ethyl)-1,3-dihydro-indol-2-one, 4-[2-(4-methyl-piperazin-1-yl)-ethyl]-1,3-dihydro indol-2-one, 4-[2-(3-bromo-phenoxy)-ethyl]-1,3-dihydro-indol-2-one, 4-(2-bromo-ethyl)-1,3-dihydro-indol-2-one, 4-(2-bromo-ethyl)-1,3-dihydro-indol-2-one, 2-oxo-2,3-dihydro-1H-indole-4-carboxylic acid (6-methoxy-4'-methylsulfanyl-biphenyl-3-yl)-amide, 2-oxo-2,3-dihydro-1H-indole-4-carboxylic acid (4-methoxy-3-thiophen-3-yl-phenyl)-amide, 2-oxo-2,3-dihydro-1H-indole-4-carboxylic acid biphenyl-3-ylamide, 2-oxo-2,3-dihydro-1H-indole-4-carboxylic acid (6-methoxy-3'-trifluoromethyl-biphenyl-3-yl)-amide, 2-oxo-2,3-dihydro-1H-indole-4-carboxylic acid (4'-fluoro-6-methoxy-biphenyl-3-yl)-amide, 2-oxo-2,3-dihydro-1H-indole-4-carboxylic acid (6-methoxy-[1,1',4',1"]terphenyl-3-yl)-amide, 2-oxo-2,3-dihydro-1H-indole-4-carboxylic acid (6,4'-dimethoxy-biphenyl-3-yl)-amide, 2-oxo-2,3-dihydro-1H-indole-4-carboxylic acid (3-chloro-4-methoxy-phenyl)-amide, isopropyl-carbamic acid-2-(2-oxo-2,3-dihydro-1H-indol-4-yl)-ethyl ester, 4-[2-(3-trifluoromethyl-phenoxy)-ethyl]-1,3-dihydro-indol-2-one, 4-[2-(5-chloro-pyridin-3-yloxy)-ethyl]-1,3-dihydro-indol-2-one, 4-[2-(4-methoxy-phenoxy)-ethyl]-1,3-dihydro-indol-2-one, 4-(2-ethoxy-ethyl)-1,3-dihydro-indol-2-one, 4-(2-methoxy-ethyl)-1,3-dihydro-indol-2-one, ethyl-carbamic acid-2-(2-oxo-2,3-dihydro-1H-indol-4-yl)-ethyl ester, biphenyl-2-yl-carbamic acid-2-(2-oxo-2,3-dihydro-1H-indol-4-yl)-ethyl ester, 6-pyridin-3-yl-1,3-dihydro-indol-2-one, 6-phenyl-1,3-dihydro-indol-2-one, 6-(2-methoxy-phenyl)-1,3-dihydro-indol-2-one, 6-(3-methoxy-phenyl)-1,3-dihydro-indol-2-one, 6-(4-methoxy-phenyl)-1,3-dihydro-indol-2-one, and cyclohexyl-carbamic acid-2-(2-oxo-2,3-dihydro-1H-indol-4-yl)-ethyl ester.

Some of the compounds of the invention that can be formed by the above combinatorial library are listed in Table 7.

TABLE 7

| Compound Number | Compound Name |
|---|---|
| CL-001 | 3-[5-(3-diethylamino-propyl)-1H-indol-2-ylmethylene]-2-oxo-2,3-dihydro-1H-indole-5-sulfonic acid dimethyl amide |
| CL-002 | 3-[5-(3-diethylamino-propyl)-1H-indol-2-ylmethylene]-5-(4-methyl-piperazine-1-sulfonyl)-1,3-dihydro-indol-2-one |
| CL-003 | 3-[5-(3-diethylamino-propyl)-1H-indol-2-ylmethylene]-5-(pyrrolidine-1-sulfonyl)-1,3-dihydro-indol-2-one |
| CL-004 | 3-[5-(3-diethylamino-propyl)-1H-indol-2-ylmethylene]-2-oxo-2,3-dihydro-1H-indole-5-sulfonic acid (2-methoxy-ethyl)-amide |
| CL-005 | 3-[5-(3-diethylamino-propyl)-1H-indol-2-ylmethylene]-2-oxo-2,3-dihydro-1H-indole-5-sulfonic acid pyridin-3-ylamide |
| CL-006 | 3-[5-(3-diethylamino-propyl)-1H-indol-2-ylmethylene]-2-oxo-2,3-dihydro-1H-indole-5-sulfonic acid (2-methoxyphenyl)amide |
| CL-007 | 3-[5-(3-diethylamino-propyl)-1H-indol-2-ylmethylene]-2-oxo-2,3-dihydro-1H-indole-5-sulfonic acid (3-chlorophenyl)amide |
| CL-008 | 3-[5-(3-diethylamino-propyl)-1H-indol-2-ylmethylene]-2-oxo-2,3-dihydro-1H-indole-5-sulfonic acid (4-fluorobenzyl)amide |
| CL-009 | 3-[5-(3-diethylamino-propyl)-1H-indol-2-ylmethylene]-2-oxo-2,3-dihydro-1H-indole-5-sulfonic acid amide |
| CL-010 | 3-[5-(3-diethylamino-propyl)-1H-indol-2-ylmethylene]-2-oxo-2,3-dihydro-1H-indole-5-sulfonic acid isopropylamide |
| CL-011 | 3-(1H-indol-2-ylmethylene)-2-oxo-2,3-dihydro-1H-indole-5-sulfonic acid benzylamide |
| CL-012 | 3-(1H-indol-2-ylmethylene)-5-(pyrrolidine-1-sulfonyl)-1,3-dihydro-indol-2-one |
| CL-013 | 3-(1H-indol-2-ylmethylene)-2-oxo-2,3-dihydro-1H-indole-5-sulfonic acid (2-methoxyethyl)amide |
| CL-014 | 3-(1H-indol-2-ylmethylene)-2-oxo-2,3-dihydro-1H-indole-5-sulfonic acid (2-methoxyphenyl)amide |
| CL-015 | 3-(1H-indol-2-ylmethylene)-2-oxo-2,3-dihydro-1H-indole-5-sulfonic acid (3-chlorophenyl)amide |
| CL-016 | 3-(1H-indol-2-ylmethylene)-2-oxo-2,3-dihydro-1H-indole-5-sulfonic acid (4-fluorobenzyl)amide |
| CL-017 | 3-(1H-indol-2-ylmethylene)-2-oxo-2,3-dihydro-1H-indole-5-sulfonic acid amide |
| CL-018 | 3-(1H-indol-2-ylmethylene)-2-oxo-2,3-dihydro-1H-indole-5-sulfonic acid methylamide |
| CL-019 | 3-(1H-indol-2-ylmethylene)-2-oxo-2,3-dihydro-1H-indole-5-sulfonic acid dimethylamide |
| CL-020 | 3-(1H-indol-2-ylmethylene)-2-oxo-2,3-dihydro-1H-indole-5-sulfonic acid isopropylamide |
| CL-021 | 5-bromo-3-[5-(2-diethylaminoethoxy)-1H-indol-2-ylmethylene]-1,3-dihydro-indol-2-one |
| CL-022 | 3-[5-(2-diethylaminoethoxy)-1H-indol-2-ylmethylene]-6-(3-methoxyphenyl)-1,3-dihydro-indol-2-one |
| CL-023 | 3-[5-(2-diethylaminoethoxy)-1H-indol-2-ylmethylene]-6-(4-methoxyphenyl)-1,3-dihydro-indol-2-one |
| CL-024 | 3-[5-(2-diethylaminoethoxy)-1H-indol-2-ylmethylene]-6-phenyl-1,3-dihydro-indol-2-one |
| CL-025 | 3-[5-(2-diethylaminoethoxy)-1H-indol-2-ylmethylene]-6-(2-methoxyphenyl)-1,3-dihydro-indol-2-one |
| CL-026 | 3-[5-(2-diethylaminoethoxy)-1H-indol-2-ylmethylene]-2-oxo-2,3-dihydro-1H-indole-4-carboxylic acid ethylamine |
| CL-027 | 6-bromo-3-[5-(2-diethylaminoethoxy)-1H-indol-2-ylmethylene]-1,3-dihydro-indol-2-one |
| CL-028 | 3-[5-(2-diethylaminoethoxy)-1H-indol-2-ylmethylene]-6-pyridin-1,3-dihydro-indol-2-one |
| CL-029 | 3-[5-(2-diethylaminoethoxy)-1H-indol-2-ylmethylene]-5-phenyl-1,3-dihydro-indol-2-one |
| CL-030 | 3-[5-(2-diethylaminoethoxy)-1H-indol-2-ylmethylene]-2-oxo-2,3-dihydro-1H-indole-4-carboxylic acid (3-chloro-4-methoxyphenyl)-amide |
| CL-031 | 2-oxo-3-[5-(3-pyrrolidin-1-yl-propyl)-1H-indol-2-ylmethylene]-2,3-dihydro-1H-indole-5-carboxylic acid |

TABLE 7-continued

| Compound Number | Compound Name |
|---|---|
| CL-032 | 2-oxo-3-[5-(3-pyrrolidin-1-yl-propyl)-1H-indol-2-ylmethylene]-2,3-dihydro-1H-indole-6-carboxylic acid |
| CL-033 | ({2-oxo-3-[5-(3-pyrrolidin-1-yl-propyl)-1H-indol-2-ylmethylene]-2,3-dihydro-1H-indole-5-carbonyl}-amino)-acetic acid |
| CL-034 | 2-({2-oxo-3-[5-(3-pyrrolidin-1-yl-propyl)-1H-indol-2-ylmethylene]-2,3-dihydro-1H-indole-6-carbonyl}-amino)-acetic acid |
| CL-035 | ({2-oxo-3-[5-(3-pyrrolidin-1-yl-propyl)-1H-indol-2-ylmethylene]-2,3-dihydro-1H-indole-5-carbonyl}-amino)-propionic acid |
| CL-036 | 3-methyl-2-({2-oxo-3-[5-(3-pyrrolidin-1-yl-propyl)-1H-indol-2-ylmethylene]-2,3-dihydro-1H-indole-5-carbonyl}-amino)-butyric acid |
| CL-037 | 2-({2-oxo-3-[5-(3-pyrrolidin-1-yl-propyl)-1H-indol-2-ylmethylene]-2,3-dihydro-1H-indole-6-carbonyl}-amino)-propionic acid |
| CL-038 | 3-methyl-2-({2-oxo-3-[5-(3-pyrrolidin-1-yl-propyl)-1H-indol-2-ylmethylene]-2,3-dihydro-1H-indole-6-carbonyl}-amino)-butyric acid |

Some of the above compounds have the structure of formula XIV, with the $R_{114}$, $R_{115}$, and $R_{116}$ substituents as defined in Table 8, while others have the structure of formula XV, with the $R_{107}$, $R_{108}$, and $R_{109}$ substituents as defined in Table 9.

TABLE 8

(XIV)

[Structure of formula XIV showing indole-sulfonamide with substituents $R_{114}$, $R_{115}$, $R_{116}$]

| Compound Number | $R_{114}$ | $R_{115}$ | $R_{116}$ |
|---|---|---|---|
| CL-001 | CH$_3$ | CH$_3$ | 3-diethylamino-propyl |
| CL-002 | $R_{114}$ and $R_{115}$ together form 4-methyl-piperazin-1-yl | | 3-diethylamino-propyl |
| CL-003 | $R_{114}$ and $R_{115}$ together form pyrrolidin-1-yl | | 3-diethylamino-propyl |
| CL-004 | 2-methoxyethyl | H | 3-diethylamino-propyl |
| CL-005 | pyridin-3-yl | H | 3-diethylamino-propyl |
| CL-006 | 2-methoxyphenyl | H | 3-diethylamino-propyl |
| CL-007 | 3-chlorophenyl | H | 3-diethylamino-propyl |
| CL-008 | 4-fluorobenzyl | H | 3-diethylamino-propyl |
| CL-009 | H | H | 3-diethylamino-propyl |
| CL-010 | isopropyl | H | 3-diethylamino-propyl |
| CL-011 | benzyl | H | H |
| CL-012 | $R_{114}$ and $R_{115}$ together form pyrrolidin-1-yl | | H |
| CL-013 | 2-methoxyethyl | H | H |
| CL-014 | 2-methoxyphenyl | H | H |
| CL-015 | 3-chlorophenyl | H | H |
| CL-016 | 4-fluorobenzyl | H | H |
| CL-017 | H | H | H |
| CL-018 | CH$_3$ | H | H |
| CL-019 | CH$_3$ | CH$_3$ | H |
| CL-020 | isopropyl | H | H |

TABLE 9

(XIV)

[Structure: oxindole with R117, R118, R119 on benzene ring and methylene-linked indole with R120, NH]

| Compound Number | R₁₁₇ | R₁₁₈ | R₁₁₉ | R₁₂₀ |
| --- | --- | --- | --- | --- |
| CL-021 | H | Br | H | 2-Diethylamino-ethoxy |
| CL-022 | H | H | 3-Methoxy-phenyl | 2-Diethylamino-ethoxy |
| CL-023 | H | H | 4-Methoxy-phenyl | 2-Diethylamino-ethoxy |
| CL-024 | H | H | Phenyl | 2-Diethylamino-ethoxy |
| CL-025 | H | H | 2-Methoxy-phenyl | 2-Diethylamino-ethoxy |
| CL-026 | [ethyl-NH-C(=O)-] | H | H | 2-Diethylamino-ethoxy |
| CL-027 | H | H | Br | 2-Diethylamino-ethoxy |
| CL-028 | H | H | Pyridin-3-yl | 2-Diethylamino-ethoxy |
| CL-029 | H | Phenyl | H | 2-Diethylamino-ethoxy |
| CL-030 | [3-chloro-4-methoxyphenyl-NH-C(=O)-] | H | H | 2-Diethylamino-ethoxy |
| CL-031 | H | —COOH | H | 3-Pyrrolidin-1-yl-propyl |
| CL-032 | H | H | —COOH | 3-Pyrrolidin-1-yl-propyl |
| CL-033 | H | [HOOC-CH₂-NH-C(=O)-] | H | 3-Pyrrolidin-1-yl-propyl |
| CL-034 | H | H | [HOOC-CH₂-NH-C(=O)-] | 3-Pyrrolidin-1-yl-propyl |
| CL-035 | H | [HOOC-CH(CH₃)-NH-C(=O)-] | H | 3-Pyrrolidin-1-yl-propyl |

TABLE 9-continued (XIV)

| Compound Number | $R_{117}$ | $R_{118}$ | $R_{119}$ | $R_{120}$ |
|---|---|---|---|---|
| CL-036 | H |  |  | 3-pyrrolidin-1-yl-propyl |
| CL-037 | H | H |  | 3-Pyrrolidin-1-yl-propyl |
| CL-038 | H | H |  | 3-Pyrrolidin-1-yl-propyl |

In another aspect, the invention relates to a method of synthesizing a compound of formula I, II, or VI, which method comprises reacting an oxindole having the structure set forth in formula XV, XVI, or XVII, with an aldehyde or a ketone, having a structure set forth in formula XVIII, XIX, or XX. $R_1$–$R_{16}$, $R_4$1-$R_{46}$, and A in formulae XV–XX are as defined herein.

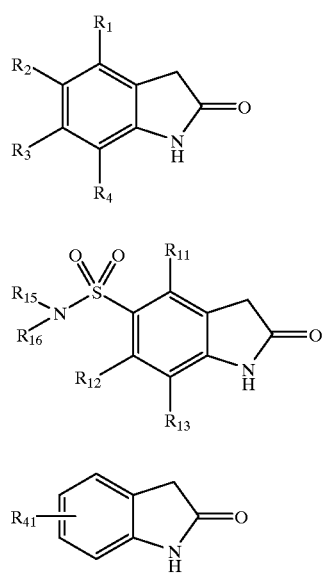

(XV)

(XVI)

(XVII)

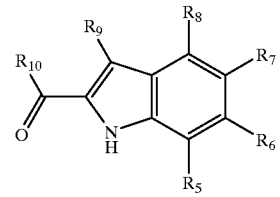

(XVIII)

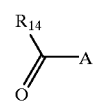

(XIX)

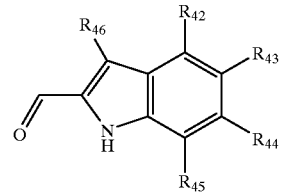

(XX)

The aldehyde of formula XX may be synthesized from the corresponding carboxylic acid or ester using the following reaction scheme.

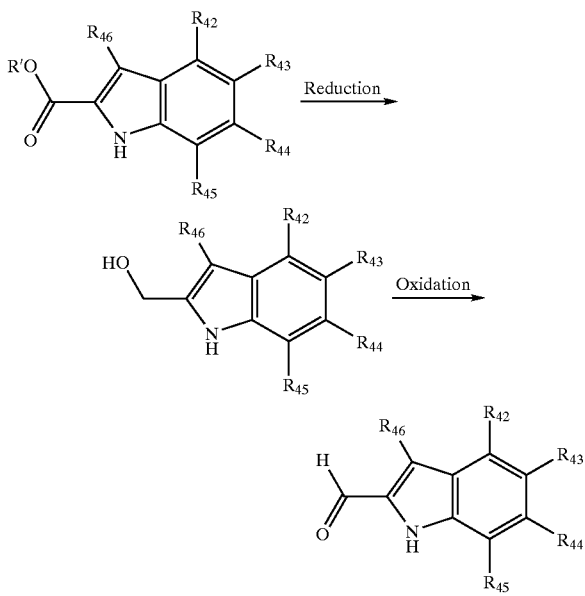

R' is hydrogen or alkyl, as defined herein.

To synthesize the compounds of the invention using the above methods a base may be used. The base is preferably a nitrogen base, an organic base, or an inorganic base. "Nitrogen bases" are commonly used in the art and are selected from acyclic and cyclic amines. Examples of nitrogen bases include, but are not limited to, ammonia, methylamine, trimethylamine, triethylamine, aniline, 1,8-diazabicyclo[5.4.0]undec-7-ene, diisopropylethylamine, pyrrolidine, and piperidine. "Organic bases" are bases that contain carbon atoms. Examples of organic bases include, but are not limited to, carbonate, bicarbonate, acetate, and formate anions. "Inorganic bases" are bases that do not contain any carbon atoms. Examples of inorganic bases include, but are not limited to, hydroxide, phosphate, bisulfate, hydrosulfide, and amide anions. Those skilled in the art know which nitrogen base or inorganic base would match the requirements of the reaction conditions. In certain embodiments of the invention, the base used may be pyrrolidine or piperidine. In other embodiments the base may be the hydroxide anion, preferably used as its sodium or potassium salt.

The synthesis of the compounds of the invention takes place in a solvent. The solvent of the reaction is preferably a protic solvent or an aprotic solevent. "Protic solvents" are those that are capable of donating a proton to a solute. Examples of protic solvents include, but are not limited to, alcohols and water. "Aprotic solvents" are those solvents that, under normal reaction conditions, do not donate a proton to a solute. Typical organic solvents, such as hexane, toluene, benzene, methylene chloride, dimethylformamide, dimethylsulfoxide, chloroform, tetrahydrofuran, are some of the examples of aprotic solvents. Other aprotic solvents are also within the scope of use by the present invention. In some preferred embodiments, the solvent of the reaction is an alcohol, which may preferably be isopropanol or most preferably ethanol. Water is another preferred protic solvent. Dimethylformamide, known in the chemistry art as DMF, and dimethylsulfoxide, known in the chemistry art as DMSO, are preferred aprotic solvents.

The synthetic method of the invention calls for the reaction to take place at elevated temperatures which are temperatures that are greater than room temperature. More preferably, the elevated temperature is preferably about 30–150° C., more preferably is about 70–100° C., and most preferably is about 70–90° C., which is about the temperature at which ethanol boils (i.e., the boiling point of ethanol). By "about" a certain temperature it is meant that the temperature range is preferably within 10° C. of the listed temperature, more preferably within 5° C. of the listed temperature, and most preferably within 2° C. of the listed temperature. Therefore, by way of example, by "about 80° C." it is meant that the temperature range is preferably 80±10° C., more preferably 80±5° C., and most preferably 80±2 ° C.

The synthetic method of the invention may be accompanied by the step of screening a library for a compound of the desired activity and structure—thus, providing a method of synthesis of a compound by first screening for a compound having the desired properties and then chemically synthesizing that compound.

In another aspect, the invention features a pharmaceutical composition comprising (i) a physiologically acceptable carrier, diluent, or excipient; and (ii) an indolinone compound of the invention, as described herein. It is understood that the indolinone compound of the invention may be one of formula I, II, or VI, or a compound obtained from the combinatorial library of the invention.

The term "pharmaceutical composition" refers to a mixture of an indolinone compound of the invention with other pharmaceutically acceptable diluents, excipients, or carriers. The pharmaceutical composition facilitates administration of the compound to an organism. Pharmaceutical compositions can be obtained by reacting compounds with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "pharmaceutically acceptable" defines a carrier or diluent that does not abrogate the biological activity and properties of the compound.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The invention also features a method of modulating the function of a PK or a protein phosphatase (PP) with an indolinone compound of the invention, comprising the step of contacting cells expressing the PK or a PP with the compound. It is understood that the indolinone compound of the invention may be one of formula I, II, or VI, or a compound obtained from the combinatorial library of the invention.

The term "function" refers to the cellular role of PKs or PPs. These proteins include members that regulate many steps in signaling cascades, including cascades controlling cell growth, migration, differentiation, gene expression, muscle contraction, glucose metabolism, cellular protein synthesis, and regulation of the cell cycle.

The term "catalytic activity", in the context of the invention, defines the rate at which a protein kinase phosphorylates a substrate or a protein phosphatase dephosphorylates a substrate. Catalytic activity can be measured, for example, by determining the amount of a substrate converted to a product as a function of time. Phosphorylation or dephosphastase of a substrate occurs at the active-site of a protein kinase. The active-site is normally a cavity in which the substrate binds to the protein kinase or phosphatase and is connected to the product.

The term "substrate" as used herein refers to a molecule phosphorylated by a PK or dephosphorylated by a PP. The substrate is preferably a peptide and more preferably a protein.

The term "activates" refers to increasing the cellular function of a PK or PP. This function is preferably the interaction with a natural binding partner and most preferably catalytic activity.

The term "inhibit" refers to decreasing the cellular function of a PK or PP. The PK or PP function is preferably the interaction with a natural binding partner and most preferably catalytic activity.

The term "modulates" refers to altering the function of a protein kinase by increasing or decreasing the probability that a complex forms between a protein kinase and a natural binding partner. A modulator preferably increases the probability that such a complex forms between the PK or PP and the natural binding partner, more preferably increases or decreases the probability that a complex forms between the PK or PP and the natural binding partner depending on the concentration of the compound exposed to the PK or PP, and most preferably decreases the probability that a complex forms between the PK or PP and the natural binding partner. A modulator preferably activates the catalytic activity of a PK or PP, more preferably activates or inhibits the catalytic activity of a PK or PP depending on the concentration of the compound exposed to the PK or PP, or most preferably inhibits the catalytic activity of a PK or PP.

The term "complex" refers to an assembly of at least two molecules bound to one another. Signal transduction complexes often contain at least two protein molecules bound to one another.

The term "natural binding partner" refers to polypeptides that bind to a PK or PP in cells. Natural binding partners can play a role in propagating a signal in a PK or PP signal transduction process. A change in the interaction between a PK or PP and a natural binding partner can manifest itself as an increased or decreased probability that the interaction forms, or an increased or decreased concentration of the PK or PP/natural binding partner complex.

A PK or PP natural binding partner can bind to a PK's or PP's intracellular region with high affinity. High affinity represents an equilibrium binding constant on the order of $10^{-6}$ M or less. In addition, a natural binding partner can also transiently interact with a protein kinase intracellular region and chemically modify it. PK or PP natural binding partners are chosen from a group that includes, but is not limited to, SRC homology 2 (SH2) or 3 (SH3) domains, other phosphoryl tyrosine binding (PTB) domains, guanine nucleotide exchange factors, protein phosphatases, and other protein kinases. Methods of determining changes in interactions between PK or PP and their natural binding partners are readily available in the art.

The term "contacting" as used herein refers to mixing a solution comprising an indolinone compound of the invention with a liquid medium bathing the cells of the methods. The solution comprising the compound may also comprise another component, such as dimethylsulfoxide (DMSO), which facilitates the uptake of the indolinone compound or compounds into the cells of the methods. The solution comprising the indolinone compound may be added to the medium bathing the cells by utilizing a delivery apparatus, such as a pipet-based device or syringe-based device.

The indolinone compounds of the invention preferably modulate the activity of the PK or PP in vitro. These compounds preferably show positive results in one or more in vitro assays for an activity corresponding to treatment of the disease or disorder in question (such as the assays described in the Examples below). It is understood that the indolinone compound of the invention may be one of formula I, II, or VI, or a compound obtained from the combinatorial library of the invention.

The invention also features a method of identifying indolinone compounds that modulate the function of PK or PP, comprising the following steps: (a) contacting cells expressing the PK or PP with the compound; and (b) monitoring an effect upon the cells. The effect upon the cells is preferably a change or an absence of a change in cell phenotype, more preferably it is a change or an absence of a change in cell proliferation, even more preferably it is a change or absence of a change in the catalytic activity of the PK or PP, and most preferably it is a change or absence of a change in the interaction between the PK or PP with a natural binding partner, as described herein. It is understood that the indolinone compound of the invention may be one of formula I, II, or VI, or a compound obtained from the combinatorial library of the invention.

The term "monitoring" refers to observing the effect of adding the compound to the cells of the method. The effect can be manifested in a change in cell phenotype, cell proliferation, PK or PP catalytic activity, or in the interaction between a PK or PP and a natural binding partner.

The term "effect" describes a change or an absence of a change in cell phenotype or cell proliferation. "Effect" can also describe a change or an absence of a change in the catalytic activity of the pro PK or PP. "Effect" can also describe a change or an absence of a change in an interaction between the PK or PP and a natural binding partner.

The term "cell phenotype" refers to the outward appearance of a cell or tissue or the function of the cell or tissue. Examples of cell phenotype are cell size (reduction or enlargement), cell proliferation (increased or decreased numbers of cells), cell differentiation (a change or absence of a change in cell shape), cell survival, apoptosis (cell death), or the utilization of a metabolic nutrient (e.g., glucose uptake). Changes or the absence of changes in cell phenotype are readily measured by techniques known in the art.

In a preferred embodiment, the invention features a method for identifying other compounds capable of modulating the activity of PK or PP using the indolinones of the invention as a reference which method comprises the following steps: (a) lysing the cells to render a lysate comprising PK or PP; (b) adsorbing the PK or PP to an antibody; (c) incubating the adsorbed PK or PP with a substrate or substrates in the presence or absence of test compound or an indolinone compound of the present invention; and (d) adsorbing the substrate or substrates to a solid support or antibody the effect upon the cells is then monitored and the step of monitoring the effect on the cells comprises measuring the phosphate concentration of the substrate or substrates. It is understood that the indolinone compound of the invention may be one of formula I, II, or VI, or a compound obtained from the combinatorial library of the invention.

The term "antibody" refers to an antibody (e.g., a monoclonal or polyclonal antibody), or antibody fragment, having specific binding affinity to PK or PP or its fragment.

By "specific binding affinity" is meant that the antibody binds to target (PK or PP) polypeptides with greater affinity than it binds to other polypeptides under specified conditions. Antibodies having specific binding affinity to a PK or PP may be used in methods for detecting the presence and/or amount of a PK or PP in a sample by contacting the sample with the antibody under conditions such that an immunocomplex forms and detecting the presence and/or amount of the antibody conjugated to the PK or PP. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

The term "polyclonal" refers to antibodies that are heterogenous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, for example, Kohler, et al., *Nature* 256:495–497 (1975), and U.S. Pat. No. 4,376,110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

In yet another aspect, the invention features a method for treating a disease related to unregulated tyrosine kinase or phosphatase signal transduction, where the method includes the step of administering to a subject in need thereof a therapeutically effective amount of an indolinone compound as described herein. It is understood that the indolinone compound of the invention may be one of formula I, II, or VI, or a compound obtained from the combinatorial library of the invention.

The term "treating" or "treatment" does not necessarily mean total cure. Any alleviation of any undesired symptom of the disease to any extent or the slowing down of the progress of the disease can be considered treatment. Furthermore, treatment may include acts which may worsen the patient's overall feeling of well being or appearance. For example, the administration of chemotherapy in cancer patients which may leave the patients feeling "sicker" is still considered treatment.

The invention also features a method of regulating tyrosine kinase or phosphatase signal transduction comprising administering to a subject a therapeutically effective amount of an indolinone compound as described herein. It is understood that the indolinone compound of the invention may be one of formula I, II, or VI, or a compound obtained from the combinatorial library of the invention.

Furthermore, the invention features a method of preventing or treating an abnormal condition in an organism, where the abnormal condition is associated with an aberration in a signal transduction pathway characterized by an interaction between a PK or PP and a natural binding partner, where the method comprises the following steps: (a) administering an indolinone compound as described herein; and (b) promoting or disrupting the abnormal interaction. The organism is preferably a mammal and the abnormal condition is preferably cancer. It is understood that the indolinone compound of the invention may be one of formula I, II, or VI, or a compound obtained from the combinatorial library of the invention. The abnormal condition may also preferably be selected from the group consisting of hypertension, depression, generalized anxiety disorder, phobias, post-traumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders, Parkinson's disease, endocrine disorders, vasospasm, cerebellar ataxia, and gastrointestinal tract disorders.

The term "aberration", in conjunction with a signal transduction process, refers to a PK or PP that is over- or under-expressed in an organism, mutated such that its catalytic activity is lower or higher than wild-type PK or PP activity, mutated such that it can no longer interact with a natural binding partner, is no longer modified by another protein kinase or protein phosphatase, or no longer interacts with a natural binding partner.

The term "promoting or disrupting the abnormal interaction" refers to a method that can be accomplished by administering a compound of the invention to cells or tissues in an organism. A compound can promote an interaction between a PK or PP and natural binding partners by, for example, forming favorable interactions with multiple atoms at the complex interface. Alternatively, a compound can inhibit an interaction between a PK or PP and natural binding partners by compromising favorable interactions formed between atoms at the complex interface.

The summary of the invention described above is non-limiting and other features and advantages of the invention will be apparent from the following description of the preferred embodiments, and from the claims.

Utility

The present invention relates to compounds capable of regulating and/or modulating PK or PP signal transduction and more particularly receptor and non-receptor tyrosine kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects to the extracellular microenvironment). See, Schlessinger and Ullrich, 1992, *Neuron* 9:303–391.

It has been shown that tyrosine phosphorylation sites in growth factor receptors function as high-affinity binding sites for SH2 (src homology) domains of signaling molecules. Fantl et al., 1992, *Cell* 69:413–423; Songyang et al, 1994, *Mol. Cell. Biol.* 14:2777–2785); Songyang et al., 1993, *Cell* 72:767–778; and Koch et al., 1991, *Science* 252:668–678. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. Songyang et al., 1993, Cell 72:767–778. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., 1993, Cell 72:767–778. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis).

This invention is therefore directed to compounds which regulate, modulate and/or inhibit tyrosine kinase signal transduction by affecting the enzymatic activity of the RTKs and/or the non-receptor tyrosine kinases and interfering with the signal transduced by such proteins. More particularly, the present invention is directed to compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers. The present invention is also directed to compounds used in a therapeutic approach to cure non-solid tumor cancers, such as, leukemia.

I. Target Diseases to be Treated by the Compounds of the Invention

The compounds described herein are useful for treating disorders related to unregulated tyrosine kinase signal transduction, including cell proliferative disorders, fibrotic disorders and metabolic disorders.

Cell proliferative disorders which can be treated or further studied by the present invention include cancers, blood vessel proliferative disorders and mesangial cell proliferative disorders.

Blood vessel proliferative disorders refer to angiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing and organ regeneration. They also play a pivotal role in cancer development. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness, and Von Hippel-Lindau (VHL) disease, which is an inherited multi-system disorder characterized by abnormal growth of blood vessels in certain parts of the body. Conversely, disorders related to the shrinkage, contraction or closing of blood vessels, such as restenosis, are also implicated.

Fibrotic disorders refer to the abnormal formation of extracellular matrix. Examples of fibrotic disorders include hepatic cirrhosis and mesangial cell proliferative disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis. Other fibrotic disorders implicated include atherosclerosis (see, below).

Mesangial cell proliferative disorders refer to disorders brought about by abnormal proliferation of mesangial cells. Mesangial proliferative disorders include various human renal diseases, such as glomerulonephritis, diabetic nephropathy, malignant nephrosclerosis, thrombotic microangiopathy syndromes, transplant rejection, and glomerulopathies. The PDGF-R has been implicated in the maintenance of mesangial cell proliferation. Floege et al., 1993, Kidney International 43:47S–54S.

PKs have been associated with such cell proliferative disorders. For example, some members of the RTK family have been associated with the development of cancer. Some of these receptors, like the EGFR (Tuzi et al., 1991, Br. J Cancer 63:227–233; Torp et al., 1992, APMIS 100:713–719) HER2/neu (Slamon et al, 1989, Science 244:707–712) and the PDGF-R (Kumabe et al., 1992, Oncogene 7:627–633) are overexpressed in many tumors and/or persistently activated by autocrine loops. In fact, in the most common and severe cancers these receptor overexpressions (Akbasak and Suner-Akbasak et al., 1992, J. Neurol. Sci. 111:119–133; Dickson et al., 1992, Cancer Treatment Res. 61:249–273; Korc et al., 1992, J. Clin. Invest. 90:1352–1360) and autocrine loops (Lee and Donoghue, 1992, J. Cell. Biol. 118:1057–1070; Korc et al., supra; Akbasak and Suner-Akbasak et al., supra) have been demonstrated. For example, the EGFR receptor has been associated with squamous cell carcinoma, astrocytoma, glioblastoma, head and neck cancer, lung cancer and bladder cancer. HER2 has been associated with breast, ovarian, gastric, lung, pancreas and bladder cancer. The PDGF-R has been associated with glioblastoma, lung, ovarian, melanoma and prostate cancer. The RTK c-met has been generally associated with hepatocarcinogenesis and thus hepatocellular carcinoma. Additionally, c-met has been linked to malignant tumor formation. More specifically, the RTK c-met has been associated with, among other cancers, colorectal, thyroid, pancreatic and gastric carcinoma, leukemia and lymphoma. Additionally, over-expression of the c-met gene has been detected in patients with Hodgkin's disease, Burkitt's disease, and the lymphoma cell line.

The IGF-IR, in addition to being implicated in nutritional support and in type-II diabetes, has also been associated with several types of cancers. For example, IGF-I has been implicated as an autocrine growth stimulator for several tumor types, e.g., human breast cancer carcinoma cells (Arteaga et al., 1989, J. Clin. Invest. 84:1418–1423) and small lung tumor cells (Macauley et al., 1990, Cancer Res. 50:2511–2517). In addition, IGF-I, integrally involved in the normal growth and differentiation of the nervous system, appears to be an autocrine stimulator of human gliomas. Sandberg-Nordqvist et al., 1993, Cancer Res. 53:2475–2478. The importance of the IGF-IR and its ligands in cell proliferation is further supported by the fact that many cell types in culture (fibroblasts, epithelial cells, smooth muscle cells, T-lymphocytes, myeloid cells, chondrocytes, osteoblasts, the stem cells of the bone marrow) are stimulated to grow by IGF-I. Goldring and Goldring, 1991, *Eukaryotic Gene Expression* 1:301–326. In a series of recent publications, Baserga even suggests that IGF-I-R plays a central role in the mechanisms of transformation and, as such, could be a preferred target for therapeutic interventions for a broad spectrum of human malignancies. Baserga, 1995, *Cancer Res.* 55:249–252; Baserga, 1994, *Cell* 79:927–930; Coppola et al., 1994, *Mol. Cell. Biol.* 14:4588–4595.

The association between abnormalities in RTKs and disease are not restricted to cancer, however. For example, RTKs have been associated with metabolic diseases like psoriasis, diabetes mellitus, wound healing, inflammation, and neurodegenerative diseases. These diseases include, but are not limited to hypertension, depression, generalized anxiety disorder, phobias, post-traumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders, Parkinson's disease, endocrine disorders, vasospasm, cerebellar ataxia, and gastrointestinal tract disorders. For example, the EGF-R is indicated in corneal and dermal wound healing. Defects in the Insulin-R and the IGF-IR are indicated in type-II diabetes mellitus. A more complete correlation between specific RTKs and their therapeutic indications is set forth in Plowman et al., 1994, *DN&P* 7:334–339.

Not only receptor type tyrosine kinases, but also many cellular tyrosine kinases (CTKs) including src, abl, fps, yes, fyn, lyn, lck, blk, hck, fgr, yrk (reviewed by Bolen et al., 1992, *FASEB J.* 6:3403–3409) are involved in the proliferative and metabolic signal transduction pathway and thus in indications of the present invention. For example, mutated src (v-src) has been demonstrated as an oncoprotein ($pp60^{v-src}$) in chicken. Moreover, its cellular homolog, the proto-oncogene $pp60^{c-src}$ transmits oncogenic signals of many receptors. For example, overexpression of EGF-R or HER2/neu in tumors leads to the constitutive activation of $pp60^{c-src}$, which is characteristic for the malignant cell but absent from the normal cell. On the other hand, mice deficient for the expression of c-src exhibit an osteopetrotic phenotype, indicating a key participation of c-src in osteoclast function and a possible involvement in related disorders. Similarly, Zap-70 is implicated in T-cell signaling.

Furthermore, the identification of CTK modulating compounds to augment or even synergize with RTK aimed blockers is an aspect of the present invention.

Finally, both RTKs and non-receptor type kinases have been connected to hyperimmune disorders.

The compounds of the present invention are also effective in treating diseases that are related to the PYK-2 protein. This protein, its cellular function, and diseases related to them are set forth in detail in U.S. Pat. No. 5,837,524, issued Nov. 17, 1998, by Lev et al., and entitled "PYK2 RELATED PRODUCTS AND METHODS" (Lyon & Lyon Docket No. 209/070), U.S. Pat. No. 5,837,815, issued Nov. 17, 1998, by Lev et al., and entitled "PYK2 RELATED PRODUCTS AND METHODS" (Lyon & Lyon Docket No. 211/121), U.S. patent application Ser. No. 08/987,689, filed Dec. 9, 1997, by Lev et al., and entitled "PYK2 RELATED PRODUCTS AND METHODS" (Lyon & Lyon Docket No. 230/110), U.S. patent application Ser. No. 09/165,062, filed Oct. 1, 1998, by Lev et al., and entitled "PYK2 RELATED PRODUCTS AND METHODS" (Lyon & Lyon Docket No. 237/201), International Publication Number WO98/26054, published Jun. 18, 1998, by Lev et al., and entitled "PYK2 RELATED PRODUCTS AND METHODS" (Lyon & Lyon Docket No. 222/126), and International Application Number US 98/27871, filed Dec. 31, 1998, by Schlessinger et al., and entitled "PYK2 AND INFLAMMATION" (Lyon & Lyon Docket No. 236/075), all of which are hereby incorporated by reference herein in their entirety, including any drawings.

In addition, some of the compounds of the present invention are effective against rhematoid arthritis (RA). RA is a chronic inflammatory disease mediated by multiple cell types and cellular processes. Included in these are the infiltration of macrophages and T cells, and the involvement of angiogenesis. The utility of small molecule inhibitors for the treatment of RA was investigated in a rat collagen induced arthritis model. Some of the compounds of the present invention inhibit the tyrosine kinases Flk-1/KDR, pyk2, and ZAP-70 to varying degrees in biochemical kinase assays. In addition, the compounds are active in cellular assays targeted to cells implicated in the pathogenesis of RA: inhibition of T cell proliferation mediated by ZAP-70 activity, inhibition of VEGF stimulated HUVEC proliferation mediated by Flk-1/KDR activation, and inhibition of TNF-α production from murine bone marrow derived macrophages mediated by pyk2 activation. Finally, in arodent collagen induced arthritis model, which mimics the histological and pathological changes associated with human RA, some of the compounds of the invention are efficacious in inhibiting joint swelling when dosed daily from the time of collagen immunization.

II. The KDR/FLK-1 Receptor and VEGF

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman and Shing, 1992, *J. Biological Chem.* 267:10931–34. However, many diseases are driven by persistent unregulated or inappropriate angiogenesis. For example, in arthritis, new capillary blood vessels invade the joint and destroy the cartilage. In diabetes, new capillaries in the retina invade the vitreous, bleed and cause blindness. Folkman, 1987, in: *Congress of Thrombosis and Haemostasis* (Verstraete, et. al, eds.), Leuven University Press, Leuven, pp. 583–596. Ocular neovascularization is the most common cause of blindness and dominates approximately twenty (20) eye diseases.

Moreover, vasculogenesis and/or angiogenesis have been associated with the growth of malignant solid tumors and metastasis. A tumor must continuously stimulate the growth of new capillary blood vessels for the tumor itself to grow. Furthermore, the new blood vessels embedded in a tumor provide a gateway for tumor cells to enter the circulation and to metastasize to distant sites in the body. Folkman, 1990, *J. Natl. Cancer Inst.* 82:4–6; Klagsbrunn and Soker, 1993, *Current Biology* 3:699–702; Folkman, 1991, *J. Natl., Cancer Inst.* 82:4–6; Weidner et al., 1991, *New Engl. J. Med.* 324:1–5.

Several polypeptides with in vitro endothelial cell growth promoting activity have been identified. Examples include acidic and basic fibroblastic growth factor (aFGF, bFGF), vascular endothelial growth factor (VEGF) and placental growth factor. Unlike aFGF and bFGF, VEGF has recently been reported to be an endothelial cell specific mitogen. Ferrara and Henzel, 1989, *Biochem. Biophys. Res. Comm.* 161:851–858; Vaisman et al, 1990, *J. Biol. Chem.* 265:19461–19566.

Thus, the identification of the specific receptors to which VEGF binds is an important advancement in the understanding of the regulation of endothelial cell proliferation. Two structurally closely related RTKs have been identified to bind VEGF with high affinity: the fit-i receptor (Shibuya et al., 1990, *Oncogene* 5:519–524; De Vries et al., 1992, *Science* 255:989–991) and the KDR/FLK-1 receptor, (also referred to as VEGFR2) discussed in the U.S. patent application Ser. Nos. 08/193,829 and 08/965,598. Consequently, it had been surmised that these RTKs may have a role in the modulation and regulation of endothelial cell proliferation.

Evidence, such as the disclosure set forth in copending U.S. application Ser. Nos. 08/193,829 and 08/965,598, strongly suggests that VEGF is not only responsible for endothelial cell proliferation, but also is a prime regulator of normal and pathological angiogenesis. See generally, Klagsbum and Soker, 1993, *Current Biology* 3:699–702; Houck et al., 1992, *J. Biol. Chem.* 267:26031–26037. Moreover, it has been shown that KDR/FLK-1 and fit-1 are abundantly expressed in the proliferating endothelial cells of a growing tumor, but not in the surrounding quiescent endothelial cells. Plate et al., 1992, *Nature* 359:845–848; Shweiki et al., 1992, *Nature* 359:843–845.

III. Identification of Agonists and Antagonists to the KDR/FLK-1 Receptor

In view of the deduced importance of RTKs in the control, regulation and modulation of endothelial cell proliferation and potentially vasculogenesis and/or angiogenesis, many attempts have been made to identify RTK "inhibitors" using a variety of approaches. These include the use of mutant ligands (U.S. Pat. No. 4,966,849); soluble receptors and antibodies (International Publication No. WO 94/10202; Kendall and Thomas, 1994, *Proc. Natl. Acad. Sci. USA* 90:10705–10709; Kim et al., 1993, *Nature* 362:841–844); and RNA ligands (Jellinek et al., 1994, *Biochemistry* 33:10450–10456).

Furthermore, tyrosine kinase inhibitors (WO 94/03427; WO 92/21660; WO 91/15495; WO 94/14808; U.S. Pat. No. 5,330,992; Mariani et al., 1994, *Proc. Am. Assoc. Cancer Res.* 35:2268), and inhibitors acting on receptor tyrosine kinase signal transduction pathways, such as protein kinase C inhibitors have been identified (Schuchter et al., 1991, *Cancer Res.* 51:682–687); Takano et al., 1993, *Mol. Bio. Cell* 4:358A; Kinsella et al., 1992, *Exp. Cell Res.* 199:56–62; Wright et al., 1992, *J. Cellular Phys.* 152:448–57).

More recently, attempts have been made to identify small molecules which act as tyrosine kinase inhibitors. For example, bis monocyclic, bicyclic or heterocyclic aryl compounds (PCT WO 92/20642), vinylene-azaindole derivatives (PCT WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer.

Consequently, there is an unmet need for the identification and generation of effective small compounds which selectively inhibit the signal transduction of the KDR/FLK-1 receptor in order to effectively and specifically suppress vasculogenesis.

Some of the compounds of the present invention demonstrate excellent activity in biological assays and thus these compounds and related compounds are expected to be effective in treating Flk related disorders such as those driven by persistent unregulated or inappropriate angiogenesis.

Pharmaceutical Formulations and Routes of Administration

The compounds described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., latest edition.

1. Routes of Administration

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

2. Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant Polysorbate 80™, and 65% w/v polyethylene glycol-300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the PK modulating compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

3. Effective Dosage

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

For any compound used in the methods of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the PK activity). Such information can be used to more accurately determine useful doses in humans.

Toxicity and therapeutic efficacy of the compounds described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p.1).

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g., the concentration necessary to achieve 50–90% inhibition of the kinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

4. Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the polynucleotide for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

IV. Biological Activity of the Indolinone Compounds of the Invention

Some of the indolinone compounds of the present invention were tested for their ability to inhibit most of protein tyrosine kinase activity. The biological assays and results of these inhibition studies are reported herein. The methods used to measure indolinone compound modulation of protein kinase function are similar to those described in International Publication No. WO 98/07695, published Mar. 26, 1998, by Tang et al., and entitled "Indolinone Combinatorial Libraries and Related Products and Methods for the Treatment of Disease," with respect to the high throughput aspect of the method. The WO 98/07695 publication is incorporated herein by reference in its entirety, including any drawings.

V. Pharmaceutical Compositions and Administration of Indolinone Compounds of the Invention Methods of preparing pharmaceutical formulations of the compounds, methods of determining the amounts of compounds to be administered to a patient, and modes of administering compounds to an organism are disclosed in International Publication No. WO 98/07695, by Tang et al., and entitled "Indolinone Combinatorial Libraries and Related Products and Methods for the Treatment of Disease," and International Publication No. WO 96/22976, by Buzzetti et al., and entitled "Hydrosoluble 3-Arylidene-2-Oxindole Derivatives as Tyrosine Kinase Inhibitors," published Aug. 1, 1996, both of which are incorporated herein by reference in their entirety, including any drawings. Those skilled in the art will appreciate that such descriptions are applicable to the present invention and can be easily adapted to it.

EXAMPLES

The examples below are non-limiting and are merely representative of various aspects and features of the present invention. The examples describe methods for synthesizing compounds of the invention and methods for measuring an effect of a compound on the function of protein tyrosine kinases.

The cells used in the methods are commercially available. The nucleic acid vectors harbored by the cells are also commercially available and the sequences of genes for the various protein kinases are readily accessible in sequence data banks. Thus, a person of ordinary skill in the art can readily recreate the cell lines in a timely manner by combining the commercially available cells, the commercially available nucleic acid vectors, and the protein kinase genes using techniques readily available to persons of ordinary skill in the art.

Synthetic Procedures

The following examples describe methods of synthesizing some of the compounds of the invention.

Example 1

Preparation of 5-(2-dimethylamino-ethoxy)-1H-indole 2-carbaldehyde

A mixture of 5-hydroxy-1H-indole-2-carboxylic acid ethyl ester (2 g, 10 mmol), 2-chloro-N,N-dimethylacetamide (1.33 g, 11 mmol) and cesium carbonate (9.8 g, 30 mmol) ) in dimethylformamide (20 mL) was stirred at room temperature for 16 hours. The reaction was diluted with ethyl acetate (150 mL), washed with water (5×50 mL) and brine, dried and concentrated. The residue was recrystallized from ethyl acetate and hexane to give 1.4 g of 5-dimethylcarbamoylmethoxy-1H-indole-2-carboxylic acid ethyl ester as a brown solid.

$^1$HNMR (300 MHz, DMSO-$d_6$) δ11.74 (s, br, 1H, NH), 7.33 (d, J=9.0 Hz, 1H, H-7), 7.06 (d, J=2.4 Hz, 1H, H-4), 7.01 (d, J=1.5 Hz, 1H, H-3), 6.94 (dd, J=2.4 & 9.0 Hz, 1H, H-6), 4.74 (s, 2H, OC$\underline{H}_2$CON(CH$_3$)$_2$, 4.31 (q, J=7.1 Hz, 2H, OC$\underline{H}_2$CH$_3$), 3.0 (s, 3H, NCH$_3$), 2.83 (s, 3H, NCH$_3$), 1.32 (t, J=7.1 Hz, 3H, OCH$_2$C$\underline{H}_3$).

MS-EI m/z 290 [M$^+$].

Lithium aluminum hydride (1.7 g, 45 mmol) was added to 5-dimethylcarbamoylmethoxy-1H-indole-2-carboxylic acid ethyl ester (1.4 g, 4.8 mmol) in tetrahydrofuran (80 mL). The mixture was stirred at room temperature for 4 hours and cooled to 0° C. It was then quenched with water (1.7 mL), 15% sodium hydroxide (1.7 mL) and water (1.7 mL). The precipitate was filtered off and the filtrate was concentrated to give 0.6 g (54%) of [5-(2-dimethylamino-ethoxy)-1H-indol-2-yl]-methanol.

$^1$HNMR (300 MHz, DMSO-$d_6$) δ10.79 (s, br, 1H, NH), 7.17 (d, J=8.9 Hz, 1H, H-7), 6.95 (d, J=2.1 Hz, 1H, H-4), 6.64 (dd, J=2.1 & 8.9 Hz, 1H, H-6), 6.61 (d, J=1.5 Hz, 1H, H-3), 5.18 (d, J=5.5 Hz, 1H, CH$_2$O$\underline{H}$), 4.54 (d, J=5.5 Hz, 2H, C$\underline{H}_2$OH), 3.98 (t, J=6.0 Hz, 2H, OC$\underline{H}_2$CH$_2$N), 2.59 (t, J=6.0 Hz, 2H, OCH$_2$C$\underline{H}_2$N), 2.20 (s, 6H, N(CH$_3$)$_2$).

MS-EI m/z 234 [M$^+$].

Manganese (IV) oxide (3.3 g, 38 mmol) was added to 5-(2-dimethylamino-ethoxy)-1H-indol-2-yl]-methanol (0.6 g, 2.5 mmol) in dichloromethane (100 mL). The mixture was stirred at room temperature for 16 hours. The precipitate was filtered off and the filtrate was concentrated to give 0.41 g (71%) of 5-(2-dimethylamino-ethoxy)-1H-indole-2-carbaldehyde.

$^1$HNMR (360 MHz, DMSO-$d_6$) δ11.78 (s, br, 1H, NH), 9.78 (s, 1H, CHO), 7.34 (d, J=8.8 Hz, 1H, H-7), 7.25 (d, J=1.1 Hz, 1H, H-3), 7.18 (d, J=2.3 Hz, 1H, H-4), 6.98 (dd, J=2.3 & 8.8 Hz, 1H, H-6), 4.04 (t, J=5.9 Hz, 2H, OC$\underline{H}_2$CH$_2$N), 2.63 (t, J=5.9 Hz, 2H, OCH$_2$C$\underline{H}_2$N), 2.22 (s, 6H, N(CH$_3$)$_2$).

MS m/z 233.2 [M$^+$+1].

Example 2

Preparation of 5-(2-pyrrolidin-1-yl-ethoxy)-1H-indole-2-carbaldehyde

A mixture of pyrrolidine (1.7 g, 24 mmol), bromoacetyl bromide (4.6 g, 24 mmol) and triethylamine (2.02 g, 20 mmol) in dichloromethane (40 mL) was stirred at room temperature for 4 hours. The precipitate was filtered off and the residue was concentrated to give 3.1 g of 2-bromo-1-pyrrolidin-1-yl-ethanone as a light brown solid.

$^1$HNMR (300 MHz, DMSO-$d_6$) δ4.03 (s, 2H, BrC$\underline{H}_2$CO), 3.45 (t, J=6.6 Hz, 2H), 3.27 (t, J=6.6 Hz,), 1.74–1.89 (m, 4H).

A mixture of 5-hydroxy-1H-indole-2-carboxylic acid ethyl ester (2 g, 10 mmol), 2-bromo-1-pyrrolidin-1-yl-ethanone (3 g, 20 mmol) and cesium carbonate (19.5 g, 60 mmol) in dimethylformamide (16 mL) was stirred at room temperature for 24 hours. The reaction was diluted with ethyl acetate (150 mL), washed with water (5×50 mL) and brine, dried and concentrated. The residue was recrystallized from ethyl acetate and hexane to give 0.8 g (25%) 5-(2-oxo-2-pyrrolidin-1-yl-ethoxy)-1H-indole-2-carboxylic acid ethyl ester as a brown solid.

$^1$HNMR (300 MHz, DMSO-$d_6$) δ11.74 (s, br, 1H, NH), 7.34 (d, J=8.7 Hz, 1H, H-7), 7.07 (d, J=2.5 Hz, 1H, H-4), 7.02 (d, J=1.5 Hz, 1H, H-3), 6.95 (dd, J=2.5 & 8.7 Hz, 1H, H-6), 4.67 (s, 2H, OC$\underline{H}_2$CON, 4.31 (q, J=7.1 Hz, 2H, OC$\underline{H}_2$CH$_3$), 3.47 (t, J=6.7 Hz, 2H), 3.31 (t, J=6.7 Hz, 2H), 1.88 (t, J=6.7 Hz, 2H), 1.76 (t, J=6.7 Hz, 2H), 1.32 (t, J=7.1 Hz, 3H, OCH$_2$C$\underline{H}_3$).

MS-EI m/z 316 [M$^+$].

Lithium aluminum hydride (0.4 g, 10 mmol) was added to 5-(2-oxo-2-pyrrolidin-1-yl-ethoxy)-1H-indole-2-carboxylic acid ethyl ester (0.6 g, 1.9 mmol) in tetrahydrofuran (120 mL). The mixture was stirred at room temperature for 16 hours and cooled to 0° C. It was then quenched with water (0.4 mL), 15% sodium hydroxide (0.4 mL) and water (0.4 mL). The precipitate was filtered off and the filtrate was concentrated to give 0.31 g (63%) of [5-(2-pyrrolidin-1-yl-ethoxy)-1H-indo-2-yl]-methanol as a white solid.

$^1$HNMR (360 MHz, DMSO-$d_6$) δ10.74 (s, br, 1H, NH), 7.17 (d, J=8.8 Hz, 1H, H-7), 6.94 (d, J=2.5 Hz, H-4), 6.65 (dd, J=2.5 & 8.8 Hz, 1H, H-6), 6.1 (d, J=0.7 Hz, H-3), 5.12 (d, J=5.5 Hz, 1H, CH$_2$O$\underline{H}$), 4.55 (d, J=5.5 Hz, 2H, C$\underline{H}_2$OH), 4.01 (t, J=6.0 Hz, 2H, OC$\underline{H}_2$CH$_2$N), 2.76 (t, J=6.0 Hz, 2H, OCH$_2$C$\underline{H}_2$N), 2.53 (m, under DMSO, H-pyrrolidine), 1.67 (m, 4H, H-pyrrolidine).

MS m/z 261.1 [M$^+$+1].

Manganese (IV) oxide (1 g, 12 mmol) was added to [5-(2-pyrrolidin-1-yl-ethoxy)-1H-indo-2-yl]-methanol (0.31 g, 1.2 mmol) in dichloromethane (100 mL). The mixture was stirred at room temperature for 4 hours. The precipitate was filtered off and the filtrate was concentrated to give 0.19 g (61%) of 5-(2-pyrrolidin-1-yl-ethoxy)-1H-indole-2-carbaldehyde.

$^1$HNMR (360 MHz, DMSO-$d_6$) δ11.78 (s, br, 1H, NH), 9.79 (s, 1H, CHO), 7.34 (d, J=9.0 Hz, 1H, H-7), 7.25 (d, J=1.1 Hz, 1H, H-3), 7.18 (d, J=2.4 Hz, 1H, H-4), 6.98 (dd, J=2.4 & 9.0 Hz, 1H, H-6), 4.06 (t, J=5.8 Hz, 2H, OC$\underline{H}_2$CH$_2$N), 2.79 (t, J=5.8 Hz, 2H, OCH$_2$C$\underline{H}_2$N), 2.52 (m, under DMSO, H-pyrrolidine), 1.67 (m, 4H, H-pyrrolidine).

MS-EI m/z 258 [M$^+$].

Example 3

Preparation of 5-(2-morpholin-4-yl-ethoxy)-1H-indole-2-carbaldehyde

A mixture of 5-hydroxy-1H-indole-2-carboxylic acid ethyl ester (2 g, 10 mmol), tert-butyl bromoacetate (2.35 g, 12 mmol) and cesium carbonate (10.5 g, 30 mmol) in dimethylformamide (10 mL) was stirred at room temperature for 16 hours. The reaction was diluted with ethyl acetate (150 mL), washed with water (5×50 mL) and brine, dried and concentrated. The residue was recrystallized from ethyl acetate and hexane to give 2 g (63%) 5-tert-butoxycarbonylmethoxy-1H-indole-2-carboxylic acid ethyl ester.

$^1$HNMR (360 MHz, DMSO-$d_6$) δ11.71 (s, br, 1H, NH), 7.34 (d, J=9.0 Hz, 1H, H-7), 7.02–7.03 (m, 2H, H-3 & 4), 6.93 (dd, J=2.3 & 9.0 Hz, 1H, H-6), 4.59 (s, 2H, OC$\underline{H}_2$CO, 4.31 (q, J=7.0 Hz, 2H, OC$\underline{H}_2$CH$_3$), 1.41 (s, 9H, C(CH$_3$)$_3$), 1.32 (t, J=7.0 Hz, 3H, OCH$_2$C$\underline{H}_3$).

MS-EI m/z 319 [M$^+$].

A mixture of 5-tert-butoxycarbonylmethoxy-1H-indole-2-carboxylic acid ethyl ester (2 g, 6 mmol) and trifluoroacetic acid (8 mL) in dichloromethane (8 mL) was stirred at room temperature for 2 hours. The reaction was concentrated to give 1.6 g (97%) of 5-carboxymethoxy-1H-indole-2-carboxylic acid ethyl ester as a light brown solid.

$^1$HNMR (360 MHz, DMSO-$d_6$) δ11.70 (s, br, 1H, NH), 7.35 (d, J=8.8 Hz, 1H, H-7), 7.04 (d, J=2.2 Hz, 1H, H-4), 7.02 (m, 1H, H-3), 6.94 (dd, J=2.2 & 8.8 Hz, 1H, H-6), 4.62 (s, 2H, OC$\underline{H}_2$CO, 4.31 (q, J=7.2 Hz, 2H, OC$\underline{H}_2$CH$_3$), 1.32 (t, J=7.2 Hz, 3H, OCH$_2$C$\underline{H}_3$).

MS-EI m/z 263 [M$^+$].

A mixture of 5-carboxymethoxy-1H-indole-2-carboxylic acid ethyl ester (1.5 g, 5.7 mmol) and 1-1'-carbonyldiimidazole (1.11 g, 6.85 mmol) in dimethylformamide (15 mL) was stirred at room temperature for 30 mins. To the mixture was then added morpholine (1 mL) and the stirring was continued for overnight. The reaction was concentrated and the residue was dissolved in dichloromethane (200 mL), washed with 1N hydrochloric acid, saturated sodium bicarbonate and brine, dried and concentrated to give 1.6 g (85%) of 5-(2-morpholin-4-yl-2-oxo-ethoxy)-1H-indole-2-carboxylic acid ethyl ester.

$^1$HNMR (360 MHz, DMSO-d$_6$) δ11.71 (s, br, 1H, NH), 7.35 (d, J=9.0 Hz, 1H, H-7), 7.10 (d, J=2.3 Hz, 1H, H-4), 7.02 (m, 1H, H-3), 6.95 (dd, J=2.3 & 9.0 Hz, 1H, H-6), 4.77 (s, 2H, OCH$_2$CO, 4.32 (q, J=7.2 Hz, 2H, OCH$_2$CH$_3$), 3.46–3.58 (m, 8H, 4×CH$_2$), 1.32 (t, J=7.2 Hz, 3H, OCH$_2$CH$_3$).

Lithium aluminum hydride (0.46 g, 12 mmol) was added-5-(2-morpholin-4-yl-2-oxo-ethoxy)-1H-indole-2-carboxylic acid ethyl ester (0.8 g, 2.4 mmol) in tetrahydrofuran (50 mL). The mixture was stirred at room temperature for 16 hours and cooled to 0° C. It was then quenched with water (4.6 mL), 15% sodium hydroxide (4.6 mL) and water (4.6 mL). The precipitate was filtered off and the filtrate was concentrated to give 0.7 g of [5-(2-morpholin-4-yl-ethoxy)-1H-indol-2-yl]-methanol.

$^1$HNMR (360 MHz, DMSO-d$_6$) δ10.74 (s, br, 1H, NH), 7.17 (d, J=8.6 Hz, 1H, H-7), 6.95 (m, 1H, H-4), 6.66 (m, 1H, H-6), 6.15 (s, 1H, H-3), 5.11 (d, J=5.4 Hz, 11H, CH$_2$OH), 4.55 (d, J=5.4 Hz, 2H, CH$_2$OH), 4.03 (t, J=5.7 Hz, 2H, OCH$_2$CH$_2$N), 3.56 (m, 4H, 2×CH$_2$), 2.67 (t, J=5.7 Hz, 2H, OCH$_2$CH$_2$N), 2.47 (m, under DMSO, 2×CH$_2$).

MS-EI m/z 276 [M$^+$+2].

Manganese (IV) oxide (3.2 g, 36 mmol) was added to [5-(2-morpholin-4-yl-ethoxy)-1H-indol-2-yl]-methanol (0.7 g) in dichloromethane (150 mL). The mixture was stirred at room temperature for 16 hours. The precipitate was filtered off and the filtrate was concentrated. The residue was recrystallized from ethyl acetate and hexane to give 0.18 g of 5-(2-morpholin-4-yl-ethoxy)-1H-indole-2-carbaldehyde.

$^1$HNMR (360 MHz, DMSO-d$_6$) δ11.78 (s, br, 1H, NH), 9.79 (s, 1H, CHO), 7.34 (d, J=9.2 Hz, 1H, H-7), 7.25 (m, 1H, H-3), 7.19 (d, J=1.8 Hz, 1H, H-4), 6.99 (dd, J=1.8 & 9.2 Hz, 1H, H-6), 4.08 (t, J=5.7 Hz, 2H, OCH$_2$CH$_2$N), 3.57 (m, 4H, 2×CH$_2$), 2.70 (t, J=5.7 Hz, 2H, OCH$_2$CH$_2$N), 2.48 (m, under DMSO, 2×CH$_2$).

Example 4
Preparation of 5-(2-diethylamino-ethoxy)-1H-indole-2-carbaldehyde

A mixture of 5-hydroxy-1H-indole-2-carboxylic acid ethyl ester (1 g, 5 mmol), 2-chloro-N,N-diethylacetamide (1 mL, 7.5 mmol) and cesium carbonate (5 g, 15 mmol) in dimethylformamide (10 mL) was stirred at room temperature for 6 hours. The reaction was diluted with ethyl acetate (160 mL), washed with water (5×50 mL) and brine, dried and concentrated. The residue was recrystallized from ethyl acetate and hexane to give 0.52 g of 5-diethylcarbamoylmethoxy-1H-indole-2-carboxylic acid ethyl ester as an off-white solid.

$^1$HNMR (360 MHz, DMSO-d$_6$) δ11.70 (s, br, 1H, NH), 7.34 (d, J=9.0 Hz, 1H, H-7), 7.08 (d, J=2.3 Hz, 1H, H-4), 7.02 (s, 1H, H-3), 6.94 (dd, J=2.3 & 9.0 Hz, 1H, H-6), 4.71 (s, 2H, OCH$_2$CON(CH$_2$CH$_3$)$_2$, 4.31 (q, J=7.2 Hz, 2H, OCH$_2$CH$_3$), 3.25–3.38 (m, 4H, N(CH$_2$CH$_3$)$_2$, 1.32 (t, J=7.2 Hz, 3H, OCH$_2$CH$_3$) 1.15 (t, J=7.0 Hz, 3H, NCH$_2$CH$_3$), 1.03 (t, J=7.0 Hz, 3H, NCH$_2$CHH$_3$)

MS-EI m/z 318 [M$^+$].

Lithium aluminum hydride (3.6 g, 45 mmol) was added to 5-dimethylcarbamoylmethoxy-1H-indole-2-carboxylic acid ethyl ester (0.52 g, 1.6 mmol) in tetrahydrofuran (80 mL). The mixture was stirred at room temperature for 16 hours and cooled to 0° C. It was then quenched with water (3.6 mL), 15% sodium hydroxide (3.6 mL) and water (3.6 mL). The precipitate was filtered off and the filtrate was concentrated to give 0.4 g (43%) of [5-(2-diethylamino-ethoxy)-1H-indol-2-yl]-methanol.

$^1$HNMR (300 MHz, DMSO-d$_6$) δ10.78 (s, br, 1H, NH), 7.16 (d, J=8.5 Hz, 1H, H-7), 6.94 (d, J=2.3 Hz, 1H, H-4), 6.64 (dd, J=2.3 & 8.5 Hz, 1H, H-6), 6.15 (d, J=1.2 Hz, 1H, H-3), 5.17 (t, J=5.6 Hz, 1H, CH$_2$OH), 4.54 (d, J=5.6 Hz, 2H, CH$_2$OH), 3.96 (t, J=6.3 Hz, 2H, OCH$_2$CH$_2$N), 2.75 (t, J=6.3 Hz, 2H, OCH$_2$CH$_2$N), 2.54 (q, J=7.1 Hz, 4H, 2×NCH$_2$CH$_3$), 0.96 (t, J=7.1 Hz, 6H, 2×NCH$_2$CH$_3$),

MS m/z 263.2 [M$^+$+1].

Manganese (IV) oxide (1.95 g, 23 mmol) was added to 5-(2-diethylamino-ethoxy)-1H-indol-2-yl]-methanol (0.4 g, 1.5 mmol) in dichloromethane (100 mL). The mixture was stirred at room temperature for 24 hours. The precipitate was filtered off and the filtrate was concentrated to give 0.31 g (79%) of 5-(2-diethylamino-ethoxy)-1H-indole-2-carbaldehyde.

$^1$HNMR (360 MHz, DMSO-d$_6$) δ11.78 (s, 1H, NH), 9.78 (s, 1H, CHO), 7.34 (d, J=9.0 Hz, 1H, H-7), 7.25 (d, J=1.4 Hz, 1H, H-3), 7.18 (d, J=2.4 Hz, 1H, H-4), 6.97 (dd, J=2.4 & 9.0 Hz, 1H, H-6), 4.01 (t, J=6.2 Hz, 2H, OCH$_2$CH$_2$N), 2.78 (t, J=6.2 Hz, 2H, OCH$_2$CH$_2$N), 2.55 (q, J=7.0 Hz, 4H, 2×NCH$_2$CH$_3$), 0.97 (t, J=7.0 Hz, 6H, 2×NCH$_2$CH$_3$).

MS-EI m/z 260 [M$^+$].

Example 5
Preparation of 5-(3-diethylamino-propyl-1H-indole-2-carbaldehyde

A mixture of 5-bromo-1H-indole-2-carboxylic acid ethyl ester (5.36 g, 20 mmol) in triethylamine (30 mL) and pyridine (6 mL) was degassed by bubbling nitrogen through for 10 minutes, followed by the addition of diethylpropargyl amine and the degassing was continued for another 5 minutes.

Dichlorobis(triphenylphosphine)palladium(II) (702 mg, 1 mmol) and copper (I) iodide (95 mg, 0.5 mmol) was added to the mixture and it was heated at 90° C. under nitrogen for 17 hours. The reaction was concentrated and the residue was partitioned between 1N HCl (150 mL) and ethyl acetate (300 mL). The layers were separated, the aqueous layer was extracted with another 300 mL of ethyl acetate. The combined organic layers were washed with brine, dried and concentrated to give 3.4 g (57%) of 5-(3-diethylamino-prop-1-ynyl)-1H-indole-2-carboxylic acid ethyl ester (hydrochloride salt) as a light brown crystalline solid.

$^1$HNMR (360 MHz, DMSO-d$_6$) δ12.14 (s, 1H, NH), 11.23 (s, br, 1H, NH), 7.89 (s, 1H, H-3), 7.49 (d, J=8.4 Hz, 1H, H-7), 7.36 (dd, J=1.4 & 8.4 Hz, 1H, H-6), 7.17 (d, J=1.4 Hz, 1H, H-4), 4.34 (q, J=7.1 Hz, 2H, OCH$_2$CH$_3$), 4.29 (s, CH$_2$), 3.16–3.24 (m, 4H, 2×NCH$_2$CH$_3$), 1.28–1.35 (9H, 3×CH$_3$).

MS-EI m/z 298 [M$^+$].

5-(3-Diethylamino-prop-1-ynyl)-1H-indole-2-carboxylic acid ethyl ester hydrochloride (2g, 6.7 mmol) was hydrogenated over palladium on carbon (10%) (713 mg, 0.67 mmol) under nitrogen for 5 hours. Palladium hydroxide on carbon (20%) (2×350 mg) and acetic acid (4 mL) were added to the mixture and continued to stir for another 12 hours. The reaction was filtered through celite and the filtrate was concentrated. The residue was partitioned between 1N HCl (150 mL) and ethyl acetate (300 mL). The aqueous layer was made basic to pH 8, extracted with ethyl acetate, washed with brine, dried and concentrated to give 1.126 g orange solid.

NMR spectrum of the above solid showed desired saturated compound and some alkene material. Therefore, the solid was dissolved in ethanol (10 mL) and acetic acid (7 mL) and it was hydrogenated over palladium hydroxide (175 mg) for 42 hours. Following the work-up as outlined above, 1.2 g (59%) of 5-(3-diethylamino-propyl)-1H-indole-2-carboxylic acid ethyl ester (acetate salt) was obtained.

$^1$HNMR (360 MHz, DMSO-d$_6$) δ11.70 (s, br, 1H, NH), 7.42 (s, 1H, H-3), 7.35 (d, J=8.5 Hz, 1H, H-7), 7.11 (dd, J=1.8 & 8.5 Hz, 1H, H-6), 7.04 (d, J=1.8 Hz, 1H, H-4), 4.32 (q, J=7.1 Hz, 2H, OCH$_2$CH$_3$), 2.62 (t, J=7.7 Hz, 2H, CH$_2$), 2.39–2.50 (m, 6H, 2×NCH$_2$CH$_3$ & CH$_2$), 1.68–1.72 (m, 2H, CH$_2$), 1.32 (t, J=7.1 Hz, 3H, OCH$_2$CH$_3$), 0.92 (t, J=6.8 Hz, 6H, 2×NCH$_2$CH$_3$).

MS-EI m/z 302 [M$^+$].

5-(3-Diethylamino-propyl)-1H-indole-2-carboxylic acid ethyl ester (1.2 g, 3.97 mmol) in tetrahydrofuran (48 mL) was added dropwise to the lithium aluminum hydride (602 mg, 15.87 mmol) stirred in tetrahydrofuran (30 mL) under nitrogen. After stirring for 2 hours, the reaction was quenched in water (0.6 mL), 15% sodium hydroxide (0.6 mL) and then water (1.8 mL). The mixture was stirred overnight. The precipitate was filtered off and the filtrate was concentrated to give 680 mg (66%) of [5-(3-diethylamino-propyl)-1H-indol-2-yl]-methanol.

$^1$HNMR (300 MHz, DMSO-d$_6$) δ10.83 (s, br, 1H, NH), 7.22 (s, 1H, H-3), 7.20 (d, J=8.4 Hz, 1H, H-7), 6.85 (dd, J=1.8 & 8.4 Hz, 1H, H-6), 6.16 (d, J=1.8 Hz, 1H, H-4), 5.18 (t, J=5.4 Hz, 1H, OH), 4.55 (d, J=5.4 Hz, 2H, CH$_2$OH), 2.58 (t, J=7.5 Hz, 2H, CH$_2$), 2.33–2.45 (m, 6H, 3×CH$_2$), 1.64–1.72 (m, 2H, CH$_2$), 0.90 (t, J=7.0 Hz, 6H, 2×NCH$_2$CH$_3$).

MS-EI m/z 260 [M$^+$].

Manganese oxide (3.75 g, 43.1 mmol) was added portionwise to [5-(3-diethylamino-propyl)-1H-indol-2-yl]-methanol (660 mg, 2.53 mmol) dissolved in dichloromethane (68 mL) under nitrogen at room temperature. The precipitate was filtered through celite, washing with hot dichloromethane. The filtrate was concentrated to give 563 mg (83%) of 5-(3-diethylamino-propyl)-1H-indole-2-carbaldehyde as a waxy brown solid.

$^1$HNMR (360 MHz, DMSO-d$_6$) δ11.80 (s, br, 1H, NH), 9.80 (s, 1H, CHO), 7.50 (s, 1H, H-3), 7.35 (d, J=8.5 Hz, 1H, H-7), 7.28 (s, 1H, H-4), 7.17 (d, J=1.1 & 8.5 Hz, 1H, H-6), 2.63 (t, J=7.5 Hz, 2H, CH$_2$), 2.34–2.45 (m, 6H, 3×CH$_2$), 1.67–1.71 (m, 2H, CH$_2$), 0.91 (t, J=7.0 Hz, 6H, 2×NCH$_2$CH$_3$).

MS-EI m/z 258 [M$^+$].

Example 6

Preparation of 5-(3-pyrrolidin-1-yl-propyl)-1H-indole-2-carbaldehyde

A mixture of 5-bromoindole-2-carboxylic acid ethyl ester (2.68 g, 10 mmol), tert-butyl acrylate (4.4 mL, 30 mmol) and dichlorobis(triphenylphosphine)palladium(II) (0.7 g, 1 mmol) and triethylamine (17 mL) in acetic acid (17 mL) was heated at 120° C. in a closed vessel for 6 hrs. The cooled reaction mixture was poured into water and dichloromethane. The biphasic mixture was filtered through a pad of celite and the aqueous layer was extracted with dichloromethane (2×). The combined organic layers were washed with saturated sodium bicarbonate solution, brine, dried and concentrated. The residue was purified by column chromatography (10% of ethyl acetate in hexanes) to give 900 mg (28%) of 5-(2-tert-butoxycarbonyl-vinyl)-1H-indole-2-carboxylic acid ethyl ester.

$^1$HNMR (300 MHz, DMSO-d$_6$) δ12.10 (s, br, 1H, NH), 7.94 (s, 1H), 7.64 (dd, J=1.35 & 9.15 Hz, 1H), 7.62 (d, J=16.2 Hz, H-vinyl), 7.44 (d, J=9.3 Hz, 1H), 7.16 (s, 1H), 6.41 (d, J=16.2 Hz, 1H, H-vinyl), 4.33 (q, J=7.1 Hz, 2H, OCH$_2$CH$_3$), 1.47 (s, 9H, 3×CH$_3$), 1.33 (t, J=7.1 Hz, 3H, OCH$_2$CH$_3$).

MS-EI 315 [M$^+$].

A solution of 5-(2-tert-butoxycarbonyl-vinyl)-1H-indole-2-carboxylic acid ethyl ester (1.6 g, 5 mmol) in ethyl acetate (40 mL) and methanol (80 mL) was hydrogenated over 5% palladium on carbon (0.2 g) at room temperature for overnight. The catalyst was filtered off and the filtrate was concentrated to give 1.6 g (99%) of 5-(2-tert-butoxycarbonyl-ethyl)-1H-indole-2-carboxylic acid ethyl ester as a white solid. The solid was used in the next step without further purification.

To a solution of 5-(2-tert-butoxycarbonyl-ethyl)-1H-indole-2-carboxylic acid ethyl ester (1.6 g, 5 mmol) in dichloromethane (12 mL) was added 8 mL of 40% trifluoroacetic acid. The mixture was stirred at room temperature for 1 hour. The reaction was concentrated, dissolved in toluene, concentrate, dissolved in dichloromethane and concentrated to give 1.3 g (99%) of 5-(2-carboxy-ethyl)-1H-indole-2-carboxylic acid ethyl ester.

To a solution of 5-(2-carboxy-ethyl)-1H-indole-2-carboxylic acid ethyl ester (1.3 g, 5 mmol) in 10 mL of dimethylformamide, was added 1,1'-carbonyldiimidazole (973 mg, 6 mmol). The mixture was stirred under nitrogen at room temperature for 30 mins. To the reaction mixture was added pyrrolidine (1.3 mL, 15 mmol) dropwise. After stirring at room temperature for overnight, the reaction was diluted with dichloromethane (300 mL), washed with 1N hydrochloric acid, saturated sodium bicarbonate solution, brine, dried and concentrated to give 1.5 g (95%) of 5-(3-oxo-3-pyrrolidin-1-yl-propyl)-1H-indole-2-carboxylic acid ethyl ester.

$^1$HNMR (360 MHz, DMSO-d$_6$) δ11.69 (s, br, 1H, NH), 7.45 (s, 1H), 7.34 (d, J=8.45 Hz, 1H), 7.14 (dd, J=1.87 & 8.45 Hz, 1H), 7.04 (m, 1H), 4.32 (q, J=7.18 Hz, 2H, OCH$_2$CH$_3$), 3.31 (t, J=6.55 Hz, 2H, CH$_2$), 3.26 (t, J=6.93 Hz, 2H, CH$_2$), 2.87 (t, J=7.69 Hz, 2H, CH$_2$), 2.53 (t, J=7.61 Hz, 2H, CH$_2$), 1.69–1.80 (m, 4H, 2×CH$_2$), 1.32 (t, J=7.18 Hz, 2H, OCH$_2$CH$_3$).

To a solution of 5-(3-oxo-3-pyrrolidin-1-yl-propyl)-1H-indole-2-carboxylic acid ethyl ester (1.5 g, 4.8 mmol) in 100 mL of tetrahydrofuran, lithium aluminum hydride powder (728 mg, 19.2 mmol) was added. The mixture was stirred under nitrogen at room temperature for 2 hour. To the reaction mixture was added water (0.75 mL), 15% sodium hydroxide (0.75 mL) and water (0.75 mL). It was then filtered through a pad of celite and the filtrate was concentrated. The residue was washed with ethyl acetate to give 960 mg (78%) of [5-(3-pyrrolidin-1-yl-propyl)-1H-indol-2-yl]-methanol.

$^1$HNMR (360 MHz, DMSO-d$_6$) was added 10.78 (br s, 1H, NH), 7.22 (s, 1H), 7.20 (d, J=8.05 Hz, 1H), 6.85 (dd, J=1.27 & 8.05 Hz, 1H), 6.16 (d, J=1.27 Hz, 1H), 5.11 (t, J=5.53 Hz, 1H, OH), 4.56 (d, J=5.17 Hz, 2H, CH$_2$OH), 2.61 (t, J=7.73 Hz, 2H, CH$_2$), 2.34–2.38 (m, 6H, 3×CH$_2$), 1.73 (m, 2H, CH$_2$), 1.65 (m, 4H, 2×CH$_2$).

Manganese (IV) oxide (4.7 g, 54 mmol) was added to a mixture of [5-(3-pyrrolidin-1-yl-propyl)-1H-indol-2-yl]-methanol (940 mg, 3.6 mmol) in dichloromethane (150 mL) and toluene (150 mL). The mixture was stirred at room temperature for overnight. The reaction was filtered through a pad of celite and the filtrate was concentrated to give 670 mg (72%) of 5-(3-pyrrolidin-1-yl-propyl)-1H-indole-2-carbaldehyde.

$^1$HNMR (300 MHz, DMSO-d$_6$) δ11.85 (br s, 1H, NH), 9.79 (s, 1H, CHO), 7.50 (s, 1H), 7.35 (d, J=8.6 Hz, 1H), 7.29

(d, J=1.6 Hz, 1H), 7.18 (d, J=1.6 & 8.6 Hz, 1H), 2.65 (t, J=7.8 Hz, 2H, CH$_2$), 2.33–2.38 (m, 6H, 3×CH$_2$), 1.74 (m, 2H, CH$_2$), 1.65 (m, 4H, 2×CH$_2$).

MS-EI 256 [M$^+$].

Example 7
General Condensation of Oxindoles and Aldehydes

A mixture of 1 eq. of the oxindole, 1 eq. of the aldehyde and 1–3 eq. of piperidine (or pyrrolidine) in ethanol (0.4M) was heated at 80–100° C. until the reaction was complete. The mixture was cooled to room temperature and the solid was collected by vacuum filtration, washed with ethanol and dried to give the product. Where solid was not obtained from the reaction mixture, the mixture was concentrated and purified by column chromatography.

Example 8
COMPOUND IN-001
3-[5-(3-Diethylamino-propyl)-1H-indol-2-ylmethylene]-1,3-dihydro-indol-2-one A mixture of oxindole (26 mg, 0.19 mmol), 5-(3-diethylamino-propyl)-1H-indole-2-carbaldehyde (50 mg, 0.19 mmol) and piperidine(0.1 mL) in ethanol (1 mL) was heated in a sealed tube at 95° C. for 20 hours. The precipitate was collected by vacuum filtration, washed with ethanol and dried to give 13 mg (18%) of the title compound as an orange crystalline solid.

$^1$HNMR (300 MHz, DMSO-d$_6$) δ12.88 (s, br, 1H, NH), 11.02 (s, br, 1H, NH), 7.90 (s, 1H, H-vinyl), 7.71 (d, J=7.5 Hz, 1H), 7.44–7.49 (m, 2H), 7.20 (m, 1H), 7.13 (dd, J=1.4 & 8.5 Hz, 1H), 7.0–7.04 (m, 2H), 6.89 (d, J=7.8 Hz, 1H), 2.63 (t, J=7.5 Hz, 2H, CH$_2$), 2.34–2.44 (m, 6H, 3×CH$_2$), 1.67–1.72 (m, 2H, CH$_2$), 0.91 (t, J=7.0 Hz, 6H, 2×NCH$_2$CH$_3$).

MS-EI m/z 373 [M$^+$].

Example 9
COMPOUND IN-002
5-Bromo-3-[5-(3-diethylamino-propyl)-1H-indol-2-ylmethylene]-13-dihydro-indol-2-one A mixture of 5-bromo-2-oxindole (41 mg, 0.19 mmol), 5-(3-diethylamino-propyl)-1H-indole-2-carbaldehyde (50 mg, 0.19 mmol) and piperidine(0.1 mL) in ethanol (1 mL) was heated in a sealed tube at 95° C. for 20 hours. The precipitate was collected by vacuum filtration, washed with ethanol and dried to give 52 mg (59%) of the title compound as a red-orange solid.

$^1$HNMR (300 MHz, DMSO-d$_6$) δ12.80 (s, br, 1H, NH), 11.17 (s, br, 1H, NH), 8.06 (s, 1H, H-vinyl), 7.97 (d, J=1.7 Hz, 1H), 7.47–7.51 (m, 2H), 7.35 (dd, J=1.7 & 8.2 Hz, 1H), 7.15 (m, 1H), 7.05 (s, 1H), 6.85 (d, J=8.2 Hz, 1H), 2.53–2.68 (m, 8H, 4×CH$_2$), 1.75–1.79 (m, 2H, CH$_2$), 0.97 (t, J=7.0 Hz, 6H, 2×NCH$_2$CH$_3$), MS-EI m/z 451 and 453 [M$^+$−1 and M$^+$+1].

Example 10
COMPOUND IN-003
3-[5-(3-Diethylamino-propyl)-1H-indol-2-ylmethylene]-6-phenyl-1,3-dihydro-indol-2-one A mixture of 6-phenyl-2-oxindole (41 mg, 0.19 mmol)-5-(3-diethylamino-propyl)-1H-indole-2-carbaldehyde (50 mg, 0.19 mmol) and piperidine(0.1 mL) in ethanol (1 mL) was heated in a sealed tube at 95° C. for 20 hours. The precipitate was collected by vacuum filtration, washed with ethanol and dried to give 49 mg (56%) of the title compound as an orange crystalline solid.

$^1$HNMR (300 MHz, DMSO-d$_6$) δ12.85 (s, br, 1H, NH), 11.08 (s, br, 1H, NH), 7.92 (s, 1H, H-vinyl), 7.79 (d, J=1.7 Hz, 1H), 7.65 (d, J=7.3 Hz, 2H), 7.44–7.49 (m, 4H), 7.32–7.38 (m, 2H), 7.13–7.15 (m, 2H), 7.06 (s, 1H), 2.64 (t, J=7.4 Hz, 2H, CH$_2$), 2.36–2.46 (m, 6H, 3×CH$_2$), 1.67–1.75 (m, 2H, CH$_2$), 0.92 (t, J=7.2 Hz, 6H, 2×NCH$_2$CH$_3$).

MS-EI m/z 449 [M$^+$].

Example 11
COMPOUND IN-004
3-[5-(3-Diethylamino-propyl)-1H-indol-2-ylmethlene]-5-phenyl-1,3-dihydro-indol-2-one A mixture of 5-phenyl-2-oxindole (41 mg, 0.19 mmol), 5-(3-diethylamino-propyl)-1H-indole-2-carbaldehyde (50 mg, 0.19 mmol) and piperidine(0.1 mL) in ethanol (1 mL) was heated in a sealed tube at 95° C. for 20 hours. The precipitate was collected by vacuum filtration, washed with ethanol and dried to give 10 mg (11 %) of the title compound as an orange crystalline solid.

MS-EI m/z 449 [M$^+$].

Example 12
COMPOUND IN-005
3-[5-(2-dimethylamino-ethoxy)-1H-indol-2-ylmethylene]-5-phenyl-1,3-dihydro-indol-2-one A mixture of 5-phenyl-2-oxindole (41 mg, 0.2 mmol), 5-(2-dimethylamino-ethoxy)-1H-indole-2-carbaldehyde (46 mg, 0.2 mmol) and piperidine (0.1 mL) in ethanol (1 mL) was heated at 100° C. for 2 hours. The precipitate was collected by vacuum filtration, washed with ethanol and dried to give 58 mg (68%) of the title compound.

$^1$HNMR (360 MHz, DMSO-d$_6$) δ12.87 (s, br, 1H, NH), 11.06 (s, br, 1H, NH), 8.08 (s, 2H), 7.70 (d, J=7.2 Hz, 2H), 7.44–7.53 (m, 4H), 7.33 (m, 1H), 7.16 (s, 1H), 6.92–7.0 (m, 3H), 4.06 (t, J=5.8 Hz, 2H, OCH$_2$CH$_2$N), 2.65 (t, J=5.8 Hz, 2H, OCH$_2$C$\underline{H}_2$N), 2.23 (s, 6H, N(C$\underline{H}_3$)$_2$.)

MS-EI m/z 423 [M$^+$].

Example 13
COMPOUND IN-006
5-Phenyl-3-[5-(2-pyrrolidin-1-yl-ethoxy)-1H-indol-2-ylmethylene]-1,3-dihydro-indol-2-one A mixture of 5-phenyl-2-oxindole (23 mg, 0.11 mmol), 5-(2-pyrrolidin-1-yl-ethoxy)-1H-indole-2-carbaldehyde (29 mg, 0.11 mmol) and piperidine (0.1 mL) in ethanol (1 mL) was heated at 100° C. for 2 hours. The precipitate was collected by vacuum filtration, washed with ethanol and dried to give 30 mg (61%) of the title compound as an orange solid.

$^1$HNMR (360 MHz, DMSO-d$_6$) δ12.87 (s, br, 1H, NH), 11.05 (s, br, 1H, NH), 8.08 (d, J=1.4 Hz, 2H), 7.70 (d, J=7.6 Hz, 2H), 7.44–7.53 (m, 4H), 7.31–7.35 (m, 1H), 7.15 (d, J=1.8 Hz, 1H), 6.91–7.03 (m, 3H), 4.07 (t, J=6.0 Hz, 2H, OC$\underline{H}_2$CH$_2$N), 2.80 (t, J=6.0 Hz, 2H, OCH$_2$C$\underline{H}_2$N), 2.49 (m, under DMSO H-pyrrolidine), 1.68 (m, 4H, H-pyrrolidine).

MS-EI m/z 451 [M$^+$+2].

Example 14
COMPOUND IN-007
3-[5-(2-Morpholin-4-yl-ethoxy)-1H-indol-2-ylmethylene]-1 3-dihydro-indol-2-one A mixture of 2-oxindole (29 mg, 0.22 mmol), 5-(2-morpholin-4-yl-ethoxy)-1H-indole-2-carbaldehyde (60 mg, 0.22 mmol) and piperidine (0.1 mL) in ethanol (1 mL) was heated at 100° C. for 2 hours. The precipitate was collected by vacuum filtration, washed with ethanol and dried to give 81 mg (95%) of the title compound as a yellow solid.

$^1$HNMR (360 MHz, DMSO-d$_6$) δ12.87 (s, 1H, NH), 10.97 (s br, 1H, NH), 7.88 (s, 1H, H-vinyl), 7.71 (d, J=7.6 Hz, 1H), 7.48 (m, 1H), 7.21 (t, J=7.4 Hz, 1H), 7.13 (m, 1H), 7.03 (m, 2H), 6.89–6.95 (m, 2H), 4.10 (t, J=5.8 Hz, 2H, OCH̲$_2$CH$_2$N), 3.58 (t, J=4.5 Hz, 4H, 2×CH$_2$), 2.71 (t, J=5.8 Hz, 2H, OCH$_2$CH̲$_2$N), 2.49 (m, under DMSO, 2×CH$_2$).

MS-EI m/z 389 [M$^+$].

Example 15
COMPOUND IN-008
5-Bromo-3-[5-(2-morpholin-4-yl-ethoxy)-1H-indol-2-ylmethylene]-1,3-dihydro-indol-2-one A mixture of 5-bromo-2-oxindole (46 mg, 0.22 mmol), 5-(2-morpholin-4-yl-ethoxy)-1H-indole-2-carbaldehyde (60 mg, 0.22 mmol) and piperidine (0.1 mL) in ethanol (1 mL) was heated at 100° C. for 2 hours. The precipitate was collected by vacuum filtration, washed with ethanol and dried to give 65 mg (64%) of the title compound.

$^1$HNMR (360 MHz, DMSO-d$_6$) δ12.78 (s, 1H, NH), 11.02 (s br, 1H, NH), 8.03 (s, 1H, H-vinyl), 7.96 (m, 1H), 7.49 (d, J=8.6 Hz, 1H), 7.35 (dd, J=1.4 & 8.6 Hz, 1H), 7.15 (m, 1H), 7.04 (s, 1H), 6.93–6.96 (m, 1H), 6.85 (d, J=7.9 Hz, 1H), 4.09 (t, J=5.6 Hz, 2H, OCH̲$_2$CH$_2$N), 3.58 (t, J=4.3 Hz, 4H, 2×CH$_2$), 2.71 (t, J=5.6 Hz, 2H, OCH2CH̲$_2$N), 2.49 (m, under DMSO, 2×CH$_2$).

MS-EI m/z 468 [M$^+$].

Example 16
COMPOUND IN-009
3-[5-(2-Morpholin-4-yl-ethoxy)-1H-indol-2-ylmethylene]-6-phenyl-1,3-dihydro-indol-2-one A mixture of 6-phenyl-2-oxindole (44 mg, 0.21 mmol), 5-(2-morpholin-4-yl-ethoxy)-1H-indole-2-carbaldehyde (58 mg, 0.21 mmol) and piperidine (0.1 mL) in ethanol (1 mL) was heated at 100° C. for 2 hours. The precipitate was collected by vacuum filtration, washed with ethanol and dried to give 70 mg (71%) of the title compound as an orange solid.

$^1$HNMR (300 MHz, DMSO-d$_6$) δ12.86 (s, br, 1H, NH), 11.11 (s, br, 1H, NH), 7.93 (s, 1H, H-vinyl), 7.79 (d, J=8.1 Hz, 1H), 7.65 (d, J=7.2 Hz, 2H), 7.44–7.51 (m, 3H), 7.35 (m, 2H), 7.12–7.15 (m, 2H), 7.04 (s, 1H), 6.93 (dd, J=2.1 & 8.1 Hz, 1H), 4.09 (t, J=5.8 Hz, 2H, OCH̲$_2$CH$_2$N), 3.58 (t, J=4.6 Hz, 4H, 2×CH$_2$), 2.71 (t, J=5.8 Hz, 2H, OCH$_2$CH̲$_2$N), 2.49 (m, under DMSO, 2×CH$_2$).

MS-EI m/z 465 [M$^+$].

Example 17
COMPOUND IN-010
3-[5-(2-Dimethylamino-ethoxy)-1H-indol-2-ylmethylene]-1,3-dihydro-indol-2-one A mixture of oxindole (28 mg, 0.216 mmol), 5-(2-dimethylamino-ethoxy)-1H-indole-2-carbaldehyde (50 mg, 0.21 mmol) and piperidine (0.1 mL) in ethanol (1 mL) was heated at 100° C. for 2 hours. The precipitate was collected by vacuum filtration, washed with ethanol and dried to give 59 mg (79%) of the title compound as an orange solid.

$^1$HNMR (300 MHz, DMSO-d$_6$) δ12.88 (s, br, 1H, NH), 11.01 (s, br, 1H, NH), 7.89 (s, 1H), 7.71 (d, J=7.2 Hz, 1H), 7.48 (d, J=8.7 Hz, 1H), 7.20 (dt, J=0.9 & 7.5 Hz, 1H), 7.13 (d, J=2.1 Hz, 1H), 7.0–7.05 (m, 2H), 6.88–6.93 (m, 2H), 4.05 (t, J=5.8 Hz, 2H, OCH̲$_2$CH$_2$N), 2.63 (t, J=5.8 Hz, 2H, OCH$_2$CH̲$_2$N), 2.22 (s, 6H, N(CH̲$_3$)$_2$).

MS-EI m/z 347 [M$^+$].

Example 18
COMPOUND IN-011
5-Bromo-3-[5-(2-dimethylamino-ethoxy)-1H-indol-2-ylmethylene]-1,3-dihydro-indol-2-one A mixture of 5-bromo-2-oxindole (46 mg, 0.215 mmol), 5-(2-dimethylamino-ethoxy)-1H-indole-2-carbaldehyde (50 mg, 0.21 mmol) and piperidine (0.1 mL) in ethanol (1 mL) was heated at 100° C. for 2 hours. The precipitate was collected by vacuum filtration, washed with ethanol and dried to give 72 mg (78%) of the title compound as a red solid.

$^1$HNMR (300 MHz, DMSO-d$_6$) δ -12.79 (s, br, 1H, NH), 11.10 (s, br, 1H, NH), 8.05 (s, 1H, H-vinyl), 7.97 (d, J=1.2 Hz, 1H), 7.50 (d, J=9.3 Hz, 1H), 7.35 (dd, J=1.5 & 8.1 Hz, 1H), 7.15 (d, J=2.1 Hz, 1H), 7.03 (s, 1H), 6.93 (dd, J=2.3 & 8.8 Hz, 1H), 6.85 (d, J=8.7 Hz, 1H), 4.04 (t, J=5.9 Hz, 2H, OCH̲$_2$CH$_2$N), 2.63 (t, J=5.9 Hz, 2H, OCH$_2$CH̲$_2$N), 2.22 (s, 6H, N(CH̲$_3$)$_2$).

MS-EI m/z 426 [M$^+$].

Example 19
COMPOUND IN-012
3-[5-(2-Dimethylamino-ethoxy)-1H-indol-2-ylmethylene]-6-phenyl-1,3-dihydro-indol-2-one A mixture of 6-phenyl-2-oxindole (45 mg, 0.21 mmol), 5-(2-dimethylamino-ethoxy)-1H-indole-2-carbaldehyde (50 mg, 0.21 mmol) and piperidine (0.1 mL) in ethanol (1 mL) was heated at 100° C. for 2 hours. The precipitate was collected by vacuum filtration, washed with ethanol and dried to give 68 mg (76%) of the title compound as a solid.

$^1$HNMR (300 MHz, DMSO-d$_6$) δ12.86 (s, br, 1H, NH), 11.12 (s, br, 1H, NH), 7.94 (s, 1H, H-vinyl), 7.80 (d, J=8.7 Hz, 1H), 7.66 (d, J=7.2 Hz, 2H), 7.44–7.51 (m, 3H), 7.33–7.39 (m, 2H), 7.12–7.15 (m, 2H), 7.04 (s, 1H), 6.92 (dd, J=2.1 & 8.7 Hz, 1H), 4.05 (t, J=5.9 Hz, 2H, OCH̲$_2$CH$_2$N), 2.63 (t, J=5.9 Hz, 2H, OCH$_2$CH̲$_2$N), 2.22 (s, 6H, N(CH̲$_3$)$_2$).

MS-EI m/z 423 [M$^+$].

Example 20
COMPOUND IN-013
3-[5-(2-Pyrrolidin-1-yl-ethoxy)-1H-indol-2-ylmethylene]-1,3-dihydro-indol-2-one A mixture of oxindole (26.6 mg, 0.2 mmol), 5-(2-pyrrolidin-1-yl-ethoxy)-1H-indole-2-carbaldehyde (52 mg, 0.2 mmol) and piperidine (0.1 mL) in ethanol (1 mL) was heated at 100° C. for 2 hours. The precipitate was collected by vacuum filtration, washed with ethanol and dried to give 61 mg (81%) of the title compound.

$^1$HNMR (300 MHz, DMSO-d$_6$) δ12.88 (s, br, 1H, NH), 11.01 (s, br, 1H, NH), 7.89 (s, 1H), 7.71 (d, J=7.5 Hz, 1H), 7.48 (d, J=9.3 Hz, 1H), 7.20 (dt, J=1.2 & 7.6 Hz, 1H), 7.12 (d, J=2.4 Hz, 1H), 7.0–7.05 (m, 2H), 6.88–6.93 (m, 2H), 4.06 (t, J=5.8 Hz, 2H, OCH̲$_2$CH$_2$N), 2.79 (t, J=5.8 Hz, 2H, OCH$_2$CH̲$_2$N), 2.52 (m, under DMSO H-pyrrolidine), 1.68 (m, 4H, H-pyrrolidine).

MS-EI m/z 373 [M$^+$].

Example 21
COMPOUND IN-014
5-Bromo-3-[5-(2-pyrrolidin-1-yl-ethoxy)-1H-indol-2-ylmethylene]-1,3-dihydro-indol-2-one A mixture of 5-bromo-2-oxindole (42 mg, 0.2 mmol), 5-(2-pyrrolidin-1-yl-ethoxy)-1H-indole-2-carbaldehyde (52 mg, 0.2 mmol) and piperidine (0.1 mL) in ethanol (1 mL) was heated at 100° C. for 2 hours. The precipitate was collected by vacuum filtration, washed with ethanol and dried to give 72 mg (80%) of the title compound.

$^1$HNMR (300 MHz, DMSO-d$_6$) □ 12.79 (s, br, 1H, NH), 11.12 (s, br, 1H, NH), 8.05 (s, 1H), 7.97 (d, J=1.9 Hz, 1H), 7.50 (d, J=9.0 Hz, 1H), 7.35 (dd, J=1.9 & 8.3 Hz, 1H), 7.14 (d, J=2.1 Hz, 1H), 7.03 (s, 1H), 6.93 (dd, J=2.1 & 9.0 Hz, 1H), 6.85 (d, J=8.3 Hz, 1H), 4.06 (t, J=6.0 Hz, 2H, OCH̲$_2$CH$_2$N), 2.79 (t, J=6.0 Hz, 2H, OCH$_2$CH̲$_2$N), 2.50 (m, under DMSO H-pyrrolidine), 1.67 (m, 4H, H-pyrrolidine).

MS-EI m/z 451/453 [M$^+$].

Example 22
COMPOUND IN-015
6-Phenyl-3-[5-(2-pyrrolidin-1-yl-ethoxy)-1H-indol-2-ylmethylene]-1,3-dihydro-indol-2-one A mixture of 6-phenyl-2-oxindole (41 mg, 0.2 mmol), 5-(2-pyrrolidin-1-yl-ethoxy)-1H-indole-2-carbaldehyde (50 mg, 0.2 mmol) and piperidine (0.1 mL) in ethanol (1 mL) was heated at 100° C. for 2 hours. The precipitate was collected by vacuum filtration, washed with ethanol and dried to give 65 mg (72%) of the title compound as a red solid.

$^1$HNMR (300 MHz, DMSO-$d_6$) δ12.86 (s, br, 1H, NH), 11.12 (s, br, 1H, NH), 7.94 (s, 1H), 7.80 (d, J=8.6 Hz, 1H), 7.66 (d, J=7.5 Hz, 2H), 7.44–7.51 (m, 3H), 7.33–7.39 (m, 2H), 7.12–7.14 (m, 2H), 7.05 (s, 1H), 6.92 (dd, J=1.9 & 8.6 Hz, 1H), 4.07 (t, J=5.8 Hz, 2H, OC$\underline{H}_2$CH$_2$N), 2.80 (t, J=5.8 Hz, 2H, OCH$_2$C$\underline{H}_2$N), 2.50 (m, under DMSO H-pyrrolidine), 1.68 (m, 4H, H-pyrrolidine).

MS-EI m/z 449 [M$^+$].

Example 23
COMPOUND IN-016
3-[5-(2-Diethylamino-ethoxy)-1H-indol-2-ylmethylene]-1,3-dihydro-indol-2-one A mixture of oxindole (26 mg, 0.2 mmol), 5-(2-diethylamino-ethoxy)-1H-indole-2-carbaldehyde (50 mg, 0.2 mmol) and piperidine (0.1 mL) in ethanol (1 mL) was heated at 100° C. for 2 hours. The precipitate was collected by vacuum filtration, washed with ethanol and dried to give 50 mg (67%) of the title compound.

$^1$HNMR (360 MHz, DMSO-$d_6$) δ12.87 (s, br, 1H, NH), 10.98 (s, br, 1H, NH), 7.89 (s, 1H), 7.71 (d, J=9.3 Hz, 1H), 7.48 (d, J=8.6 Hz, 1H), 7.21 (m, 1H), 7.13 (d, J=2.2 Hz, 1H), 7.03 (m, 2H), 6.89–6.92 (m, 2H), 4.02 (t, J=5.9 Hz, 2H, OC$\underline{H}_2$CH$_2$N), 2.79 (t, J=5.9 Hz, 2H, OCH$_2$C$\underline{H}_2$N), 2.56 (q, J=7.2 Hz, 4H, 2×NC$\underline{H}_2$CH$_3$), 0.98 (t, J=7.2 Hz, 6H, 2×NCH$_2$C$\underline{H}_3$).

MS-EI m/z 375 [M$^+$].

Example 24
COMPOUND IN-017
5-Bromo-3-[5-(2-diethylamino-ethoxy)-1H-indol-2-ylmethylene]-1,3-dihydro-indol-2-one A mixture of 5-bromo-2-oxindole (41 mg, 0.2 mmol), 5-(2-diethylamino-ethoxy)-1H-indole-2-carbaldehyde (50 mg, 0.2 mmol) and piperidine (0.1 mL) in ethanol (1 mL) was heated at 100° C. for 2 hours. The precipitate was collected by vacuum filtration, washed with ethanol and dried to give 60 mg (66%) of the title compound.

$^1$HNMR (360 MHz, DMSO-$d_6$) δ12.78 (s, br, 1H, NH), 11.09 (s, br, 1H, NH), 8.04 (s, 1H), 7.96 (d, J=1.7 Hz, 1H), 7.49 (d, J=8.9 Hz, 1H), 7.35 (dd, J=1.7 & 8.2 Hz, 1H), 7.14 (d, J=2.2 Hz, 1H), 7.03 (s, 1H), 6.93 (dd, J=2.2 & 8.9 Hz, 1H), 6.85 (d, J=8.2 Hz, 1H), 4.02 (t, J=6.1 Hz, 2H, OC$\underline{H}_2$CH$_2$N), 2.79 (t, J=6.0 Hz, 2H, OCH$_2$C$\underline{H}_2$N), 2.55 (q, J=7.2 Hz, 4H, 2×NC$\underline{H}_2$CH$_3$), 0.98 (t, J=7.2 Hz, 6H, 2×NCH$_2$C$\underline{H}_3$).

Example 25
COMPOUND IN-018
3-[5-(2-Diethylamino-ethoxy)-1H-indol-2-ylmethylene]-6-phenyl-1,3-dihydro-indol-2-one A mixture of 6-phenyl-2-oxindole (40.5 mg, 0.2 mmol), 5-(2-diethylamino-ethoxy)-1H-indole-2-carbaldehyde (50 mg, 0.2 mmol) and piperidine (0.1 mL) in ethanol (1 mL) was heated at 100° C. for 2 hours. The precipitate was collected by vacuum filtration, washed with ethanol and dried to give 65 mg (72%) of the title compound.

$^1$HNMR (360 MHz, DMSO-$d_6$) δ12.85 (s, br, 1H, NH), 11.08 (s, br, 1H, NH), 7.92 (s, 1H), 7.80 (d, J=7.9 Hz, 1H), 7.66 (d, J=7.9 Hz, 2H), 7.45–7.49 (m, 3H), 7.33–7.36 (m, 2H), 7.13 (m, 2H), 7.05 (s, 1H), 6.92 (dd, 1H), 4.03 (t, J=6.0 Hz, 2H, OC$\underline{H}_2$CH$_2$N), 2.80 (t, J=6.0 Hz, 2H, OCH$_2$C$\underline{H}_2$N), 2.56 (q, J=7.2 Hz, 4H, 2×NC$\underline{H}_2$CH$_3$), 0.98 (t, J=7.2 Hz, 6H, 2×NCH$_2$C$\underline{H}_3$).

MS-EI m/z 451 [M$^+$].

Example 26
COMPOUND IN-019
3-[5-(2-Diethylamino-ethoxy)-1H-indol-2-ylmethylene]-5-phenyl-1,3-dihydro-indol-2-one A mixture of 5-phenyl-2-oxindole (39 mg, 0.18 mmol), 5-(2-diethylamino-ethoxy)-1H-indole-2-carbaldehyde (48 mg, 0.18 mmol) and piperidine (0.1 mL) in ethanol (1 mL) was heated at 100° C. for 2 hours. The precipitate was collected by vacuum filtration, washed with ethanol and dried to give 44 mg (54%) of the title compound as a red solid.

$^1$HNMR (360 MHz, DMSO-$d_6$) δ12.87 (s, br, 1H, NH), 11.05 (s, br, 1H, NH), 8.09 (d, J=2.2 Hz, 2H), 7.70 (d, J=8.3 Hz, 2H), 7.44–7.53 (m, 4H), 7.33–7.35 (m, 1H), 7.15 (s, 1H), 7.03 (s, 1H), 6.98 (d, J=8.3 Hz, 1H), 6.92 (dd, J=2.2 & 9.0 Hz, 1H), 4.03 (t, J=6.1 Hz, 2H, OC$\underline{H}_2$CH$_2$N), 2.80 (t, J=6.1 Hz, 2H, OCH$_2$C$\underline{H}_2$N), 2.56 (q, J=7.2 Hz, 4H, 2×NC$\underline{H}_2$CH$_3$), 0.98 (t, J=7.2 Hz, 6H, 2×NCH$_2$C$\underline{H}_3$).

Example 27
COMPOUND IN-020
3-[5-(3-Pyrrolidin-1-yl-propyl)-1H-indol-2-ylmethylene]-1,3-dihydro-indol-2-one A mixture of oxindole (27 mg, 0.2 mmol), 5-(3-pyrrolidin-1-yl-propyl)-1H-indole-2-carbaldehyde (51 mg, 0.2 mmol) and piperidine (0.1 mL) in ethanol (1 mL) was heated in a sealed tube at 80° C. for 3 hours. The precipitate was collected by vacuum filtration, washed with ethanol/ethyl acetate and dried to give 55 mg (74%) of the title compound.

$^1$H NMR (300 MHz, DMSO-$d_6$) δ12.89 (br s, 1H, NH), 11.03 (s, 1H, NH), 7.90 (s, 1H), 7.71 (d, J=7.45 Hz, 1H), 7.48 (d, J=8.41 Hz, 1H), 7.44 (s, 1H), 7.21 (t, 1H), 7.13 (d, 1H), 7.0–7.04 (m, 2H), 6.89 (d, J=7.6 Hz, 1H), 2.66 (t, J=7.6 Hz, 2H, CH$_2$), 2.35–2.40 (m,6H, 3×CH$_2$), 1.75 (m, 2H, CH$_2$), 1.65 (m, 4H, 2×CH$_2$). MS-EI 371 [M$^+$].

Example 28
COMPOUND IN-021
2-Oxo-3-[5-(3-pyprrolidin-1-yl-propyl)-1H-indol-2-ylmethlene]-2,3-dihydro-1H-indole-5-carboxylic acid A mixture of 5-carboxy-2-oxindole (35 mg, 0.2 mmol), 5-(3-pyrrolidin-1-yl-propyl)-1H-indole-2-carbaldehyde (51 mg, 0.2 mmol) and piperidine (0.2 mL) in ethanol (1 mL) was heated in a sealed tube at 80° C. for 6 hours. The reaction mixture was concentrated and the residue was dissolved in methanol, made acidic with 1N hydrochloric acid until solid was formed. The precipitate was filtered, washed with 1N hydrochloric acid, water, ethanol and dried to give the title compound.

$^1$H NMR (360 MHz, DMSO-$d_6$) δ12.75 (br s, 1H, NH), 11.37 (s, 1H, NH), 10.67 (br s, 1H, COOH), 8.32 (s, 1H), 8.14 (s, 1H), 7.85 (dd, J=1.26 & 8.23 Hz, 1H), 7.51–7.55 (m, 2H), 7.15–7.19 (m, 2H), 7.0 (d, J=8.6 Hz, 1H), 3.50 (m, 2H, CH$_2$), 3.09 (m, 2H, CH$_2$), 2.94 (m, 2H, CH$_2$), 2.73 (t, J=7.6 Hz, 2H, CH$_2$), 1.84–2.07 (m, 6H, 3×CH$_2$). MS 416.4 [M$^+$+1].

Example 29
COMPOUND IN-021
2-Oxo-3-[5-(3-pyrrolidin-1-yl-propyl)-1H-indol-2-ylmethylene]-2,3-dihydro-1H-indole-5-carboxylic acid A mixture of 5-carboxy-2-oxindole (35 mg, 0.2 mmol), 5-(3-diethylamino-propyl)-1H-indole-2-carbaldehyde (51 mg, 0.2 mmol) and piperidine (0.1 mL) in ethanol (1 mL) was heated at 80° C. for 6 hours. The reaction was acidified with 1N HCl and the precipitate was collected by vacuum filtration, washed with 1N HCl, water and ethanol, dried to give the title compound.

$^1$HNMR (360 MHz, DMSO-$d_6$) δ12.75 (s, 1H, NH), 11.37 (s, 1H, NH), 10.67 (br s, 1H, COOH), 8.32 (s, 1H), 8.14 (s, 1H), 7.85 (dd, J=1.26 & 8.23 Hz, 1H), 7.51–7.55 (m, 2H), 7.15–7.19 (m, 2H), 7.0 (d, J=8.6 Hz, 1H), 3.50 (m, 2H), 3.09 (m, 2H), 2.94 (m, 2H), 2.73 (t, J=7.6 Hz, 2H), 1.84–2.07 (m, 6H, 3×CH$_2$).

MS m/z 416 [M$^+$+1].

Example 30
COMPOUND IN-022
2-Oxo-3-[5-(2-pyrrolidin-1-yl-ethoxy)-1H-indol-2-ylmethylene]-2,3-dihydro-1H-indole-5-carboxylic acid 2-Oxo-2,3-dihydro-1H-indole-5-carboxylic acid was condensed with 5-(2-pyrrolidin-1-yl-ethoxy)-1H-indole-2-carbaldehyde to give the title compound.

$^1$HNMR (360 MHz, DMSO-$d_6$) δ12.74 (s, 1H, NH), 11.42 (br s, 1H, NH), 8.31 (s, 1H), 8.12 (s, 1H), 7.84 (dd, 1H), 7.53 (d, 1H), 7.2 (3, 1H), 7.14 (m, 1H), 7.0 (m, 2H), 4.26 (m, 2H, CH$_2$), 2.94 (m, 2H, CH$_2$), 2.49 (m, under DMSO), 1.67 (m, 4H, 2×CH$_2$).

MS-Ve APCI m/z 416.5 [M$^+$–1].

Example 31
COMPOUND IN-023
2-Oxo-3-[5-(2-pyrrolidin-1-yl-ethoxy)-1H-indol-2-ylmethylene]-2,3-dihydro-1H-indole-6-carboxylic acid 2-Oxo-2,3-dihydro-1H-indole-6-carboxylic acid was condensed with 5-(2-pyrrolidin-1-yl-ethoxy)-1H-indole-2-carbaldehyde to give the title compound.

$^1$HNMR (360 MHz, DMSO-$d_6$) δ12.86 (s, 1H, NH), 11.11 (br s, 1H, NH), 8.01 (s, 1H, H-vinyl), 7.78 (d, J=8 Hz, 1H), 7.64 (dd, J=1.5 & 8 Hz, 1H), 7.51 (d, J=9 Hz, 1H), 7.43 (d, 1H), 7.15 (d, J=2 Hz, 1H), 7.10 (s, 1H), 4.11 (t, J=6 Hz, 2H, CH$_2$), 2.89 (t, J=6 Hz, 2H, CH$_2$), 2.61 (m, 4H, 2×CH$_2$), 1.71 (m, 4H, 2×CH$_2$).

MS-Ve APC1 m/z 416.5 [M$^+$–1].

Example 32
COMPOUND IN-024
4-(2-Hydroxy-ethyl)-3-[5-(2-pyrrolidin-1-yl-ethoxy)-1H-indol-2-ylmethylene]-1,3-dihydro-2-one 4-(2-Hydroxy-ethyl)-1,3-dihydro-indol-2-one was condensed with 5-(2-pyrrolidin-1-yl-ethoxy)-1H-indole-2-carbaldehyde to give the title compound.

$^1$HNMR (360 MHz, DMSO-$d_6$) δ13.03 (s, 1H, NH), 10.98 (br s, 1H, NH), 7.76 (s, 1H, H-vinyl), 7.48 (d, J=9 Hz, 1H), 7.12 (m, 3H), 6.92 (dd, J=2.5 & 9 Hz, 1H), 6.86 (d, J=8 Hz, 1H), 6.77 (d, J=8 Hz, 1H), 4.83 (t, J=5.4 Hz, 2H, OH), 4.07 (t, J=6 Hz, 2H, CH$_2$), 3.74 (m, 2H, CH$_2$), 3.12 (m, 2H, CH$_2$), 2.80 (t, J=6 Hz, 2H, CH$_2$), 2.52 (m, 4H, 2×CH$_2$), 1.68 (m, 4H, 2×CH$_2$).

MS-Ve APCI 416.6. [M$^+$–1].

Example 33
COMPOUND IN-025
6-Pyridin-3-yl-3-[5-(2-pyrrolidin-1-yl-ethoxy)-1H-indol-2-ylmethylene]-1,3-dihydro-2-one 6-Pyridin-3-yl-1,3-dihydro-indol-2-one was condensed with 5-(2-pyrrolidin-1-yl-ethoxy)-1H-indole-2-carbaldehyde to give the title compound.

$^1$HNMR (360 MHz, DMSO-$d_6$) δ12.85 (s, 1H, NH), 11.13 (s, 1H, NH), 8.88 (d, J=2 Hz, 1H), 8.56 (dd, 1H), 8.06 (m, 1H), 7.95 (s, 1H, H-vinyl), 7.83 (d, J=8 Hz, 1H), 7.48 (m, 2H), 7.40 (dd, 1H), 7.17 (br s, 1H), 7.13 (d, 1H), 7.06 (br, 1H), 6.93 (dd, 1H), 4.07 (t, J=6 Hz, 2H, CH$_2$), 2.80 (t, J=6 Hz, 2H, CH$_2$), 2.50 (m, 4H, 2×CH$_2$), 1.68 (m, 4H, 2×CH$_2$).

MS-Ve APCI m/z 449.5 [M$^+$–1].

Example 34
COMPOUND IN-026
6-(4-Methoxy-phenyl)-3-[5-(2-pyrrolidin-1-yl-ethoxy)-1H-indol-2-ylmethylene]-1,3-dihydro-indol-2-one 6-(4-Methoxy-phenyl)-1,3-dihydro-indol-2-one was condensed with 5-(2-pyrrolidin-1-yl-ethoxy)-1H-indole-2-carbaldehyde to give the title compound.

$^1$HNMR (360 MHz, DMSO-$d_6$) δ12.86 (s, 1H, NH), 11.03 (br s, 1H, NH), 7.85 (s, 1H, H-vinyl), 7.73 (d, J=8 Hz, 1H), 7.59 (m, 2H), 7.48 (d, J=9 Hz, 1H), 7.28 (dd, J=1..5 & 8 Hz, 1H), 7.12 (d, J=2 Hz, 1H), 7.08 (d, J=1 Hz, 1H), 7.02 (m, 3H), 6.92 (dd, J=2 & 9 Hz, 1H), 4.07 (t, J=6 Hz, 2H, CH$_2$), 3.80 (s, 3H, OCH$_3$), 2.80 (t, J=6 Hz, 2H, CH$_2$), 2.53 (m, 4H, 2×CH$_2$), 1.68 (m, 4H, 2×CH$_2$).

MS-Ve APCI m/z 478.5 [M$^+$–1].

Example 35
COMPOUND IN-027
6-(3-Methoxy-phenyl)-3-[5-(2-pyrrolidin-1-yl-ethoxy)-1H-indol-2-ylmethylene]-1,3-dihydro-indol-2-one 6-(3-Methoxy-phenyl)-1,3-dihydro-indol-2-one was condensed with 5-(2-pyrrolidin-1-yl-ethoxy)-1H-indole-2-carbaldehyde to give the title compound.

$^1$HNMR (360 MHz, DMSO-$d_6$) δ12.85 (s, 1H, NH), 11.05 (s, 1H, NH), 7.91 (s, 1H, H-vinyl), 7.78 (d, J=8 Hz, 1H), 7.49 (d, J=9 Hz, 1H), 7.33–7.39 (m, 2H), 7.21 (br d, J=8 Hz, 1H), 7.17 (m, 1H), 7.13 (br s, 2H), 7.04 (s, 1H), 6.91–6.95 (m, 2H), 4.07 (t, J=6 Hz, 2H, CH$_2$), 3.82 (s, 3H, CH$_3$), 2.80 (t, J=6 Hz, 2H, CH$_2$), 2.51 (m, 4H, 2×CH$_2$), 1.68 (m, 4H, 2×CH$_2$).

MS-Ve APCI m/z 478.7 [M$^+$–1].

Example 36
COMPOUND IN-028
6-(2-Methoxy-phenyl)-3-[5-(2-pyrrolidin-1-yl-ethoxy)-1H-indol-2-ylmethylene]-1,3-dihydro-indol-2-one 6-(2-Methoxy-phenyl)-1,3-dihydro-indol-2-one was condensed with 5-(2-pyrrolidin-1-yl-ethoxy)-1H-indole-2-carbaldehyde to give the title compound.

$^1$HNMR (360 MHz, DMSO-$d_6$) δ12.88 (s, 1H, NH), 10.97 (s, 1H, NH), 7.88 (s, 1H, H-vinyl), 7.73 (d, J=8 Hz, 1H), 7.48 (d, J=9 Hz, 1H), 7.30–7.34 (m, 2H), 7.10–7.14 (m, 3H), 7.05 (m, 3H), 6.93 (dd, J=2 & 9 Hz, 1H), 4.08 (t, J=6 Hz, 2H, CH$_2$), 3.78 (s, 3H, OCH$_3$), 2.80 (t, J=6 Hz, 2H, CH$_2$), 2.51 (m, 4H, 2×CH$_2$), 1.68 (m, 4H, 2×CH$_2$).

MS-Ve APCI m/z 478.7 [M$^+$–1].

Example 37
COMPOUND IN-029
6-(4-Fluoro-phenyl)-3-[5-(2-pyrrolidin-1-yl-ethoxy)-1H-indol-2-ylmethylene]-1,3-dihydro-2-one 6-(4-Fluoro-phenyl)-1,3-dihydro-indol-2-one was condensed with 5-(2-pyrrolidin-1-yl-ethoxy)-1H-indole-2-carbaldehyde to give the title compound.

$^1$HNMR (360 MHz, DMSO-$d_6$) δ12.84 (s, 1H, NH), 11.08 (s, 1H, NH), 7.91 (s, 1H, H-vinyl), 7.78 (d, J=8 Hz, 1H), 7.69 (m, 2H), 7.49 (d, J=9 Hz, 1H), 7.26–7.33 (m, 3H), 7.13 (d, J=2 Hz, 1H), 7.10 (d, J=1.4 Hz, 1H), 7.04 (s, 1H), 6.93 (dd, J=2 & 9 Hz, 1H), 4.07 (t, J=6 Hz, 2H, $CH_2$), 2.80 (t, J=6 Hz, 2H, $CH_2$), 2.53 (m, 4H, 2×$CH_2$), 1.68 (m, 4H, 2×$CH_2$).

MS-Ve APCI m/z 466.6 [$M^+$−1].

Example 38
COMPOUND IN-030

3-[5-(2-Morpholin-4-yl-ethoxy)-1H-indol-2-ylmethylene]-2-oxo-2,3-dihydro-1H-indole-5-carboxylic acid 2-Oxo-2,3-dihydro-1H-indole-5-carboxylic acid was condensed with 5-(2-morpholin-4-yl-ethoxy)-1HH-indole-2-carbaldehyde to give the title compound.

Example 39
COMPOUND IN-031

3-[5-(2-Morpholin-4-yl-ethoxy)-1H-indol-2-ylmethylene]-2-oxo-2,3-dihydro-1H-indole-6-carboxylic acid 2-Oxo-2,3-dihydro-1H-indole-6-carboxylic acid was condensed with 5-(2-morpholin-4-yl-ethoxy)-1HH-indole-2-carbaldehyde to give the title compound.

Example 40
COMPOUND IN-032

3-[5-(2-Morpholin-4-yl-ethoxy)-1H-indol-2-ylmethylene]-5-phenyl-1,3-dihydro-indol-2-one 5-Phenyl-1,3-dihydro-indol-2-one was condensed with 5-(2-morpholin-4-yl-ethoxy)-1HH-indole-2-carbaldehyde to give the title compound.

Example 41
COMPOUND IN-033

4-(2-Hydroxy-ethyl)-3-[5-(2-morpholin-4-yl-ethoxy)-1H-indol-2-ylmethylene]-1,3-dihydro-indol-2-one 4-(2-Hydroxy-ethyl)-1,3-dihydro-indol-2-one was condensed with 5-(2-morpholin-4-yl-ethoxy)-1HH-indole-2-carbaldehyde to give the title compound.

Example 42
COMPOUND IN-034

3-[5-(2-Morpholin-4-yl-ethoxy)-1H-indol-2-ylmethylene]-6-pyridin-3-yl-1,3-dihydro-indol-2-one 6-Pyridin-3-yl-1,3-dihydro-indol-2-one was condensed with 5-(2-morpholin-4-yl-ethoxy)-1HH-indole-2-carbaldehyde to give the title compound.

Example 43
COMPOUND IN-035

6-(4-Methoxy-phenyl)-3-[5-(2-morpholin-4-yl-ethoxy)-1H-indol-2-ylmethylene]-1,3-dihydro-indol-2-one 6-(4-Methoxy-phenyl)-1,3-dihydro-indol-2-one was condensed with 5-(2-morpholin-4-yl-ethoxy)-1H-indole-2-carbaldehyde to give the title compound.

Example 44
COMPOUND IN-036

6-(3-Methoxy-phenyl)-3-[5-(2-morpholin-4-yl-ethoxy)-1H-indol-2-ylmethylene]-1,3-dihydro-indol-2-one 6-(3-Methoxy-phenyl)-1,3-dihydro-indol-2-one was condensed with 5-(2-morpholin-4-yl-ethoxy)-1H-indole-2-carbaldehyde to give the title compound.

Example 45
COMPOUND IN-037

6-(2-Methoxy-phenyl)-3-[5-(2-morpholin-4-yl-ethoxy)-1H-indol-2-ylmethylene]-1,3-dihydro-indol-2-one 6-(2-Methoxy-phenyl)-1,3-dihydro-indol-2-one was condensed with 5-(2-morpholin-4-yl-ethoxy)-1HH-indole-2-carbaldehyde to give the title compound.

Example 46
COMPOUND IN-038

6-(4-Fluoro-phenyl)-3-[5-(2-morpholin-4-yl-ethoxy)-1H-indol-2-ylmethylene]-1,3-dihydro-indol-2-one 6-(4-Fluoro-phenyl)-1,3-dihydro-indol-2-one was condensed with 5-(2-morpholin-4-yl-ethoxy)-1HH-indole-2-carbaldehyde to give the title compound.

Example 47
COMPOUND IN-039

2-Oxo-3-[5-(2-pyrrolidin-1-yl-ethoxy)-1H-indol-2-ylmethylene]-2,3-dihydro-1H-indole-5-sulfonic acid amide A mixture of 2-oxo-2,3-dihydro-1H-indole-5-sulfonic acid amide (28 mg, 0.13 mmol), 5-(2-pyrrolidin-1-yl-ethoxy)-1H-indole-2-carbaldehyde (34 mg, 0.13 mmol) and piperidine (0.1 mL) in ethanol (1 mL) was heated at 90° C. for 2 hours. The reaction was cooled at 0° C. for overnight. The precipitate was collected by vacuum filtration, washed with cold ethanol and dried to give 47 mg (80%) of the title compound as an orange solid.

$^1$HNMR (360 MHz, DMSO-$d_6$) δ12.72 (s, 1H, NH), 11.15 (br s, 1H, NH), 8.17 (br s, 1H), 8.07 (s, 1H, H-vinyl), 7.69 (br dd, 1H), 7.51 (d, J=8.84 Hz, 1H), 7.15 (m, 4H), 7.05 (d, J=8.45 Hz, 1H), 6.95 (br dd, 1H), 4.08 (t, J=5.8 Hz, 2H, $CH_2$), 2.80 (t, J=5.8 Hz, 2H, $CH_2$), 2.53 (m, 4H, 2×$CH_2$), 1.68 (m, 4H, 2×$CH_2$).

MS-EI m/z 452 [$M^+$].

Example 48
COMPOUND IN-040

3-[5-(2-Morpholin-4-yl-ethoxy)-1H-indol-2-ylmethylene]-2-oxo-2,3-dihydro-1H-indole-5-sulfonic acid amide A mixture of 2-oxo-2,3-dihydro-1H-indole-5-sulfonic acid amide (27 mg, 0.12 mmol), 5-(2-morpholin-4-yl-ethoxy)-1H-indole-2-carbaldehyde (30 mg, 0.11 mmol) and piperidine (0.1 mL) in ethanol (1 mL) was heated at 90° C. for 2 hours. The reaction was cooled at 0° C. for overnight. The precipitate was collected by vacuum filtration, washed with cold ethanol and dried to give 38 mg (62%) of the title compound as an orange solid.

$^1$HNMR (360 MHz, DMSO-$d_6$) δ12.72 (s, 1H, NH), 11.31 (br s, 1H, NH), 8.17 (br s, 1H), 8.07 (s, 1H, H-vinyl), 7.69 (br dd, 1H), 7.51 (d, J=8.9 Hz, 1H), 7.16 (m, 4H), 7.05 (d, J=8.4 Hz, 1H), 6.95 (br dd, 1H), 4.1 (t, J=5.7 Hz, 2H, $CH_2$), 3.58 (m, 4H, 2×$CH_2$), 2.71 (t, J=5.7 Hz, 2H, $CH_2$), 2.49 (m, 4H, 2×$CH_2$).

MS-Ve APCI m/z 465.7 [$M^+$−1].

Example 49
COMPOUND IN-041

2-Oxo-3-[5-(2-pyrrolidin-1-yl-ethoxy)-1H-indol-2-ylmethylene]-2,3-dihydro-1H-indole-5-sulfonic acid methylamide 2-Oxo-2,3-dihydro-1H-indole-5-sulfonic acid methylamide was condensed with 5-(2-pyrrolidin-1-yl-ethoxy)-1H-indole-2-carbaldehyde to give the title compound.

$^1$HNMR (360 MHz, DMSO-$d_6$) δ12.71 (s, 1H, NH), 11.37 (br s, 1H, NH), 8.14 (br s, 2H), 7.63 (dd, J=2 & 8 Hz, 1H), 7.51 (d, J=9 Hz, 1H), 7.22 (m, 1H, $CH_3$NH), 7.15 (br s, 2H), 7.08 (d, J=8 Hz, 1H), 6.95 (dd, J=2 & 9 Hz, 1H), 4.08 (t, J=6 Hz, 2H, $CH_2$), 2.80 (t, J=6 Hz, 2H, $CH_2$), 2.55 (m, 4H, 2×$CH_2$), 2.44 (d, J=5 Hz, 3H, $CH_3$), 1.67 (m, 4H, 2×$CH_2$).

MS-Ve APCI m/z 465.7 [$M^+$−1].

Example 50
COMPOUND IN-042

2-Oxo-3-[5-(2-pyrrolidin-1-yl-ethoxy)-1H-indol-2-ylmethylene]-2,3-dihydro-1H-indole-5-sulfonic acid dimethylamide 2-Oxo-2,3-dihydro-1H-indole-5-sulfonic acid dimethylamide was condensed with 5-(2-pyrrolidin-1-yl-ethoxy)-1H-indole-2-carbaldehyde to give the title compound.

7.62 (dd, J=2 & 8 Hz, 1H), 7.51 (dd, J=3 & 8 Hz, 2H), 7.12–7.21 (m, 4H), 6.92–7.01 (m, 3H), 6.92–7.01 (m, 3H), 4.08 (t, J=6 Hz, 2H, CH$_2$), 3.96 (t, J=8 Hz, 2H, CH$_2$), 2.93 (t, J=8 Hz, 2H, CH$_2$), 2.81 (t, J=6 Hz, 2H, CH$_2$), 2.54 (m, 4H, 2×CH$_2$), 1.68 (m, 4H, 2×CH$_2$).

MS-Ve APCI m/z 553.8 [M$^+$−1].

Example 55
COMPOUND IN-047

2-Oxo-3-[5-(2-pyrrolidin-1-yl-ethoxy)-1H-indol-2-ylmethylene]-2,3-dihydro-1H-indole-5-sulfonic acid (3-cloro-phenyl)-methyl-amide 2-Oxo-2,3-dihydro-1H-indole-5-sulfonic acid (3-chlorophenyl)-amide was condensed with 5-(2-pyrrolidin-1-yl-ethoxy)-1H-indole-2-carbaldehyde to give the title compound.

$^1$HNMR (360 MHz, DMSO-d$_6$) δ12.67 (s, 1H, NH), 11.39 (br s, 1H, NH), 8.18 (d, J=2 Hz, 1H), 8.12 (s, 1H, H-vinyl), 7.62 (dd, J=2 & 8 Hz, 1H), 7.51 (d, J=8 Hz, 1H), 7.24 (t, J=8 Hz, 1H), 7.16 (m, 2H), 7.13 (m, 1H), 7.08 (m, 1H), 7.01–7.03 Hz, 2H, CH$_2$), 2.56 (m, 4H, 2×CH$_2$), 1.69 (m, 4H, 2×CH$_2$), 2.83 (t, J=6 Hz, 2H, CH$_2$), 2.56 (m, 4H, 2×CH$_2$), 1.69 (m, 4H, 2×CH$_2$).

MS-Ve APCI m/z 562 [M$^+$−1].

Example 51
COMPOUND IN-043

2-Oxo-3-[5-(2-pyrrolidin-1-yl-ethoxy)-1H-indol-2-ylmethylene]-2,3-dihydro-1H-indole-5-sulfonic acid isopropylamide Oxo-2,3-dihydro-1H-indole-5-sulfonic acid isopropylamide was condensed with 5-(2-pyrrolidin-1-yl-ethoxy)-2-1H-indole-2-carbaldehyde to give the title compound.

$^1$HNMR (360 MHz, DMSO-d$_6$) δ12.72 (s, 1H, NH), 11.35 (br s, 1H, NH), 8.15 (d, J=2 Hz, 1H), 7.66 (dd, J=2 & 8 Hz, 1H), 7.51 (d, J=9 Hz, 1H), 7.34 (d, J=7 Hz, 1H, (CH$_3$)$_2$CHNH), 7.15 (m, 2H), 7.06 (d, J=8 Hz, 1H), 6.95 (dd, J=2 & 9 Hz, 1H), 4.08 (t, J=6 Hz, 2H, CH$_2$), 3.27 (m, 1H, (CH$_3$)$_2$CH), 2.80 (t, J=6 Hz, 2H, CH$_2$), 2.55 (m, 4H, 2×CH$_2$), 1.68 (m, 4H, 2×CH$_2$), 0.97 (d, J=6.5 Hz, 6H, 2×CH$_3$).

MS-Ve APCI m/z 493.8 [M$^+$−1].

Example 56
COMPOUND IN-048

2-Oxo-3-[5-(2-pyrrolidin-1-yl-ethoxy)-1H-indol-2-ylmethylene]-2,3-dihydro-1H-indole-5-sulfonic acid (3-cloro-phenyl)-methyl-amide 2-Oxo-2,3-dihydro-1H-indole-5-sulfonic acid (3-chlorophenyl)-methyl-amide was condensed with 5-(2-pyrrolidin-1-yl-ethoxy)-1H-indole-2-carbaldehyde to give the title compound.

$^1$HNMR (360 MHz, DMSO-d$_6$) δ12.69 (s, 1H, NH), 11.43 (br s, 1H, NH), 8.18 (s, 1H, H-vinyl), 8.03 (d, J=2 Hz, 1H), 7.52 (d, J=9 Hz, 1H), 7.35 (m, 2H), 7.24–7.29 (m, 2H), 7.11–7.17 (m, 3H), 7.02 (d, J=8 Hz, 1H), 6.96 (dd, J=2.5 & 9 Hz, 1H), 4.08 (t, J=6 Hz, 2H, CH$_2$), 3.27 (s, 3H, CH$_3$), 2.81 (t, J=6 Hz, 2H, CH$_2$), 2.53 (m, 4H, 2×CH$_2$), 1.67 (m, 4H, 2×CH$_2$).

MS-Ve APCI m/z 576 [M$^+$−1].

Example 52
COMPOUND IN-044

2-Oxo-3-[5-(2-pyrrolidin-1-yl-ethoxy)-1H-indol-2-ylmethylene]-2,3-dihydro-1H-indole-5-sulfonic acid phenylamide 2-Oxo-2,3-dihydro-1H-indole-5-sulfonic acid phenylamide was condensed with 5-(2-pyrrolidin-1-yl-ethoxy)-1H-indole-2-carbaldehyde to give the title compound.

$^1$HNMR (360 MHz, DMSO-d$_6$) δ12.68 (s, 1H, NH), 11.36 (br s, 1H, NH), 10.09 (br s, 1H, NH), 8.14 (d, J=2 Hz, 1H), 8.08 (s, 1H, H-vinyl), 7.60 (dd, J=2 & 8.5 Hz, 1H), 7.50 (d, J=9 Hz, 1H), 7.21 (t, 2H), 7.11–7.15 (m, 4H), 7.01 (m 2H), 6.95 (dd, J=2 & 9 Hz, 1H), 4.08 (t, J=6 Hz, 2H, CH$_2$), 2.81 (t, J=6 Hz, 2H, CH$_2$), 2.54 (m, 4H, 2×CH$_2$), 1.68 (m, 4H, 2×CH$_2$).

Example 57
COMPOUND IN-049

2-Oxo-3-[5-(2-pyrrolidin-1-yl-ethoxy)-1H-indol-2-ylmethylene-2,3-dihydro-1H-indole-5-sulfonic acid (3-cloro-phenyl)-methyl-amide 2-Oxo-2,3-dihydro-1H-indole-5-sulfonic acid (4-chloro-2-fluoro-phenyl)-amide was condensed with 5-(2-pyrrolidin-1-yl-ethoxy)-1H-indole-2-carbaldehyde to give the title compound.

$^1$HNMR (360 MHz, DMSO-d$_6$) δ12.70 (s, 1H, NH), 11.36 (br s, 1H, NH), 8.09 (d, J=2 Hz, 1H), 8.07 (s, 1H, H-vinyl), 7.57 (dd, J=2 & 8 Hz, 1H), 7.51 (d, J=9 Hz, 1H), 7.31 (dd, J=2 & 10 Hz, 1H), 7.24 (d, J=9 Hz, 1H), 7.14 (m, 3H), 7.01 (d, J=8 Hz, 2H), 6.96 (dd, J=2 & 9 Hz, 1H), 4.11 (t, J=6 Hz, 2H, CH$_2$), 2.92 (t, J=6 Hz, 2H, CH$_2$), 2.66 (m, 4H, 2×CH$_2$), 1.72 (m, 4H, 2×CH$_2$).

MS-Ve APCI m/z 567.7 [M$^+$−1.

Example 53
COMPOUND IN-045

2-Oxo-3-[5-(2-pyrrolidin-1-yl-ethoxy)-1H-indol-2-ylmethylene]-2,3-dihydro-1H-indole-5-sulfonic acid pyridin-3-ylamide 2-Oxo-2,3-dihydro-1H-indole-5-sulfonic acid pyridin-3-ylamide was condensed with 5-(2-pyrrolidin-1-yl-ethoxy)-1H-indole-2-carbaldehyde to give the title compound.

$^1$HNMR (360 MHz, DMSO-d$_6$) δ12.68 (s, 1H, NH), 11.38 (br s, 1H, NH), 8.30 (d, J=2.5 Hz, 1H), 8.19 (dd, J=1.4 & 8 Hz, 1H), 8.16 (d, J=2 Hz, 1H), 8.11 (s, 1H, H-vinyl), 7.60 (dd, J=2 & 8 Hz, 1H), 7.50 (m, 2H), 7.25 (dd, J=5 & 8 Hz, 1H), 7.16 (br s, 2H), 7.02 (d, J=8 Hz, 1H), 6.96 (dd, J=2.5 & 9 Hz, 1H), 4.09 (t, J=6 Hz, 2H, CH$_2$), 2.85 (t, J=6 Hz, 2H, CH$_2$), 2.57 (m, 4H, 2×CH$_2$), 1.70 (m, 4H, 2×CH$_2$).

MS-Ve APCI m/z 528.8 [M$^+$−1].

Example 58
COMPOUND IN-050

5-(3,4-Dihydro-2H-quinoline-1-sulfonyl)-3-[5-(2-pyrrolidin-1-1-ethoxy)-1H-indol-2-ylmethylene]-1,3-dihydro-indol-2-one 5-(3,4-Dihydro-2H-quinoline-1-sulfonyl)-1,3-dihydro-indol-2-one was condensed with 5-(2-pyrrolidin-1-yl-ethoxy)-1H-indole-2-carbaldehyde to give the title compound.

Example 54
COMPOUND IN-046

5-(2,3-Dihydro-indole-1-sulfonyl)-3-[5-(2-pyrrolidin-1-yl-ethoxy)-1H-indol-2-ylmethylene]-1,3-dihydro-indol-2-one 5-(2,3-Dihydro-indole-1-sulfonyl)-1,3-dihydro-indol-2-one was condensed with 5-(2-pyrrolidin-1-yl-ethoxy)-1H-indole-2-carbaldehyde to give the title compound.

$^1$HNMR (360 MHz, DMSO-d$_6$) δ12.67 (s, 1H, NH), 11.36 (br s, 1H, NH), 8.25 (d, J=2 Hz, 1H), 8.21 (s, 1H, H-vinyl), ¹HNMR (360 MHz, DMSO-d$_6$) δ12.67 (s, 1H, NH), 11.38 (br s, 1H, NH), 8.14 (s, 1H, H-vinyl), 8.11 (d, J=2 Hz, 1H), 7.63 (d, J=8 Hz, 1H), 7.51 (d, J=9 Hz, 1H), 7.37 (dd, J=2 & 8 Hz, 1H), 7.13–7.19 (m, 3H), 7.06 (m, 2H), 6.94–6.99 (m, 2H), 4.08 (t, J=6 Hz, 2H, CH$_2$), 3.80 (t, J=6 Hz, 2H, CH$_2$), 3.25 (m, 2H, CH$_2$), 2.81 (t, J=6 Hz, 2H, CH$_2$), 2.52 (m, 4H, 2×CH$_2$), 2.48 (m, 2H, CH$_2$), 1.67 (m, 4H, 2×CH$_2$).
MS-Ve APCI m/z 580 [M$^+$–1].

Example 59

COMPOUND IN-051

5-(3,4-Dihydro-1H-isoguinoline-2-sulfonyl)-3-[5-(2-pyrrolidin-1-yl-ethoxy)-1H-indol-2-ylmethylene]-1,3-dihydro-indol-2-one 5-(3,4-Dihydro-1H-isoquinoline-2-sulfonyl)-1,3-dihydro-indol-2-one was condensed with 5-(2-pyrrolidin-1-yl-ethoxy)-1H-indole-2-carbaldehyde to give the title compound.

¹HNMR (360 MHz, DMSO-d$_6$) δ12.71 (s, 1H, NH), 11.39 (br s, 1H, NH), 8.22 (s, 1H, H-vinyl), 8.20 (d, J=1.4 Hz, 1H), 7.67 (dd, J=1.4 & 8 Hz, 1H), 7.51 (d, J=9 Hz, 1H), 7.07–7.17 (m, 7H), 6.95 (dd, J=2.5 & 9 Hz, 1H), 4.23 (s, 2H, CH$_2$), 4.08 (t, J=6 Hz, 2H, CH$_2$), 3.33 (t, J=6 Hz, 2H, CH$_2$), 2.86 (t, J=6 Hz, 2H, CH$_2$), 2.81 (t, J=6 Hz, 2H, CH$_2$), 2.52 (m, 4H, 2×CH$_2$), 1.68 (m, 4H, 2×CH$_2$),
MS-Ve APCI m/z 567.7 [M$^-$–1].

Example 60

COMPOUND IN-052

5-(5-Bromo-2,3-dihydro-indole-1-sulfonyl)-3-[5-(2-prrolidin-1-yl-ethoxy)-1H-indol-2-ylmethylene]-1,3-dihydro-indol-2-one 5-(5-Bromo-2,3-dihydro-indole-1-sulfonyl)-1,3-dihydro-indol-2-one was condensed with 5-(2-pyrrolidin-1-yl-ethoxy)-1H-indole-2-carbaldehyde to give the title compound.

¹HNMR (360 MHz, DMSO-d$_6$) δ12.67 (s, 1H, NH), 11.41 (br s, 1H, NH), 8.25 (d, J=2 Hz, 1H), 8.23 (s, 1H, H-vinyl), 7.63 (dd, J=2 & 9 Hz, 1H), 7.51 (d, J=9 Hz, 1H), 7.45 (d, J=9 Hz, 1H), 7.36 (d, J=2 Hz, 1H), 7.33 (s, 1H), 7.17 (d, J=2.5 Hz, 1H), 7.14 (s, 1H), 7.02 (d, J=8 Hz, 1H), 6.96 (dd, J=3 & 9 Hz, 1H), 4.08 (t, J=6 Hz, 2H, CH$_2$), 3.97 (t, J=9 Hz, 2H, CH$_2$), 2.95 (t, J=9 Hz, 2H, CH$_2$), 2.81 (t, J=6 Hz, 2H, CH$_2$), 2.53 (m, 4H, 2×CH$_2$), 1.68 (m, 4H, 2×CH$_2$).
MS-Ve APCI-632.0 and 634.2.

Example 61

COMPOUND IN-053

3-[5-(2-Morpholin-4-yl-ethoxy)-1H-indol-2-ylmethylene]-2-oxo-2,3-dihydro-1H-indol-5-sulfonic acid methylamide 2-Oxo-2,3-dihydro-1H-indole-5-sulfonic acid methylamide was condensed with 5-(2-morpholin-4-yl-ethoxy)-1HH-indole-2-carbaldehyde to give the title compound.

Example 62

COMPOUND IN-054

3-[5-(2-Morpholin-4-yl-ethoxy)-1H-indol-2-ylmethylene]-2-oxo-2,3-dihydro-1H-indol-5-sulfonic acid dimethylamide 2-Oxo-2,3-dihydro-1H-indole-5-sulfonic acid dimethylamide was condensed with 5-(2-morpholin-4-yl-ethoxy)-1H-indole-2-carbaldehyde to give the title compound.

Example 63

COMPOUND IN-055

3-[5-(2-Morpholin-4-yl-ethoxy)-1H-indol-2-ylmethylene]-2-oxo-2,3-dihydro-1H-indole-5-sulfonic acid isopropylamide 2-Oxo-2,3-dihydro-1H-indole-5-sulfonic acid isopropylamide was condensed with 5-(2-morpholin-4-yl-ethoxy)-1HH-indole-2-carbaldehyde to give the title compound.

Example 64

COMPOUND IN-056

3-[5-(2-Morpholin-4-yl-ethoxy)-1H-indol-2-ylmethylene]-2-oxo-2,3-dihydro-1H-indole-5-sulfonic acid phenylamide 2-Oxo-2,3-dihydro-1H-indole-5-sulfonic acid phenylamide was condensed with 5-(2-morpholin-4-yl-ethoxy)-1HH-indole-2-carbaldehyde to give the title compound.

Example 65

COMPOUND IN-057

3-[5-(2-Morpholin-4-yl-ethoxy)-1H-indol-2-ylmethylene]-2-oxo-2,3-dihydro-1H-indole-5-sulfonic acid pyridin-3-ylamide 2-Oxo-2,3-dihydro-1H-indole-5-sulfonic acid pyridin-3-ylamide was condensed with 5-(2-morpholin-4-yl-ethoxy)-1HH-indole-2-carbaldehyde to give the title compound.

Example 66

COMPOUND IN-058

5-(2,3-Dihydro-indole-1-sulfonyl)-3-[5-(2-morpholin-4-yl-ethoxy)-1H-indol-2-ylmethylene]-1,3-dihydro-indol-2-one 5-(2,3-Dihydro-indole-1-sulfonyl)-1,3-dihydro-indol-2-one was condensed with 5-(2-morpholin-4-yl-ethoxy)-1HH-indole-2-carbaldehyde to give the title compound.

Example 67

COMPOUND IN-059

3-[5-(2-Morpholin-4-yl-ethoxy)-1H-indol-2-ylmethylene]-2-oxo-2,3-dihydro-1H-indole-5-sulfonic acid (3-cloro-phenyl)-amide 2-Oxo-2,3-dihydro-1H-indole-5-sulfonic acid (3-chloro-phenyl)-amide was condensed with 5-(2-morpholin-4-yl-ethoxy)-1HH-indole-2-carbaldehyde to give the title compound.

Example 68

COMPOUND IN-060

3-[5-(2-Morpholin-4-yl-ethoxy)-1H-indol-2-ylmethylene]-2-oxo-2,3-dihydro-1H-indole-5-sulfonic acid (3-cloro-phenyl)-methyl-amide 2-Oxo-2,3-dihydro-1H-indole-5-sulfonic acid (3-chloro-phenyl)-methyl-amide was condensed with 5-(2-morpholin-4-yl-ethoxy)-1HH-indole-2-carbaldehyde to give the title compound.

Example 69

COMPOUND IN-061

3-[5-(2-Morpholin-4-yl-ethoxy)-1H-indol-2-ylmethylene]-2-oxo-2,3-dihydro-1H-indole-5-sulfonic acid (4-chloro-2-fluoro-phenyl)-amide 2-Oxo-2,3-dihydro-1H-indole-5-sulfonic acid (4-chloro-2-fluoro-phenyl)-amide was condensed with 5-(2-morpholin-4-yl-ethoxy)-1HH-indole-2-carbaldehyde to give the title compound.

Example 70

COMPOUND IN-062

5-(3,4-Dihydro-2H-quinoline-1-sulfonyl)-3-[5-(2-morpholin-4-yl-ethoxy)-1H-indol-2-ylmethylene]-1,3-dihydro-indol-2-one 5-(3,4-Dihydro-2H-quinoline-1-sulfonyl)-1,3-dihydro-indol-2-one was condensed with 5-(2-morpholin-4-yl-ethoxy)-1HH-indole-2-carbaldehyde to give the title compound.

Example 71
COMPOUND IN-063
5-(3,4-Dihydro-1H-isoquinoline-2-sulfonyl)-3-[5-(2-morpholin-4-yl-ethoxy)-1H-indol-2-ylmethylene]-1,3-dihydro-indol-2-one 5-(3,4-Dihydro-1H-isoquinoline-2-sulfonyl)-1,3-dihydro-indol-2-one was condensed with 5-(2-morpholin-4-yl-ethoxy)-1HH-indole-2-carbaldehyde to give the title compound.

Example 72
COMPOUND IN-064
5-(5-Bromo-2,3-dihydro-indole-1-sulfonyl)-3-[5-(2-morpholin-4-yl-ethoxy)-1H-indol-2-ylmethylene]-1,3-dihydro-indol-2-one 5-(5-Bromo-2,3-dihydro-indole-1-sulfonyl)-1,3-dihydro-indol-2-one was condensed with 5-(2-morpholin-4-yl-ethoxy)-1HH-indole-2-carbaldehyde to give the title compound.

Example 73
COMPOUND IN-065
3-(1H-Indol-3-ylmethylene)-2-oxo-2,3-dihydro-1H-indole-5-sulfonic acid amide 5-Aminosulfonyl-2-oxindole was condensed with indole-3-carboxaldehyde to give the title compound.

$^1$NMR (300 MHz, DMSO-$d_6$) $\delta$12.03 (br s, 1H, NH), 10.80 (br s, 1H, NH), 9.37 (s, 1H), 8.09–8.24 (m, 3H), 7.51 (m, 1H), 7.41 (m, 1H), 7.13 (m, 2H), 7.03 (s, 2H, NH2), 6.85 (d, J=7.8 Hz, 1H).
MS-EI m/z 339 [M$^+$].

Example 74
COMPOUND IN-066
3-(2-Methyl-1H-indol-3-ylmethylene)-2-oxo-2,3-dihydro-1H-indole-5-sulfonic acid amide 5-Aminosulfonyl-2-oxindole was condensed with 2-methylindole-3-carboxaldehyde to give the title compound.
MS-EI 353 [M$^+$].

Example 75
COMPOUND IN-067
3-(1H-Indol-5-ylmethylene)-2-oxo-2,3-dihydro-1H-indole-5-sulfonic acid amide 5-Aminosulfonyl-2-oxindole was condensed with indole-5-carbaldehyde to give the title compound.
MS-EI 339 [M$^+$].

Example 76
COMPOUND IN-068
3-(1H-Indol-3-ylmethylene)-2-oxo-2,3-dihydro-1H-indole-5-sulfonic acid methylamide 5-Methylaminosulfonyl-2-oxindole was condensed with indole-3-carbaldehyde to give the title compound.

$^1$HNMR (300 MHz, DMSO-$d_6$) $\delta$12.03 (br s, 1H, NH), 10.84 (br s, 1H, NH), 9.39 (s, 1H), 8.25 (s, 1H, H-vinyl), 8.22 (d, J=1.5 Hz, 1H), 8.16 (m, 1H), 7.40–7.46 (m, 2H), 7.06–7.15 (m, 2H), 7.04 (m, 1H, CH$_3$NH), 6.88 (d, J=7.8 Hz, 1H), 2.3 (d, J=5.1 Hz, 3H, CH$_3$).
MS-EI 353[M$^+$].

Example 77
COMPOUND IN-069
3-(2-Methyl-1H-indol-3-ylmethylene)-2-oxo-2,3-dihydro-1H-indole-5-sulfonic acid methylamide 5-Methylaminosulfonyl-2-oxindole was condensed with 2-methylindole-3-carboxaldehyde to give the title compound.

Example 78
COMPOUND IN-070
3-(1H-Indol-5-ylmethylene)-2-oxo-2,3-dihydro-1H-indole-5-sulfonic acid methylamide 5-Methylaminosulfonyl-2-oxindole was condensed with indole-5-carbaldehyde to give the title compound.

$^1$HNMR (300 MHz, DMSO-$d_6$) $\delta$11.38 (br s, 1H, NH), 10.85 (br s, 1H, NH), 8.11 (m, 1H), 8.01 (m, 1H), 7.90 (m, 1H), 7.78 (m, 1H), 7.37–7.53 (m, 3H), 7.10 (m, 1H), 6.95 (m, 1H), 6.4 (m, 1H), 2.28 (s, 3H, CH$_3$).
MS-EI 353 [M$^+$].

Example 79
COMPOUND IN-071
3-(1H-Indol-2-ylmethylene)-2-oxo-2,3-dihydro-1H-indole-5-sulfonic acid methylamide 5-Methylaminosulfonyl-2-oxindole was condensed with indole-2-carbaldehyde to give the title compound.

$^1$HNMR (300 MHz, DMSO-$d_6$) $\delta$12.75 (br s, 1H, NH), 11.40 (br s, 1H, NH), 8.15 (s, 1H, H-vinyl), 8.10 (d, J=1.5 Hz, 1H), 7.54–7.65 (m, 3H), 7.20–7.27 (m, 3H), 7.02–7.06 (m, 2H), 2.38 (d, J=4.8 Hz, 3H, CH$_3$).
MS-EI 353 [M$^+$].

Example 80
COMPOUND IN-072
3-(1H-Indol-3-ylmethylene)-2-oxo-2,3-dihydro-1H-indole-5-sulfonic acid dimethylamide 5-Dimethylaminosulfonyl-2-oxindole was condensed with indole-3-carboxaldehyde to give the title compound.

$^1$HNMR (360 MHz, DMSO-$d_6$) $\delta$12.11 (br s, 1H, NH), 10.94 (br s, 1H, NH), 9.50 (s, 1H), 8.44 (s, 1H), 8.33 (m, 2H), 7.51–7.53 (m, 2H), 7.25 (m, 2H), 7.03 (d, J=7.9 Hz, 1H), 2.63 (s, 6H, 2×CH$_3$).
MS-EI 367 [M$^+$].

Example 81
COMPOUND IN-073
3-(2-Methyl-1H-indol-3-ylmethylene)-2-oxo-2,3-dihydro-1H-indole-5-sulfonic acid dimethylamide 5-Dimethylaminosulfonyl-2-oxindole was condensed with 2-methylindole-3-carboxaldehyde to give the title compound.

$^1$HNMR (300 MHz, DMSO-$d_6$) $\delta$11.95 (br s, 1H, NH), 10.86 (br s, 1H, NH), 7.84 (s, 1H, H-vinyl), 7.41 (dd, J=1.8 & 8.4 Hz, 1H), 7.33 (d, J=8.4 Hz, 1H), 7.04 (m, 1H), 6.85–6.95 (m, 4H).
MS-EI 381 [M$^+$].

Example 82
COMPOUND IN-074
3-(1H-Indol-5-ylmethylene)-2-oxo-2,3-dihydro-1H-indole-5-sulfonic acid dimethylamide 5-Dimethylaminosulfonyl-2-oxindole was condensed with indole-5-carbaldehyde to give the title compound.
MS-EI 367 [M$^+$].

Example 83
COMPOUND IN-075
3-(1H-Indol-2-ylmethylene)-2-oxo-2,3-dihydro-1H-indole-5-sulfonic acid dimethylamide 5-Dimethylaminosulfonyl-2-oxindole was condensed with indol-2-carbaldehyde to give the title compound.

$^1$HNMR (360 MHz, DMSO-$d_6$) $\delta$12.80 (br s, 1H, NH), 11.44 (br s, 1H, NH), 8.30 (s, 1H, H-vinyl), 8.15 (d, J=2.2 Hz, 1H), 7.70 (d, J=7.2 Hz, 1H), 7.60 (m, 2H), 7.30 (m, 1H), 7.23 (s, 1H), 7.07–7.12 (m, 2H), 2.63 (s, 6H, 2×CH$_3$).
MS-EI 367 [M$^+$].

Example 84
COMPOUND IN-076
3-(4-Methoxy-1H-indol-2-ylmethylene)-2-oxo-2,3-dihydro-1H-indole-5-sulfonic acid methylamide A mixture of 2-oxo-2,3-dihydro-1H-indole-5-sulfonic acid methylamide (194 mg, 0.86 mmol), 4-methoxy-1H-indole-2-carbaldehyde (150 mg, 0.86 mmol) and piperidine (36 mg, 0.43 mmol) in ethanol (0.2M) was stirred at room temperature for a total of 5 days. The reaction was concentrated to ¼ of its volume and the precipitate was collected by vacuum filtration to give the title compound as a pale orangish-red solid.

$^1$HNMR (360 MHz, DMSO-$d_6$) δ12.82 (s, 1H, NH), 11.36 (br s, 1h, NH), 8.11(s, 1H-H-vinyl), 8.11 (d, J=1.3 Hz, 1H), 7.63 (dd, J=1.3 & 8.5 Hz, 1H), 7.15–7.27 (m, 4H), 7.08 (d, J=7.96 Hz, 1H), 6.56 (d, J=7.7 Hz, 1H), 3.92 (s, 3H, OCH$_3$), 2.43 (d, J=5.02 Hz, 3H, NCH$_3$).

MS m/z 384 [M$^+$+1].

Oxindole Preparation (Oxindoles Used in the Combinatorial Library)

Example 85
5-(Pyrrolidine-1-sulfonyl)-1,3-dihydro-indol-2-one

A suspension of 5-chlorosulfonyl-2-oxindole (1.62 g, 7 mmol), pyrrolidine (0.701 mL, 8.4 mmol) and pyridine (1 mL) in dichloromethane (20 mL) was stirred at room temperature for 4 hours. The reaction mixture was diluted with ethyl acetate (300 mL) and made acidic with 1N hydrochloric acid (16 mL). The organic layer was then washed with sodium bicarbonate and brine, dried and concentrated. The residue was washed with ethanol (3 mL). It was then purified by chromatography on silica gel eluting with methanol:dichloromethane 1:9 to give 0.432 g (27%)-5-(pyrrolidine-1-sulfonyl)-1,3-dihydro-indol-2-one.

$^1$H NMR (360 MHz, DMSO-$d_6$) δ10.77 (s, 1H, NH), 7.6–7.64 (m, 2H), 6.97 (d, J=8 Hz, 1H), 3.58 (s, 2H, H-3), 3.07–3.11 (m, 4H, c-pentyl), 1.63–1.66 (m, 4H, c-pentyl). MS m/z 266 [M]$^+$.

Example 86
2-Oxo-2,3-dihydro-1H-indole-5-sulfonic acid benzylamide

A suspension of 5-chlorosulfonyl-2-oxindole (1.62 g, 7 mmol), benzylamine (0.918 mL, 8.4 mmol) and pyridine (1 mL) in dichloromethane (20 mL) was stirred at room temperature for 4 hours. The reaction mixture was diluted with ethyl acetate (300 mL) and acidified with 1N hydrochloric acid (16 mL). The organic layer was then washed with sodium bicarbonate and brine, dried and concentrated. The residue was washed with ethanol (3 mL) and was then purified by chromatography on silica gel eluting with methanol:dichloromethane 1:9 to give 1.4 g (66%) of 2-oxo-2,3-dihydro-1H-indole-5-sulfonic acid benzylamide.

$^1$H NMR (360 MHz, DMSO-$d_6$) δ0.70 (s, 1H, NH-1), 7.91 (t, J=6 Hz, 1H, NHSO$_2$—), 6.63 (dd, J=2 and 8 Hz, 1H, Ar—H), 7.57 (s, 1H), 7.20–7.29 (m, 5H, Ar—H), 6.92 (d, J=8.5 Hz, 1H), 3.94 (d, J=6 Hz, 2H, CH$_2$NSO$_2$—), 3.54 (s, 2H, H-3).

Example 87
2-Oxo-2,3-dihydro-1H-indole-5-sulfonic acid-4-fluoro-benzylamide

A suspension of 5-chlorosulfonyl-2-oxindole (5.0 g), 4-fluorobenzylamine (3.0 mL) and pyridine (3.5 mL) in dichloromethane (30 mL) was stirred at room temperature for 4 hours. The precipitate was filtered, washed with dichloromethane and dried to give 5.8 g (84%) of 2-oxo-2,3-dihydro-1H-indole-5-sulfonic acid-4-fluoro-benzylamide.

$^1$H NMR (360 MHz, DMSO-$d_6$) δ10.74 (s, 1H, NH-1), 7.50–7.55 (m, 2H, H-4, 6), 7.21–7.26 (m, 4H, Ar—H), 7.04–7.09 (m, 1H, SO2NH), 6.90–6.92 (d, 1H, H-7), 3.91–3.93 (d, 2H, NHCH$_2$), 3.53 (s, 2H, H-3). MS m/z 320.

Example 88
2-Oxo-2,3-dihydro-1H-indole-5-sulfonic acid (3-chloro-phenyl)-amide A suspension of 5-chlorosulfonyl-2-oxindole (5 g), 3-chloroaniline (2.74 mL) and pyridine (3.5 mL) in dichloromethane (30 mL) was stirred at room temperature for overnight. The precipitate was filtered, washed with dichloromethane and dried to give 5.2 g (74%) 2-oxo-2,3-dihydro-1H-indole-5-sulfonic acid (3-chloro-phenyl)-amide.

$^1$NMR (360 MHz, DMSO-$d_6$) δ10.74 (s, br, 1H, NH), 10.41 (s, 1H, SO$_2$NH), 7.59–7.64 (m, 2H, H-4,6), 7.22–7.26 (m, 1H, Ar—H), 7.10–7.11 (m, 1H, Ar—H), 7.03–7.07 (m, 2H, Ar—H), 6.9–6.92 (d, 1H, H-7), 3.54 (s, 3H, CH$_3$). MS m/z 322 (M$^+$).

Example 89
2-Oxo-2,3-dihydro-1H-indole-5-sulfonic acid (2-methoxy-phenyl)-amide A solution of 5-chlorosulfonyl-2-oxindole (3 g), o-anisidine (1.8 mL) and pyridine (2.1 mL) in dichloromethane (20 mL) was stirred at room temperature for overnight at which time the red color solid was present. The solid was filtered, washed with ethanol and dried under vacuum to yield 1.5 g (37%) of 2-oxo-2,3-dihydro-1H-indole-5-sulfonic acid (2-methoxy-phenyl)-amide.

$^1$H NMR (360 MHz, DMSO-$d_6$) δ10.71 (s, 1H, NH-1), 9.19 (s, 1H, SO$_2$NH), 7.51–7.54 (m, 2H, H-4, 6), 7.18–7.20 (m, 1H, Ar—H), 7.04–7.09 (m, 1H, Ar—H), 6.78–6.89 (m, 3H, H-7, Ar—H), 3.44–3.56 (m, 5H, H-3, OCH$_3$). MS m/z (APCI-) 317.2.

Example 90
2-Oxo-2,3-dihydro-1H-indole-5-sulfonic acid pyridin-3-ylamide

A solution of 5-chlorosulfonyl-2-oxindole (3 g) and 3-aminopyridine (1.46 g) in pyridine (15 mL) was stirred at room temperature for overnight at which time the brown color solid was present. The precipitate was filtered, washed with ethanol and dried under vacuum to yield 1.4 g (38%) of 2-oxo-2,3-dihydro-1H-indole-5-sulfonic acid pyridin-3-ylamide.

$^1$H NMR (360 MHz, DMSO-$d_6$) δ10.74 (s, 1H, NH-1), 10.39 (s, 1H, SO$_2$NH), 8.27–8.28 (d, 1H, Ar—H), 8.21–8.23 (m, 1H, Ar—H), 7.59–7.62 (m, 2H, H-4, 6), 7.44–7.68 (m, 1H, Ar—H), 7.24–7.28 (m, 1H, Ar—H), 6.69–6.71 (d, 1H, H-7), 3.54 (s, 2H, H-3). MS m/z (APCI+) 290.2.

Example 91
2-Oxo-2,3-dihydro-1H-indole-5-sulfonic acid (2-methoxy-ethyl)-amide A solution of 5-chlorosulfonyl-2-oxindole (5 g), 2-methoxyethylamine (2.25 mL) and pyridine (7 mL) in dichloromethane (30 mL) was stirred at room temperature for 4 hours. The reaction was concentrated and dichloromethane (15 mL) was added. The precipitate was filtered, washed with dichloromethane and dried to give 1.9 g (33%) of 2-oxo-2,3-dihydro-1H-indole-5-sulfonic acid (2-methoxy-ethyl)-amide.

$^1$H NMR (360 MHz, DMSO-$d_6$) δ10.72 (s, br, 1H, NH), 7.63 (dd, J=2 and 8 Hz, 1H), 7.59 (s, 1H), 7.48 (t, J=6 Hz, 1H, NH), 6.93 (d, J=8 Hz, 1H), 3.57 (s, 2H), 3.29 (t, J=6 Hz, 2H, CH$_2$), 3.16 (s, 3H, OCH$_3$), 2.82–2.87 (q, J=6 Hz, 2H, CH$_2$). MS m/z 270 M$^+$.

Example 92
5-Aminosulfonyl-2-oxindole

To a 100 mL flask charged with 27 mL of chlorosulfonic acid, 13.3 g of 2-oxindole was added slowly. The reaction temperature was maintained below 30° C. during the addition. After the addition, the reaction mixture was stirred at room temperature for 1.5 hour, heated to 68° C. for 1 hour, cooled, and poured into water. The precipitate was washed with water and dried in a vacuum oven to give 11.0 g of 5-chlorosulfonyl-2-oxindole (50% yield) which was used without further purification.

5-Chlorosulfonyl-2-oxindole (2.1 g) was added to 10 mL of ammonium hydroxide in 10 mL of ethanol and stirred at room temperature overnight. The mixture was concentrated and the solid collected by vacuum filtration to give 0.4 g (20% yield) of 5-aminosulfonyl-2-oxindole as an off-white solid.

$^1$H NMR (360 MHz, DMSO-$d_6$) δ10.67 (s, 1H, NH-1), 7.63–7.66 (m, 2H, H-4,6), 7.13 (s, 2H, 5—SO2NH2), 6.91 (d, J=8 Hz, 1H, H-7), and 3.56 (s, 2H, CH$_2$-3). MS m/z 211 ]M-1]$^+$.

Example 93
5-Methylaminosulfonyl-2-oxindole

A suspension of 3.38 g of 5-chlorosulfonyl-2-oxindole in 10 mL of 2M methylamine in tetrahydrofuran was stirred at room temperature for 4 hours at which time a white solid was present. The precipitate was collected by vacuum filtration, washed twice with 5 mL of water each time and dried under vacuum at 40° C. overnight to give 3.0 g (88 % yield) of 5-methylaminosulfonyl-2-oxindole.

$^1$H NMR (300 MHz, DMSO-$d_6$) δ10.87 (s, br, 1H, NH-1), 7.86 (s, br, 1H, 5-SO$_2$NHCH$_3$), 7.61 (d, J=8 Hz-1H, H-6), 7.32 (d, J=5 Hz, 1H, H-4), 6.97 (d, J=8 Hz, 1H, H-7), 2.53 (s, 2H, CH$_2$-3), and 2.36 (s, 3H, 5—SO$_2$NHCH$_3$). MS m/z 226.

Example 94
5-Dimethylaminosulfonyl-2-oxindole

A suspension of 2.3 g of 5-chlorosulfonyl-2-oxindole in 10 mL of 2M dimethylamine in methanol was stirred at room temperature for 4 hours at which time a white solid was present. The precipitate was collected by vacuum filtration, washed with 5 mL of 1N sodium hydroxide and 5 mL of 1N hydrochloric acid and dried under vacuum at 40° C. overnight to give 1.9 g (79 % yield) of 5-dimethylaminosulfonyl-2-oxindole.

$^1$H NMR (300 MHz, DMSO-$d_6$) δ10.87 (s, br, 1H, NH, 7.73 (d, J=1 Hz, 1H, H-4), 7.58 (dd, J=1 and 8 Hz, 1H, H-6), 7.02 (d, J=8 Hz, 1H, H-7), 2.59 (s, 3H, CH$_3$), 2.54 (s, 2H, H-3), 2.36 (s, 3H, CH$_3$).

Example 95
5-Isopropylaminosulfonyl-2-oxindole

A suspension of 3 g of 5-chlorosulfonyl-2-oxindole, 1.15 g of isopropylamine and 1.2 mL of pyridine in 50 mL of dichloromethane was stirred at room temperature for 4 hours at which time a white solid was present. The precipitate was collected by vacuum filtration. The solids were slurry-washed with hot ethanol, cooled, collected by vacuum filtration and dried under vacuum at 40° C. overnight to give 1.5 g (45% yield) of 5-isopropylaminosulfonyl-2-oxindole.

$^1$H NMR (360 MHz, DMSO-$d_6$) δ10.69 (s, br, 11H, NH), 7.63 (dd, J=2 and 8 Hz, 1H, H-6), 7.59 (d, J=2 Hz, 1H, H-4), 7.32 (d, J=7 Hz, 1H, NH—SO$_2$—), 6.93 (d, J=8 Hz, 11H, H-7), 3.57 (s, 2H, H-3), 3.14–3.23 (m, 11H, CH—(CH$_3$)$_2$), 0.94 (d, J=7 Hz, 6H, 2×CH$_3$).

Example 96
5-Phenyl-1,3-dihydro-indol-2-one

5-Bromo-2-oxindole (5 g, 23.5 mmol) was dissolved in 110 mL of toluene and 110 mL of ethanol with stirring and a little heating. Tetrakis(triphenylphosphine)-palladium(0) (1.9 g, 1.6 mmol) was added followed by a 2M aq. solution of sodium carbonate (40 mL, 80 mmol). To this mixture benzene boronic acid (3.7 g, 30.6 mmol) was added and the mixture was heated in a 100° C. oil bath. After 12 h, the reaction was diluted with ethyl acetate (500 mL), washed with saturated aq. sodium bicarbonate (200 mL), water (200 mL), 1N HCl (200 mL) and brine (200 mL). The organic layer was dried with magnesium sulfate and concentrated to afford a brown solid. Trituration with dichloromethane and filtering afforded 3.8 g (77%) of a tan solid.

$^1$H NMR (360 MHz, DMSO-$d_6$) δ10.4 (br s, 1H, NH), 7.57 (dd, J=1.8 and 7.2 Hz, 1H, Ar—H), 7.5 to 7.35 (m, 5H, Ar—H), 7.29 (m, 1H, Ar—H), 6.89 (d, J=8.2 Hz, 1H, Ar—H), 3.51 (s, 2H, CH$_2$CO). MS m/z (relative intensity %, ion) found 209 (100, M$^+$); calc. 209.2.

Example 97
6-Pyridin-3-yl-1,3-dihydro-indol-2-one

To a solution of 6-bromo-2-oxindole (4 g, 26.3 mmol) dissolved in 60 mL of toluene and 60 mL of ethanol with stirring and a little heating tetrakis(triphenyl-phosphine) palladium(0) (2.3 g, 1.9 mmol) was added followed by a 2M aqueous solution of sodium carbonate (50 mL, 100 mmol) and pyridine-3-boronic acid propane diol (5 g, 30.7 mmol). The mixture was heated in a 100° C. oil bath for 12 hours. The cooled reaction was diluted with ethyl acetate (500 mL), washed with saturated aqueous sodium bicarbonate (200 mL), water (200 mL) and brine (200 mL). The organic layer was dried with magnesium sulfate and concentrated to afford a brown solid. The residue was triturated with methylene chloride/diethyl ether to give 2.32 g (42%) of 6-pyridin-3-yl-1,3-dihydro-indol-2-one as a brown solid.

$^1$H NMR (360 MHz, DMSO-$d_6$) δ10.51 (s, 1H, NH), 8.81 (d, J=2.5 Hz, 1H, Ar—H), 8.55 (dd, J=1.8 and 5.7 Hz, 1H, Ar—H), 8 (m, 1H, Ar—H), 7.45 (dd, J=5.7 and 9.3 Hz, 1H, Ar—H), 7.3 (m, 2H, Ar—H), 7.05 (s, 1H, Ar—H), 3.51 (s, 2H, CH$_2$CO). MS m/z 210 [M]$^+$.

Example 98
6-Phenyl-2-oxindole

Tetrakis(triphenylphosphine)palladium (0.8 g) was added to a mixture of benzeneboronic acid (3.1 g), 5-bromo-2-fluoronitrobenzene (5 g) and 22 mL of 2M sodium carbonate solution in toluene (50 mL) and ethanol (50 mL). The mixture was heated to reflux for 2 hours, concentrated, and the residue was extracted twice with ethyl acetate. The ethyl acetate layer was washed with water, brine, dried, and concentrated to give a yellow oil. The oil was purified by column chromatography on silica gel in 5% ethyl acetate in hexane to give 4.75 g (96% yield) of 4-fluoro-3-nitrobiphenyl as a yellow oil.

Dimethyl malonate (10 mL) in 25 mL of dimethylsulfoxide was added dropwise to 3.5 g of sodium hydride suspended in 25 mL of dimethylsulfoxide and the mixture heated at 100° C. for 10 minutes. The mixture was cooled to room temperature and 4.7 g of 4-fluoro-3-nitrobiphenyl in 25 mL of dimethylsulfoxide was added. The mixture was heated at 100° C. for 2 hours, cooled and quenched with 300 mL of saturated ammonium chloride solution. The mixture was extracted three times with ethyl acetate and the combined organic layers were washed with water and brine and evaporated to give crude dimethyl-3-nitrobiphenyl-4-malonate as a yellow oil.

Crude dimethyl-3-nitrobiphenyl-4-malonate was heated to reflux in 30 mL of 6N hydrochloric acid for 24 hours. The precipitate was collected by filtration, washed with water and dried to give 4.5 g (80% based on-4-fluoro-3-nitrobiphenyl) of 3-nitrobiphenyl-4-acetic acid as a cream colored solid.

Iron chips (2.6 g) were added all at once to 4.5 g of 3-nitrobiphenyl-4-acetic acid in 40 mL of acetic acid. The mixture was heated to reflux for 2 hours, concentrated to dryness and taken up in ethyl acetate. The solids were removed by filtration and the filtrate was washed twice with 1N hydrochloric acid and brine and dried over anhydrous sodium sulfate. The filtrate was concentrated to give 3.4 g (93% yield) of 6-phenyl-2-oxindole as a light brown solid.

$^1$H NMR (360 MHz, DMSO-$d_6$) δ10.4 (s, br, 1H, NH-1), 7.57–7.6 (m, 2H), 7.42–7.46 (m, 2H), 7.32–7.37 (m, 1H), 7.27 (d, J=8 Hz, 1H, H-4), 7.19 (dd, J=2, 8 Hz, 1H, H-5), 7.01 (d, J=2 Hz, 1H, H-7), 3.49 (s, 2H, $CH_2$). MS m/z 210 [M+1]$^+$.

Example 99
6-(2-Methoxyphenyl)-2-oxindole

Tetrakis(triphenylphosphine)palladium (1 g) was added to a mixture of 2-methoxyphenylboronic acid (5 g), 5-bromo-2-fluoronitrobenzene (6.6 g) and 30 mL of 2M sodium carbonate solution in toluene (50 mL) and ethanol (50 mL). The mixture was heated to reflux for 2 hours, concentrated, and the residue was extracted twice with ethyl acetate. The ethyl acetate layer was washed with water, brine, dried, and concentrated to give a dark green oil which solidified on standing, crude 4-fluoro-2'-methoxy-3-nitrobiphenyl.

Dimethyl malonate (14 mL) was added dropwise to 2.9 g of sodium hydride suspended in 50 mL of dimethylsulfoxide. The mixture was heated at 100° C. for 15 minutes and cooled to room temperature. Crude-4-fluoro-2'-methoxy-3-nitrobiphenyl in 60 mL of dimethylsulfoxide was added and the mixture was heated at 100° C. for 2 hours. The reaction mixture was cooled and quenched with 300 mL of saturated ammonium chloride solution and extracted twice with ethyl acetate. The extracts were combined, washed with saturated ammonium chloride, water, and brine, dried over anhydrous sodium sulfate and concentrated to give crude dimethyl 2'-methoxy-3-nitrobiphenyl-4-malonate as a yellow oil.

Crude-2'-methoxy-3-nitrobiphenyl-4-malonate was heated at 100° C. in 50 mL of 6N hydrochloric acid for 24 hours and cooled. The precipitate was collected by filtration, washed with water and hexane, and dried to give 9.8 of 2'-methoxy-2-nitrobiphenyl-4-acetic acid as a light tan solid.

Iron chips (5 g) were added in one portion to 9.8 g of 2'-methoxy-3-nitrobiphenyl-4-acetic acid in 50 hours. The reaction mixture was concentrated to dryness, sonicated in ethyl acetate and filtered to remove the insolubles. The filtrate was washed twice with 1N hydrochloric acid, water, brine, dried over anhydrous sodium sulfate and concentrated. The residue was purified by column chromatography on silica gel in ethyl acetate:hexane 1:2 to give 5.4 g (69 % yield based on-5-bromo-2-fluoronitrobenzene) of 6-(2-methoxyphenyl)-2-oxindole as a rose colored solid.

$^1$H NMR (360 MHz, DMSO-$d_6$) δ10.32 (s, br, 1H, NH), 7.29–7.34 (m, 1H), 7.19–7.25 (m, 2H), 7.08 (d, J=8 Hz, 1H, H-4), 6.97–7.02 (m, 2H), 6.91 (d, J=1 Hz, 1H, H-7), 3.8 (s, 3H, $OCH_3$), 3.47 (s, 2H, $CH_2$). MS m/z 239.8 [M+1]$^+$.

Example 100
6-(3-Methoxyphenyl)-2-oxindole

Tetrakis(triphenylphosphine)palladium (0.7 g) was added to a mixture of 3.8 g of 3-methoxyphenylboronic acid, 5 g of 5-bromo-2-fluoronitrobenzene and 11 mL of 2M sodium carbonate solution in 100 mL of toluene. The mixture was heated to reflux for 2 hours, diluted with water and extracted with ethyl acetate. The ethyl acetate was washed with saturated sodium bicarbonate, brine, dried, and concentrated to give an oily solid. The solid was purified by column chromatography on silica gel in ethyl acetate:hexane 1:6 to give 4.3 g (77% yield) of 4-fluoro-3'-methoxy-3-nitrobiphenyl.

Dimethyl malonate (9.7 mL) was added dropwise to 2.0 g of sodium hydride suspended in 50 mL of dimethylsulfoxide. The mixture was heated to 100° C. for 35 minutes and cooled to room temperature. 4-Fluoro-2'-methoxy-3-nitrobiphenyl (4.2 g) in 50 mL of dimethylsulfoxide was added and the mixture was heated at 100° C. for 1 hour. The reaction mixture was cooled and quenched with 300 mL of saturated ammonium chloride solution and extracted twice with ethyl acetate. The extracts were combined, washed with brine, dried over anhydrous sodium sulfate and concentrated to give crude dimethyl 3'-methoxy-3-nitrobiphenyl-4-malonate as a pale yellow solid.

Crude 3'-methoxy-3-nitro-biphenyl-4-malonate was heated at 110° C. in 45 mL of 6N hydrochloric acid for 4 days and cooled. The precipitate was collected by filtration, washed with water and hexane, and dried to give 5.3 g of 3'-methoxy-2-nitrobiphenyl-4-acetic acid as a light tan solid.

3'-Methoxy-3-nitrobiphenyl-4-acetic acid (5.2 g) was dissolved in methanol and hydrogenated over 0.8 g of 10% palladium on carbon for 3 hours at room temperature. The catalyst was removed by filtration, washed with methanol and the filtrates combined and concentrated to give a brown solid. The solid was purified by column chromatography on silica gel in ethyl acetate:hexane:acetic acid 33:66:1 to give 3.0 g (75% yield based on 4-fluoro-3'-methoxy-3-nitrobiphenyl) of 6-(3-methoxypheny)-2-oxindole as a pink solid.

$^1$H NMR (360 MHz, DMSO-$d_6$) δ10.39 (s, br, 1H, NH), 7.35 (t, J=8 Hz, 1H), 7.26 (d, J=8 Hz, 1H), 7.19 (dd, J=1, 8 Hz, 1H), 7.13–7.16 (m, 1H), 7.09–7.1 (m, 1H), 7.01 (d, J=1 Hz, 1H), 6.90–6.93 (m, 1H), 3.8 (s, 3H, $OCH_3$), 3.49 (s, 2H, $CH_2$). MS m/z 240.0 [M+1]$^+$.

Example 101
6-(4-Methoxyphenyl-2-oxindole

Tetrakis(triphenylphosphine)palladium (1 g) was added to a mixture of 5 g of 4-methoxyphenylboronic acid, 6.6 g of 5-bromo-2-fluoronitrobenzene and 30 mL of 2M sodium carbonate solution in 50 mL of toluene and 50 mL of ethanol. The mixture was heated to reflux for 2 hours, concentrated, and the residue extracted twice with ethyl acetate. The ethyl acetate layer was washed with water, brine, dried, and concentrated to give a brown oily solid. The solid was purified by column chromatography on silica gel in 5% ethyl acetate in hexane to give crude-4-fluoro-4'-methoxy-3-nitrobiphenyl as a pale yellow solid.

Dimethyl malonate (10 mL) was added dropwise to 2.0 g of sodium hydride suspended in 60 mL of dimethylsulfoxide. The mixture was heated to 100° C. for 10 minutes and cooled to room temperature. Crude 4-fluoro-2'-methoxy-3-nitrobiphenyl (5.2 g) in 50 mL of dimethylsulfoxide was added and the mixture was heated at 100° C. for 2 hours. The reaction mixture was cooled and quenched with 300 mL of saturated ammonium chloride solution and extracted three times with ethyl acetate. The extracts were combined, washed with saturated ammonium chloride, water and brine, dried over anhydrous sodium sulfate and concentrated to give crude dimethyl 4'-methoxy-3-nitrobiphenyl-4-malonate as a yellow oil.

Crude 4'-methoxy-3-nitro-biphenyl-4-malonate was heated at 100° C. in 60 mL of 6N hydrochloric acid for 15 hours and cooled. The precipitate was collected by filtration, washed with water and hexane, and dried to give 7.2 g of crude 4'-methoxy-3-nitrobiphenyl-4-acetic acid as a light tan solid.

Iron chips (3.6 g) were added in one portion to 7.2 g of 4'-methoxy-3-nitrobiphenyl-4-acetic acid in 50 mL of glacial acetic acid and heated at 100° C. overnight. The reaction mixture was concentrated to dryness, sonicated in ethyl acetate and filtered to remove the insolubles. The filtrate was washed twice with 1 N hydrochloric acid, brine, dried over anhydrous sodium sulfate and concentrated to give 2.7 g (54% yield based on 5-bromo-2-fluoronitrobenzene) of 6-(4-methoxyphenyl)-2-oxindole as a rose colored solid.

$^1$H NMR (360 MHz, DMSO-d$_6$) δ10.38 (s, br, 1H, NH-1), 7.52 (d, J=9 Hz, 2H), 7.23 (d, J=7 Hz, 1H, H-4), 7.14 (dd, J=1, 7 Hz, 1H, H-5), 7.0 (d, J=9 Hz, 2H), 6.96 (d, J=1 Hz, 1H, H-7), 3.78 (s, 3H, OCH$_3$), 3.47 (s, 2H, CH$_2$). MS m/z 214.0 [M+1]$^+$.

Example 102
2-Oxo-2,3-dihydro-1H-indole-4-carboxylic acid (3-chloro-4-methoxy-phenyl)-amide To a solution of 2-oxo-2,3-dihydro-1H-indole-4-carboxylic acid (200 mg, 1.13 mmol) and 3-chloro-4-methoxy-phenylamine (178 mg, 1.13 mmol) in dimethylformamide (15 mL) at room temperature benzotriazol-1-yloxytris(dimethylamino)phosphonium hexafluorophosphate (BOP reagent 997 mg, 2.26 mmol) was added followed by 4-dimethylaminopyridine (206 mg, 1.69 mmol). The mixture was stirred at room temperature for 72 hours. The reaction was then diluted with ethyl acetate (300 mL), washed with saturated sodium bicarbonate solution (100 mL), water, 2N hydrochloric acid (100 mL), water (3×200 mL) and brine, dried (over magnesium sulfate) and concentrated. The residue was triturated with ethyl acetate to give 2-oxo-2,3-dihydro-1H-indole-4-carboxylic acid (3-chloro-4-methoxy-phenyl)-amide as a tarnish-pink solid.

$^1$H NMR (360 MHz, DMSO-d$_6$) δ10.50 (s, br, 1H, NH), 10.12 (s, br, 1H, NH), 7.9 (s, J=2.5 Hz, 1H), 7.62 (dd, J=2.5 & 9 Hz, 1H), 7.38 (d, J=7.6 Hz, 1H), 7.32 (t, J=7.6 Hz, 1H), 7.13 (d, J=9 Hz, 1H), 6.98 (d, J=7.6 Hz, 1H), 3.83 (s, 3H, OCH$_3$), 3.69 (s, 2H, CH$_2$). MS-EI m/z 316 [M]$^+$.

Example 103
2-Oxo-2,3-dihydro-1H-indole-4-carboxylic acid ethylamide

Ethylamine (2.1 mL of 2.0M solution in tetrahydrofuran, 4.2 mmol) was added dropwise to a suspension of 4-carboxy-2-oxindole (380 mg, 2.1 mmol) in dimethylformamide (8 mL), followed by 4-dimethylaminopyridine (385 mg, 3.15 mmol) and PyBOP (2.185 g, 4.2 mmol). The mixture was stirred at room temperature for 6 hrs. The reaction was concentrated. The residue was dissolved in dichloromethane, washed with saturated sodium bicarbonate and brine, dried, concentrated and recrystallized to give 280 mg (65%) of 2-oxo-2,3-dihydro-1H-indole-4-carboxylic acid ethylamide.

$^1$H NMR (300 MHz, DMSO-d$_6$) δ10.44 (br s, 1H, NH), 8.24 (m, 1H, CON$\underline{H}$CH$_2$CH$_3$), 7.24 (m, 2H), 6.90 (dd, J=2.1 & 6.4 Hz, 1H), 3.63 (s, 2H, CH$_2$), 3.24 (m, 2H, NC$\underline{H}_2$CH$_3$), 1.10 (t, J=7.1 Hz, 3H, NCH$_2$C$\underline{H}_3$). MS-EI 204 [M$^+$].

Example 104
General Synthetic Method for the Combinatorial Libraries

The preparation of the compounds of the invention that were prepared using the combinatorial library method followed one of the following general schemes.

Solution Phase 0.5M solutions in DMSO of oxindoles and aldehydes were prepared. Piperidine (20 μL) was added to each solution to aid in solvation. 220 μL each of the appropriately substituted oxindole and the appropriately substituted aldehyde were added to each well, followed by piperidine (30 μL). The mixtures were heated at 70° C. for 15 hours. After cooling down, DMSO was added to each well to make the total volume to 1 μL. The solutions were then transferred to 96 mother plate and used for biological testing.

0.5M Solutions in DMSO (2.5 μL) of oxindoles and aldehydes were prepared. Piperidine (20 μL) was added to each solution to aid in solvation. 220 μL each of the appropriately substituted oxindole and the appropriately substituted aldehyde were added to each well, followed by piperidine (30 μL). The mixtures were heated at 70° C. for 15 hours. After cooling down, DMSO was added to each well to make the total volume to 1 mL. Piperidine was removed under high vacuum. The solutions were then transferred to 96 mother-well plate and used for biological testing.

Solid Phase

1. Attachment of Resin to Oxindoles

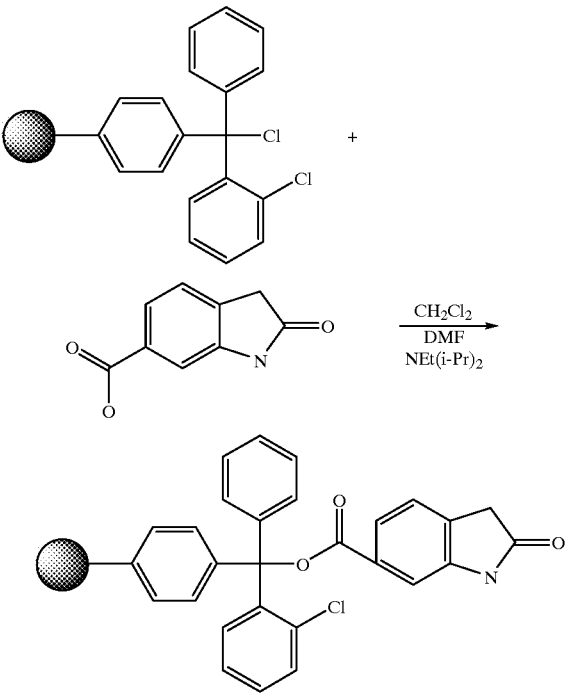

Starting oxindole (1.584 g, 1.2 eq) was dissolved in 50 mL Dichloromethane and 5.2 mL (4 eq) DIPEA under nitrogen. DMF (5 mL) was added to aid in solvation. Resin (5 g, 7.45 mmol, 1 eq) was added and stirred gently overnight. Filtered resin and washed with 300 mL of 17:2:1 DCM/MeOH/DIPEA, 200 mL of DMF, and 200 mL of DCM.

The solvent was removed under high vacuum. 6.12 g of resin was collected.

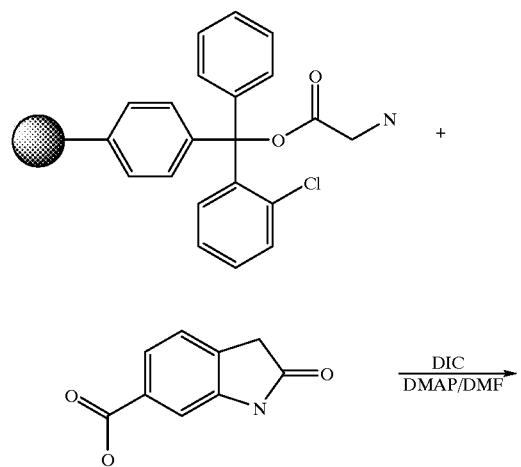

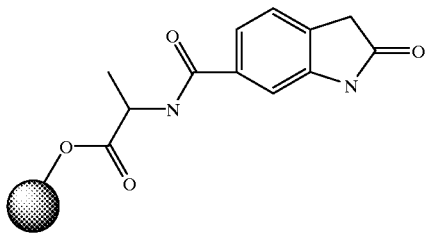

Starting oxindole (1.7 g, 2 eq) was dissolved in 68 mL DMF under nitrogen. Diisopropylcarbodiimide (DIC) (1.5 mL, 2eq) was added followed by 234 mg (0.4 eq) of DMAP. Then resin (6.85 g, 4.798 mmol, 1 eq) was added and stirred gently overnight. Resin was filtered and washed with DMF, MeOH and DCM.

The solvent was remove under high vacuum. 7.45 g of resin was collected.

2. Condensation of the Resin with Aldehydes

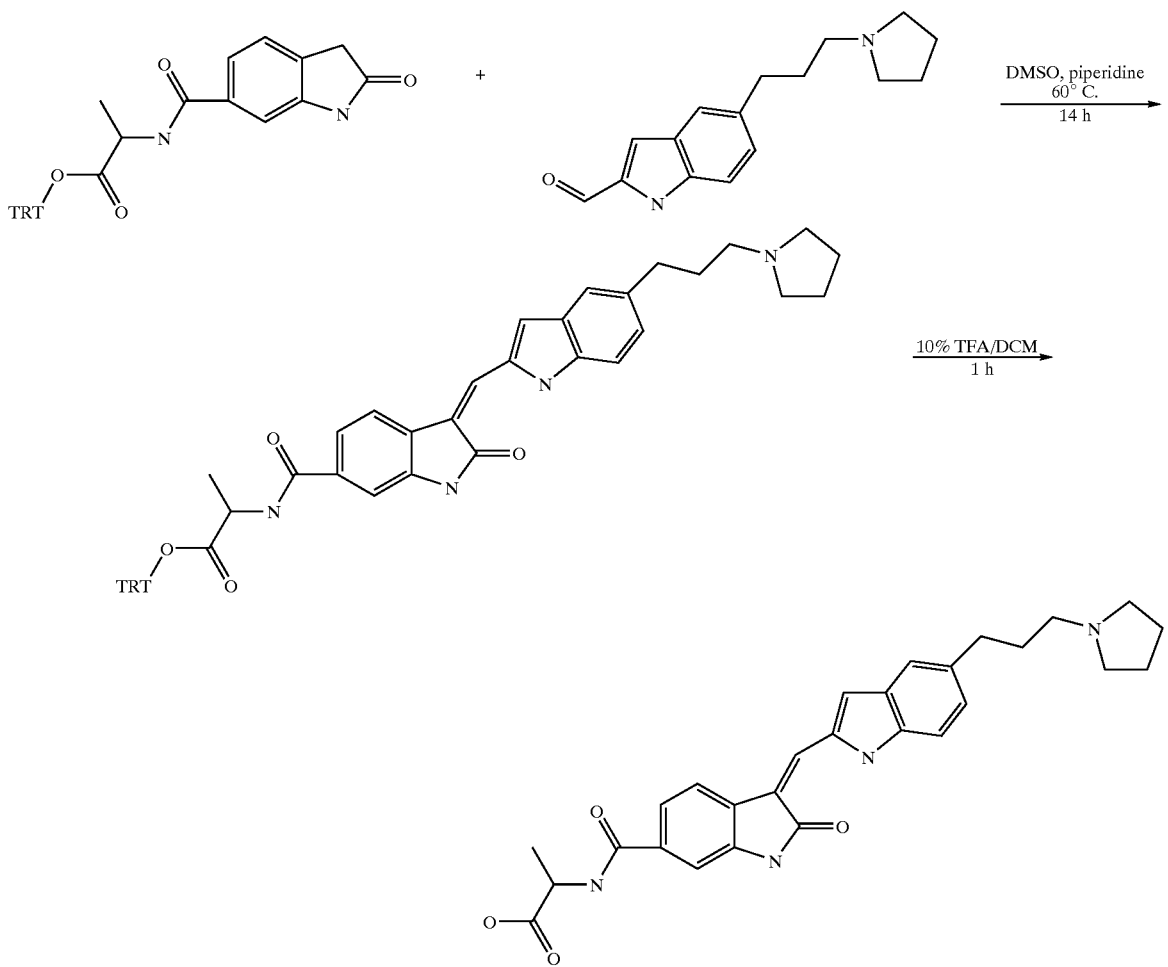

Resin (125 mg, 1 eq) was treated with aldehyde (1 mL of 0.2M solution in DMSO, 2 eq) and 1 mL of 50% piperidine in DMSO at 60° C. for 14 h. Resin was filtered and washed with DMSO, DMF, and MeOH. It was then treated to 1.5 mL of 10% TFA/DCM for 1 h. Resin was filtered again and washed with DMSO. Volatiles were removed from filtrate in vacuum.

Assay Procedures

The following in vitro assays may be used to determine the level of activity and effect of the different compounds of the present invention on one or more of the PKs. Similar assays can be designed along the same lines for any PK using techniques well known in the art.

Three general types of assays are useful for evaluating compounds: cellular/catalytic, cellular/biological and in vivo. The object of the cellular/catalytic assays is to determine the effect of a compound on the ability of a TK to phosphorylate tyrosines on a known substrate in a cell. The object of the cellular/biological assays is to determine the effect of a compound on the biological response stimulated by a TK in a cell. The object of the in vivo assays is to determine the effect of a compound in an animal model of a particular disorder such as cancer.

The cellular/catalytic assays described herein are performed in an ELISA format. The general procedure is a follows: a compound is introduced to cells expressing the test kinase, either naturally or recombinantly, for some period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound.

The cellular/biologic assays described herein measure the amount of DNA made in response to activation of a test kinase, which is a general measure of a proliferative response. The general procedure for this assay is as follows: a compound is introduced to cells expressing the test kinase, either naturally or recombinantly, for some period of time after which, if the test kinase is a receptor, a ligand known to activate the receptor is added. After incubation at least overnight, a DNA labeling reagent such as Bromodeoxyuridine (BrdU) or 3H-thymidine is added. The amount of labeled DNA is detected with either an anti-BrdU antibody or by measuring radioactivity and is compared to control cells not contacted with a test compound.

Cellular/Catalytic Assays

Enzyme linked immunosorbent assays (ELISA) may be used to detect and measure the presence of PK activity. The ELISA may be conducted according to known protocols which are described in, for example, Voller, et al., 1980, "Enzyme-Linked Immunosorbent Assay," In: *Manual of Clinical Immunology*, 2d ed., edited by Rose and Friedman, pp 359–371 Am. Soc. Of Microbiology, Washington, D.C.

The disclosed protocol may be adapted for determining activity with respect to a specific PK. For example, the preferred protocols for conducting the ELISA experiments for specific PKs is provided below. Adaptation of these protocols for determining a compound's activity for other members of the RTK family, as well as for CTKs and STKs, is well within the scope of knowledge of those skilled in the art.

Example 105

FLK-1

An ELISA assay was conducted to measure the kinase activity of the FLK-1 receptor and more specifically, the inhibition or activation of TK activity on the FLK-1 receptor. Specifically, the following assay was conducted to measure kinase activity of the FLK-1 receptor in cells genetically engineered to express Flk-1.

Materials and Methods

Materials

The following reagents and supplies were used:
a. Corning 96-well ELISA plates (Corning Catalog No. 25805-96);
b. Cappel goat anti-rabbit IgG (catalog no. 55641);
c. PBS (Gibco Catalog No. 450-1300EB);
d. TBSW Buffer (50 mM Tris (pH 7.2), 150 mM NaCl and 0.1% Tween-20);
e. Ethanolamine stock (10% ethanolamine (pH 7.0), stored at 4° C.);
f. HNTG buffer (20 mM HEPES buffer (pH 7.5), 150 mM NaCl, 0.2% Triton X-100, and 10% glycerol);
g. EDTA (0.5M (pH 7.0) as a 100×stock);
h. Sodium orthovanadate (0.5M as a 100×stock);
i. Sodium pyrophosphate (0.2M as a 100×stock);
j. NUNC 96 well V bottom polypropylene plates (Applied Scientific Catalog No. AS-72092);
k. NIH3T3 C7#3 Cells (FLK-1 expressing cells);
l. DMEM with 1×high glucose L-Glutamine (catalog No. 11965-050);
m. FBS, Gibco (catalog no. 16000-028);
n. L-glutamine, Gibco (catalog no. 25030-016);
o. VEGF, PeproTech, Inc. (catalog no. 100-20)(kept as 1 $\mu$g/100 $\mu$L stock in Milli-Q dH$_2$O and stored at −20° C.;
p. Affinity purified anti-FLK-1 antiserum;
q. UB40 monoclonal antibody specific for phosphotyrosine (see, Fendley, et al., 1990, *Cancer Research* 50:1550–1558);
r. EIA grade Goat anti-mouse IgG-POD (BioRad catalog no. 172-1011);
s. 2,2-azino-bis(3-ethylbenz-thiazoline-6-sulfonic acid (ABTS) solution (100 mM citric acid (anhydrous), 250 mM Na$_2$HPO$_4$ (pH 4.0), 0.5 mg/mL ABTS (Sigma catalog no. A-1888)), solution should be stored in dark at 4° C. until ready for use;
t. H$_2$O$_2$ (30% solution) (Fisher catalog no. H325);
u. ABTS/H$_2$O$_2$ (15 mL ABTS solution, 2 $\mu$L H$_2$O$_2$) prepared-5 minutes before use and left at room temperature;
v. 0.2M HCl stock in H$_2$O;
w. dimethylsulfoxide (100%) (Sigma Catalog No. D-8418); and
y. Trypsin-EDTA (Gibco BRL Catalog No. 25200-049).

Protocol

The following protocol was used for conducting the assay:
1. Coat Corning 96-well ELISA plates with 1.0 $\mu$g per well Cappel Anti-rabbit IgG antibody in 0.1 M Na$_2$CO$_3$ pH 9.6. Bring final volume to 150 $\mu$L per well. Coat plates overnight at 4° C. Plates can be kept up to two weeks when stored at 4° C.
2. Grow cells in Growth media (DMEM, supplemented with 2.0 mM L-Glutamine, 10% FBS) in suitable culture dishes until confluent at 37° C., 5% CO$_2$.

3. Harvest cells by trypsinization and seed in Corning 25850 polystyrene 96-well round bottom cell plates, 25.000 cells/well in 200 µL of growth media.
4. Grow cells at least one day at 37° C., 5% $CO_2$.
5. Wash cells with D-PBS 1×.
6. Add 200 µL/well of starvation media (DMEM, 2.0 mM 1-Glutamine, 0.1% FBS). Incubate overnight at 37° C., 5% $CO_2$.
7. Dilute Compounds 1:20 in polypropylene 96 well plates using starvation media. Dilute dimethylsulfoxide 1:20 for use in control wells.
8. Remove starvation media from 96 well cell culture plates and add 162 µL of fresh starvation media to each well.
9. Add 18 µL of 1:20 diluted Compound dilution (from step 7) to each well plus the 1:20 dimethylsulfoxide dilution to the control wells (+/− VEGF), for a final dilution of 1:200 after cell stimulation. Final dimethylsulfoxide is 0.5%. Incubate the plate at 37° C., 5% $CO_2$ for two hours.
10. Remove unbound antibody from ELISA plates by inverting plate to remove liquid. Wash 3 times with TBSW+0.5% ethanolamine, pH 7.0. Pat the plate on a paper towel to remove excess liquid and bubbles.
11. Block plates with TBSW+0.5% Ethanolamine, pH 7.0, 150 µL per well. Incubate plate thirty minutes while shaking on a microtiter plate shaker.
12. Wash plate 3 times as described in step 10.
13. Add 0.5 µg/well affinity purified anti-FLU-1 polyclonal rabbit antiserum. Bring final volume to 150 µL/well with TBSW+0.5% ethanolamine pH 7.0. Incubate plate for thirty minutes while shaking.
14. Add 180 µL starvation medium to the cells and stimulate cells with 20 µL/well 10.0 mM sodium ortho vanadate and 500 ng/mL VEGF (resulting in a final concentration of 1.0 mM sodium ortho vanadate and 50 ng/mL VEGF per well) for eight minutes at 37° C., 5% $CO_2$. Negative control wells receive only starvation medium.
15. After eight minutes, media should be removed from the cells and washed one time with 200 µL/well PBS.
16. Lyse cells in 150 µL/well HNTG while shaking at room temperature for five minutes. HNTG formulation includes sodium ortho vanadate, sodium pyrophosphate and EDTA.
17. Wash ELISA plate three times as described in step 10.
18. Transfer cell lysates from the cell plate to ELISA plate and incubate while shaking for two hours. To transfer cell lysate pipette up and down while scrapping the wells.
19. Wash plate three times as described in step 10.
20. Incubate ELISA plate with 0.02 µg/well UB40 in TBSW+05% ethanolamine. Bring final volume to 150 µL/well. Incubate while shaking for 30 minutes.
21. Wash plate three times as described in step 10.
22. Incubate ELISA plate with 1:10,000 diluted EIA grade goat anti-mouse IgG conjugated horseradish peroxidase in TBSW +0.5% ethanolamine, pH 7.0. Bring final volume to 150 µL/well. Incubate while shaking for thirty minutes.
23. Wash plate as described in step 10.
24. Add 100 µL of $ABTS/H_2O_2$ solution to well. Incubate ten minutes while shaking.
25. Add 100 µL of 0.2 M HCl for 0.1 M HCl final to stop the color development reaction. Shake 1 minute at room temperature. Remove bubbles with slow stream of air and read the ELISA plate in an ELISA plate reader at 410 nm.

Example 106

GST-FLK-1 Bioassay

This assay analyzes the tyrosine kinase activity of GST-Flk1 on poly glu tyr peptides.

Materials and Reagents

1. Corning 96-well Elisa plates (Corning Catalog No. 25805-96).
2. poly glu tyr 4:1, lyophilizate (Sigma Catalog # P0275). Prepare 1 mg/mL poly glu tyr in sterile PBS and store in 1 ml aliquots at −20° C.
3. Preparation of poly glu tyr (pEY) coated assay plates: Coat 2 µg/well of poly glu tyr (pEY) in 100 µL PBS at room temperature for 2 hours or at +4° C. overnight. Cover plates well to prevent evaporation.
4. PBS Buffer: To make 1 liter of a 1× working solution, mix 0.02 g $KH_2PO_4$, 1.15 g $NA_2HPO_4$, 0.2 g KCl and 8 g NaCl in approx. 900 mL $dH_2O$. When all reagents have dissolved, adjust the pH to 7.2 with HCl. Bring total volume to 1L with $dH_2O$.
5. PBS-Tw Buffer: To 1L of PBS Buffer, add 1/0 mL Tween-20. Stir until dissolved.
6. TBB-Blocking Buffer: To make one liter of a 1× working solution, mix 1.21 g TRIS, 8.77 g NaCl, 1 mL TWEEN-20 in approximately 900 mL dH2O. Adjust pH to 7.2 with HCl. Add 10 g BSA, stir to dissolve. Bring total volume to 1 L with $dH_2O$. Filter to remove particulate matter.
7. 1% BSA in PBS: To make a 1× working solution, add 10 g BSA to approx. 990 mL PBS buffer, stir to dissolve. Adjust total volume to 1 L with PBS buffer, filter to remove particulate matter.
8. 50 mM Hepes pH 7.5.
9. GST-Flk1cd purified from sf9 recombinant baculovirus transformation.
10. 4% DMSO in $dH_2O$.
11. 10 mM ATP in $dH_2O$.
12. 40 mM $MnCl_2$
13. Kinase Dilution Buffer (KDB): Mix 10 mL Hepes (pH 7.5), 1 mL of 5 M NaCl, 40 µL of 100 mM $NaVO_4$ and 0.4 mL of 5% BSA in $dH_2O$ with 88.56 mL of $dH_2O$.
14. NUNC-96-well V bottom polypropylene plates Applied Scientific Catalog # AS-72092
15. EDTA: Mix 14.12 g ethylenediaminetetraacetic acid (EDTA) to approx. 70 mL $dH_2O$. Add 10N NaOH until EDTA dissolves. Adjust pH to 8.0. Adjust total volume to 100 mL with $dH_2O$.
16. 1° Antibody Dilution Buffer: Mix 10 mL of 5% BSA in PBS buffer with 89.5 mL TBSTw.
17. Anti-phosphotyrosine monoclonal conjugated to horseradish peroxidase (PY99 HRP, Santa Cruz Biotech).
18. 2,2'-Azino-bis(3-ethylbenzthiazoline-6-sulfonic acid (ABTS, Moss, Cat. No. ABST).
19. 10% SDS.

Procedure

1. Coat Corning 96 well ELISA plates with 2 µg of polyEY peptide in sterile PBS as described in step 3 of Materials and Reagents.

2. Remove unbound liquid from wells by inverting plate. Wash once with TBSTw. Pat the plate on a paper towel to remove excess liquid.
3. Add 100 µL of 1% BSA in PBS to each well. Incubate, with shaking, for 1 hr. at room temperature.
4. Repeat step 2.
5. Soak wells with 50 mM Hepes pH7.5 (150 µL/well).
6. Dilute test compound with $dH_2O$/4% DMSO to 4 times the desired final assay concentration in 96-well polypropylene plates.
7. Add 25 µL diluted test compound to ELISA plate. To control wells (wells which do not receive any test compound), add 25 µL of $dH_2O$/4% DMSO.
8. Add 25 µL of 40 mM $MnCl_2$ with 4×ATP (2 µM) to all wells.
9. Add 25 µL 0.5 M EDTA to negative control wells.
10. Dilute GST-Flk1 0.005 µg (5 ng)/well in KDB. For 50 ml KDB add 100 µL of 0.050 mg/mL GST-Flk1 enzyme.
11. Add 50 µL of diluted enzyme to each well.
12. Incubate, with shaking, for 15 minutes at room temperature.
13. Stop reaction by adding 50 µL of 250 mM EDTA (pH 8.0).
14. Wash 3× with TBSTw and pat plate on paper towel to remove excess liquid.
15. Add 100 µL per well anti-phosphotyrosine HRP conjugate, 1:5,000 dilution in antibody dilution buffer. Incubate, with shaking for 90 min. at room temperature.
16. Wash as described above in step 14.
17. Add 100 µL of room temperature ABTS solution to each well.
18. Incubate, with shaking, for 10 to 15 minutes. Remove any bubbles.
19. Stop reaction by adding 20 µL of 10% SDS.
20. Read assay on Dynatech MR7000 ELISA reader: test filter at 410 nM; reference filter at 630 nM.

Example 107

PYK2 Bioassay

This assay is used to measure the in vitro kinase activity of HA epitope tagged full length pyk2 (FL.pyk2-HA) in an ELISA assay.

Materials and Reagents
1. Corning 96-well Elisa plates (Corning Catalog #25805-96).
2. 12CA5 monoclonal anti-HA antibody
3. PBS (Dulbecco's Phosphate-Buffered Saline, Gibco Catalog #450-1300EB)
4. TBST Buffer: Mix 8.766 g NaCl, 6.057 g TRIS and 1 ml of 0.1% Triton X-100 in approx. 900 mL $dH_2O$. Adjust pH to 7.2, bring volume to 1 L.
5. Blocking Buffer: Mix 100 g of 10% BSA, 12.1 g of 100 mM TRIS, 58.44 g of 1 M NaCl and 10 mL of 1% TWEEN-20.
6. FL.pyk2-HA from sf9 cell lysates.
7. 4% DMSO in MilliQue $H_2O$.
8. 10 mM ATP in $dH_2O$.
9. 1 M $MnCl_2$.
10. 1 M $MgCl_2$.
11. 1 M Dithiothreitol (DTT).
12. 10× Kinase buffer phosphorylation mix: Mix 5.0 mL 1 M Hepes (pH 7.5), 0.2 mL 1 M $MnCl_2$, 1.0 mL $MgCl_2$, 1.0 mL 10% Triton X-100 in 2.8 ml dH2O. Just prior to use, add 0.1 mL 1 M DTT.
13. NUNC-96-well V bottom polypropylene plates (Applied Scientific Catalog #AS 72092).
14. EDTA
15. Biotin conjugated anti-phosphotyrosine mab (Upstate Biotechnology Inc., clone-4G10 cat.#16-103, ser. #14495).
16. Vectastain Elite ABC reagent (Avidin peroxidase conjugate, Vector Laborotories (PK-6100).
17. ABTS Solution: Mix 19.21 g citric acid and 35.49 g $Na_2HPO_4$ in approx. 900 mL $dH_2O$. Adjust pH to 4.0 with phosphoric acid. Add 5 or 10 g ABST. When all dissolved, filter.
18. Hydrogen peroxide 30% solution.
19. ABTS/$H_2O_2$: Mix 15 mL ABTS solution with 3 µL 30% $H_2O_2$ 5 min. before use.
20. 0.2 M HCl.

Procedure
1. Coat Corning 96 well ELISA plates with 0.5 µg per well 12CA5 anti-HA antibody in 100 µL PBS. Store overnight at 4° C.
2. Remove unbound HA antibody from wells by inverting plate. Pat the plate on a paper towel to remove excess liquid.
3. Add 150 µL Blocking Buffer to each well. Incubate, with shaking, for 1 hr at room temperature.
4. Wash plates with TBS-T.
5. Dilute lysate in PBS (1.5 µg lysate/100 µL PBS).
6. Add 100 µL of diluted lysate to each well. Shake at room temperature for 1 hr.
7. Wash as in step 4.
8. Add 50 µL of 2× kinase Buffer to ELISA plate containing captured pyk2-HA.
9. Add 25 µL of 40 µM test compound in 4% DMSO or 4% DMSO alone (control) to plate.
10. Add 25 µL of 0.5 M EDTA to negative control wells.
11. Add 25 µL of 20 µM ATP to all wells. Incubate, with shaking, for 10 minutes.
12. Stop reaction by adding 25 µL 500 mM EDTA (pH 8.0) to all wells.
13. Wash as in step 4.
14. Add 100 µL biotin conjugated anti-phosphotyrosine mab (1:5000 dilution in Blocking Buffer) to each well. Incubate, with shaking for 30 min. at room temperature.
15. Make up Vectastain ABC reagent. Allow 30 min. for complete coupling of the avidin with the biotinylated HRP. Add 1 drop (or 50 µL) reagent A to 15 mL Blocking Buffer. Mix by inverting tube several times. Add 1 drop (or 50 µL)reagent B and mix again. Allow ABC reagent to mix at room temperature while the biotin-4G10 anti-phosphotyrosine is incubating in the assay plate.
16. Wash as in step 4.
17. Add 100 µL per well of prepared Vectastain peroxidase conjugate. Incubate, with shaking, for 30 min. at room temperature.
18. Wash as in step 4, then was once with PBS.
19. Add 100 µL of ABTS/$H_2O_2$ solution to each well.

20. Incubate, with shaking, for 10 to 15 minutes. Remove any bubbles.
21. If necessary, stop reaction with the addition of 100 μL of 0.2 M HCl per well.
22. Read assay on Dynatech MR7000 ELISA reader with test filter at 410 nM and reference filter at 630 nM.

Example 108
FGFR1 Bioassay

This assay is used to measure the in vitro kinase activity of FGF1–R in an ELISA assay.

Materials and Reagents
1. Costar 96-well Elisa plates (Corning Catalog #3369).
2. Poly(Glu,Tyr) (Sigma Catalog #P0275).
3. PBS (Gibco Catalog #450-1300EB)
4. 50 mM Hepes Buffer Solution.
5. Blocking Buffer (5% BSA/PBS).
6. Purified GST-FGFR1.
7. Kinase Dilution Buffer: Mix 500 μL 1 M Hepes (GIBCO), 20 μL 5% BSA/PBS, 10 μL 100 mM sodium orthovanadate and 50 μL 5 M NaCl.
8. 10 mM ATP
9. 1 M $MnCl_2$
10. $ATP/MnCl_2$ phosphorylation mix: Mix 20 μL ATP, 400 μL $MnCl_2$ and 9.56 mL $dH_2O$.
11. NUNC 96-well V bottom polypropylene plates (Applied Scientific Catalog #AS 72092).
12. 0.5 M EDTA.
13. 0.05% TBST: Add 500 μL TWEEN to 1 liter TBS.
14. Rabbit polyclonal anti-phosphotyrosine serum.
15. Goat anti-rabbit IgG peroxidase conjugate (Biosource, Catalog #ALI0404).
16. ABTS Solution
17. 30% Hydrogen peroxide.
18. $ABTS/H_2O_2$ Procedure
1. Coat Costar 96 well ELISA plates with 1 μg per well Poly(Glu,Tyr) in 100 μL PBS. Store overnight at 4° C.
2. Wash coated plates once with PBS.
3. Add 150 μL of 5% BSA/PBS Blocking Buffer to each well. Incubate, with shaking, for 1 hr. room temperature.
4. Wash plate 2x with PBS, then once with 50 mM Hepes. Pat plates on a paper towel to remove excess liquid and bubbles.
5. Add 25 μL of 0.4 mM test compound in 4% DMSO or 4% DMSO alone (controls) to plate.
6. Dilute purified GST-FGFR1 in Kinase Dilution Buffer (5 ng kinase/50 μL KDB/well).
7. Add 50 μL of diluted kinase to each well.
8. Start kinase reaction by adding 25 μL /well of freshly prepared $ATP/Mn^{++}$(0.4 mL 1 M $MnCl_2$, 40 μL 10 mM ATP, 9.56 mL $dH_2O$), freshly prepared).
9. This is a fast kinase reaction and must be stopped with 25 μL of 0.5M EDTA in a manner similar to the addition of ATP.
10. Wash plate 4x with fresh TBST.
11. Make up Antibody Dilution Buffer: Per 50 mL: Mix 5 ml of 5% BSA, 250 μL of 5% milk and 50 μL of 100 mM sodium vanadate, bring to final volume with 0.05% TBST.
12. Add 100 μl per well of anti-phosphotyrosine (1:10000 dilution in ADB). Incubate, with shaking for 1 hr. at room temperature.
13. Wash as in step 10.
14. Add 100 μL per well of Biosource Goat anti-rabbit IgG peroxidase conjugate (1:6000 dilution in ADB). Incubate, with shaking for 1 hr. at room temperature.
15. Wash as in step 10 and then with PBS to remove bubbles and excess TWEEN.
16. Add 100 μL of $ABTS/H_2O_2$ solution to each well.
17. Incubate, with shaking, for 10 to 20 minutes. Remove any bubbles.
18. Read assay on Dynatech MR7000 ELISA reader: test filter at 410 nM, reference filter at 630 nM.

Example 109
Cellular HER-2 Kinase Assay

This assay is used to measure HER-2 kinase activity in whole cells in an ELISA format.

Materials and Reagents
1. DMEM (GIBCO Catalog #11965-092).
2. Fetal Bovine Serum (FBS, GIBCO Catalog #16000-044), heat inactivated in a water bath for 30 min. at 56° C.
3. Trypsin (GIBCO Catalog #25200-056).
4. L-Glutamine (GIBCO Catalog #25030-081).
5. HEPES (GIBCO Catalog #15630-080).
6. Growth Media: Mix 500 mL DMEM, 55 mL heat inactivated FBS, 10 mL HEPES and 5.5 ml L-Glutamine.
7. Starve Media: Mix 500 mL DMEM, 2.5 ml heat inactivated FBS, 10 mL HEPES and 5.5 mL L-Glutamine.
8. PBS.
9. Flat Bottom 96-well Tissue Culture Micro Titer Plates (Coming Catalog #25860).
10. 15 cm Tissue Culture Dishes (Corning Catalog #08757148).
11. Corning 96-well ELISA Plates.
12. NUNC-96-well V bottom polypropylene plates.
13. Costar Transfer Cartidges for the Transtar 96 (Costar Catalog #7610).
14. SUMO 1: monoclonal anti-EGFR antibody.
15. TBST Buffer
16. Blocking Buffer: 5% Carnation Instant Milk® in PBS.
17. EGF Ligand: EGF-201, Shinko American, Japan. Suspend powder in 100 μL of 10 mM HCl. Add 100 μL 10 mM NaOH. Add 800 μL PBS and transfer to an Eppendorf tube for storage at −20° C.
18. HNTG Lysis Buffer:

For Stock 5xHNTG: Mix 23.83 g Hepes, 43.83 g NaCl, 500 mL glycerol and 100 mL Triton X-100 and enough $dH_2O$ to make 1 L of total solution.

For 1xHNTG*: Mix 2 mL HNTG, 100 μL 0.1 M $Na_3VO_4$, 250 μL 0.2M $Na_4P_2O_7$ and 100 μL EDTA.
19. EDTA
20. $Na_3VO_4$:

To make stock solution: Mix 1.84 g $Na_3VO_4$ with 90 mL $dH_2O$. Adjust pH to 10. Boil in microwave for one minute (solution becomes clear). Cool to room temperature. Adjust pH to 10. Repeat heating/cooling cycle until pH remains at 10.

21. 200 mM $Na_4P_2O_7$.
22. Rabbit polyclonal antiserum specific for phosphotyrosine (anti-Ptyr antibody).
23. Affinity purified antiserum, goat anti-rabbit IgG antibody, peroxidase conjugate (Biosource Cat #AL10404).
24. ABTS Solution
25. 30% Hydrogen peroxide solution.
26. $ABTS/H_2O_2$
27. 0.2 M HCl Procedure 1. Coat Corning 96 well ELISA plates with SUMO1 at 1.0 µg per well in PBS, 100 µL final volume/well. Store overnight at 4° C.
2. On day of use, remove coating buffer and wash plate 3 times with $dH_2O$ and once with TBST buffer. All washes in this assay should be done in this manner, unless otherwise specified.
3. Add 100 µL of Blocking Buffer to each well. Incubate plate, with shaking, for 30 min. at room temperature. Just prior to use, wash plate as described above.
4. Use EGFr/HER-2 chimera/3T3-C7 cell line for this assay.
5. Choose dishes having 80–90% confluence. Collect cells by trypsinization and centrifuge at 1000 rpm at room temperature for 5 min.
6. Resuspend cells in starve medium and count with trypan blue. Viability above 90% is required. Seed cells in starve medium at a density of 2,500 cells per well, 90 µL per well, in a 96 well microtiter plate. Incubate seeded cells overnight at 37° C. under 5% $CO_2$.
7. Start the assay two days after seeding.
8. Test compound dilution:

Primary Screening

Samples are diluted directly into a polypropylene plate containing starve-DMEM. This dilution will be 1:10 or greater, depending on the samples being screened. The same amount of DMSO is put into the control wells. All wells are then transferred to the cell plate at a 1:10 dilution (10 µL of sample and media into 90 µL of starve media). The final DMSO concentration will be 1% or lower.

Secondary screening

Ten samples are put into wells 2–11 of row A of a polypropylene plate. These wells contain straight starve-DMEM. For a 1:10 dilution, use 10 µL of test compound solution in 90 ul of media. The rest of the wells (including control) will have a DMSO/media mixture. The percentage of DMSO in this mixture is determined by the first dilution factor, e.g., in this example, 1:10. The DMSO concentration is therefore 10%. An equal amount of drug and media from row A is put into row B, containing DMSO and media. The same amount is then taken out and put into row C, etc. These are 1:2 dilutions. All wells are then transferred to the cell plate at 1:10 dilution (10 µL of sample and media into 90 µL of starve media). The final DMSO concentration will be 1% or lower.

9. Incubate under 5% $CO_2$ at 37° C. for 2 hours.
10. Prepare EGF ligand by diluting stock EGF (16.5 µM) in warm DMEM to 150 nM.
11. Prepare fresh HNTG* sufficient for 100 µL per well; place on ice.
12. After 2 hour incubation with test compound, add prepared EGF ligand to cells, 50 ul per well, for a final concentration of 50 nM. Positive control wells receive the same amount of EGF. Negative controls do not receive EGF. Incubate at 37° C. for 10 min.
13. Remove test compound, EGF, and DMEM. Wash cells once with PBS.
14. Transfer HNTG* to cells, 100 µL per well. Place on ice for 5 minutes. Meanwhile, remove blocking buffer from ELISA plate and wash.
15. With a pipette tip securely fitted to a micropipettor, scrape cells from plate and homogenize cell material by repeatedly aspirating and dispensing the HNTG* lysis buffer. Transfer lysate to a coated, blocked, washed ELISA plate. Alternatively, one may use a Costar transfer cartridge to transfer lysate to the ELISA plate.
16. Incubate, with shaking, at room temperature for one hr.
17. Remove lysate, wash. Transfer freshly diluted anti-Ptyr antibody (1:3000 in TB ST) to ELISA plate, 100 µL per well.
18. Incubate, with shaking, at room temperature, for 30 min.
19. Remove anti-Ptyr antibody, wash. Transfer freshly diluted BIOSOURCE antibody to ELISA plate (1:8000 in TBST, 100 µL per well).
20. Incubate, with shaking, at room temperature for 30 min.
21. Remove BIOSOURCE antibody, wash. Transfer freshly prepared $ABTS/H_2O_2$ solution to ELISA plate, 100 µL per well.
22. Incubate, with shaking, for 5–10 minutes. Remove any bubbles.
23. If necessary, stop reaction with the addition of µL of 0.2 M HCl per well.
24. Read assay on Dynatech MR7000 ELISA reader: test filter set at 410 nM; reference filter at 630 nM.

Example 110

CDK2/Cyclin A Assay

The following protocol describes the procedures used to analyze protein serine/threonine kinase activity of cdk2/cyclin A in an SPA. The procedure also describes the protocol for the initial screening of drugs for inhibition or activation of the kinase activity.

Materials and Reagents

1. Wallac 96-well polyethylene terephthalate (flexi) plates (Wallac Catalog #1450-401).
2. Amersham Redivue [$\gamma^{33}P$] ATP (Amersham catalog #AH-9968).
3. Amersham streptavidin coated polyvinyltoluene SPA beads (Amersham catalog #RPNQ0007). Reconstitute beads in PBS without magnesium or calcium, at 20 mg/mL. Store reconstituted beads at 4° C.
4. Activated cdk2/cyclin A enzyme complex purified from Sf9 cells, −80° C., 200 µL aliquots
5. Biotinylated peptide substrate (deb-tide). Peptide biotin-X-PKTPKKAKKL dissolved in $dH_2O$ at a concentration of 5 mg/mL. Stored at −80° C. in 100 µL aliquots.

6. Peptide/ATP Mixture:

| Reagent | Stock Concentration | 2.5 × Working Concentration | Amount per 10 mL | Final Well Concentration |
|---|---|---|---|---|
| dH$_2$O | | 10 mL | 9.979 mL | — |
| Cold ATP | 10 mM | 1.25 μM | 0.00125 mL | 0.5 μM |
| Debtide | 5 mg/mL | 0.005 mg/mL | 0.010 mL | 0.1 μg/well |
| γ$^{33}$P ATP | 10 μCi/μL | 10 μCi/mL | 0.010 mL | 0.2 μCi/well |

7. 2.5 ×kinase buffer

| Reagent | Stock solution | Amount per 10 mL | Working Concentration | Final Well Concentration |
|---|---|---|---|---|
| dH$_2$O | 55.5 M | 8.85 mL | | — |
| Tris pH7.4 | 1 M | 0.625 mL | 62.5 mM | 25 mM TRIS |
| MgCl$_2$ | 1 M | 0.25 mL | 25 mM | 10 mM MgCl$_2$ |
| NP40 | 10% | 0.25 mL | 0.25% | 0.1% NP40 |
| *DTT add fresh | 1 M | 0.025 mL | 2.5 mM | 1 mM DTT |

8. 10 mM ATP (Sigma Catalog #A-5394).
9. 1 M Tris, pH 7.4
10. 1 M MgCl$_2$
11. 1 M DTT
12. PBS (Dulbecco's Phosphate-Buffered Saline) without magnesium or calcium (Gibco Catalog #14190-144)
13. EDTA (14.12 g per 100 mL).
14. Stop solution:

| Reagent | Stock solution | Amount per 10 mL | Working Concentration |
|---|---|---|---|
| PBS | | 9.25 mL | |
| ATP | 100 mM | 0.005 mL | 50 uM |
| EDTA | 0.5 M | 0.1 mL | 5 mM |
| Triton X-100 | 10% | 0.1 mL | 0.1% |
| SPA beads | 20 mg/ml | 1.25 mL | 0.5 mg/well (200 μL) |

Procedure

1. Prepare solutions of inhibitors at 5× the desired final concentration in 5% DMSO. Add 10 μL to each well. For negative controls, add 10 μL 5% DMSO.
2. Dilute 5 μL of cdk2/cyclin A solution into 2.1 mL 2× kinase buffer (per plate).
3. Add 20 μL enzyme per well. This can be added using a hand pipette or by using the Titertek Multidrop.
4. Add 10 μL of 0.5 M EDTA to the neagtive control wells.
5 . To start kinase reaction, add 20 μL of peptide/ATP mixture using either a hand pipette or the Titertek Multidrop. Let sit on benchtop behind reactive shield for 1 hr.
6. Add 200 μL stop solution per well using either the Titertek Multidrop or hand pipette.
7. Let stand at least 10 min.
8. Spin plate approx. 2300 rpm 3–5 min.
9. Count plate on Trilux reader using protocol #28 (Brian's SPA assay).

Example 111

PDGF-R ELISA

All cell culture media, glutamine, and fetal bovine serum were purchased from Gibco Life Technologies (Grand Island, N.Y.) unless otherwise specified. All cells were grown in a humid atmosphere of 90–95% air and 5–10% CO$_2$ at 37° C. All cell lines were routinely subcultured twice a week and were negative for mycoplasma as determined by the Mycotect method (Gibco).

For ELISA assays, cells (U1242, obtained from Joseph Schlessinger, NYU) were grown to 80–90% confluency in growth medium (MEM with 10% FBS, NEAA, 1 mM NaPyr and 2 mM GLN) and seeded in 96-well tissue culture plates in 0.5% serum at 25,000 to 30,000 cells per well. After overnight incubation in 0.5% serum-containing medium, cells were changed to serum-free medium and treated with test compound for 2 hr in a 5% CO$_2$, 37° C. incubator. Cells were then stimulated with ligand for 5–10 minute followed by lysis with HNTG (20 mM Hepes, 150 mM NaCl, 10% glycerol, 5 mM EDTA, 5 mM Na$_3$VO$_4$, 0.2% Triton X-100, and 2 mM NaPyr). Cell lysates (0.5 mg/well in PBS) were transferred to ELISA plates previously coated with receptor-specific antibody and which had been blocked with 5% milk in TBST (50 mM Tris-HCl pH 7.2, 150 mM NaCl and 0.1% Triton X-100) at room temperature for 30 min. Lysates were incubated with shaking for 1 hour at room temperature. The plates were washed with TBST four times and then incubated with polyclonal anti-phosphotyrosine antibody at room temperature for 30 minutes. Excess anti-phosphotyrosine antibody was removed by rinsing the plate with TBST four times. Goat anti-rabbit IgG antibody was added to the ELISA plate for 30 min at room temperature followed by rinsing with TBST four more times. ABTS (100 mM citric acid, 250 mM Na$_2$HPO$_4$ and 0.5 mg/mL 2,2'-azino-bis(3-ethylbenzthiazoline-6-sulfonic acid)) plus H$_2$O$_2$ (1.2 mL 30% H$_2$O$_2$ to 10 mL ABTS) was added to the ELISA plates to start color development. Absorbance at 410 nm with a reference wavelength of 630 mn was recorded about 15 to 30 min after ABTS addition.

Example 112

IGF-I Receptor Elisa

The following protocol may be used to measure phosphotyrosine level on IGF-I receptor, which indicates IGF-I receptor tyrosine kinase activity.

Materials and Reagents

The following materials and reagents were used:

a. The cell line used in this assay is 3T3/IGF-1R, a cell line genetically engineered to overexpresses IGF-1 receptor.
b. NIH3T3/IGF-1R is grown in an incubator with 5% CO$_2$ at 37° C. The growth media is DMEM+10% FBS (heat inactivated)+2 mM L-glutamine.
c. Affinity purified anti-IGF-1R antibody-17-69.
d. D-PBS:

| | |
|---|---|
| KH$_2$PO$_4$ | 0.20 g/L |
| K$_2$HPO$_4$ | 2.16 g/L |
| KCl | 0.20 g/L |
| NaCl | 8.00 g/L (pH 7.2) | e. Blocking Buffer: TBST plus-5% Milk (Carnation Instant Non-Fat Dry Milk).

f. TBST buffer:

| | |
|---|---|
| Tris-HCl | 50 mM |
| NaCl | 150 mM (pH 7.2/HCl 10 N) |
| Triton X-100 | 0.1% |

Stock solution of TBS (10×) is prepared, and Triton X-100 is added to the buffer during dilution.
g. HNTG buffer:

| | |
|---|---|
| HEPES | 20 mM |
| NaCl | 150 mM (pH 7.2/HCl 1N) |
| Glycerol | 10% |
| Triton X-100 | 0.2% |

Stock solution (5×) is prepared and kept at 4° C.
h. EDTA/HCl: 0.5 M pH 7.0 (NaOH) as 100×stock.
i. $Na_3VO_4$: 0.5 M as 100×stock and aliquots are kept in −80° C.
j. Na4P2O7: 0.2 M as 100×stock.
k. Insulin-like growth factor-1 from Promega (Cat#G5111).
l. Rabbit polyclonal anti-phosphotyrosine antiserum.
m. Goat anti-rabbit IgG, POD conjugate (detection antibody), Tago (Cat. No. 4520, Lot No. 1802): Tago, Inc., Burlingame, Calif.
n. ABTS (2,2'-azinobis(3-ethylbenzthiazolinesulfonic acid)) solution:

| | |
|---|---|
| Citric acid | 100 mM |
| $Na_2HPO_4$ | 250 mM (pH 4.0/1 N HCl) |
| ABTS | 0.5 mg/mL |

ABTS solution should be kept in dark and 4° C. The solution should be discarded when it turns green.
  o. Hydrogen Peroxide: 30% solution is kept in the dark and at 4° C.
Procedure
All the following steps are conducted at room temperature unless it is specifically indicated. All ELISA plate washings are performed by rinsing the plate with tap water three times, followed by one TBST rinse. Pat plate dry with paper towels.
A. Cell Seeding
  1. The cells, grown in tissue culture dish (Corning 25020-100) to 80–90% confluence, are harvested with Trypsin-EDTA (0.25%, 0.5 mL/D-100, GIBCO).
  2. Resuspend the cells in fresh DMEM+10% FBS+2 mM L-Glutamine, and transfer to 96-well tissue culture plate (Corning, 25806-96) at 20,000 cells/well (100 μL/well). Incubate for 1 day then replace medium to serum-free medium (90/μL) and incubate in 5% $CO_2$ and 37° C. overnight.
B. ELISA Plate Coating and Blocking
  1. Coat the ELISA plate (Corning 25805-96) with Anti-IGF-1R Antibody at 0.5 μg/well in 100 μL PBS at least 2 hours.
  2. Remove the coating solution, and replace with 100 μL Blocking Buffer, and shake for 30 minutes. Remove the blocking buffer and wash the plate just before adding lysate.

C. Assay Procedures
  1. The drugs are tested in serum-free condition.
  2. Dilute drug stock (in 100% DMSO) 1:10 with DMEM in 96-well poly-propylene plate, and transfer 10 μL/well of this solution to the cells to achieve final drug dilution 1:100, and final DMSO concentration of 1.0%. Incubate the cells in 5% $CO_2$ at 37° C. for 2 hours.
  3. Prepare fresh cell lysis buffer (HNTG*)

| | |
|---|---|
| HNTG | 2 mL |
| EDTA | 0.1 mL |
| $Na_3VO_4$ | 0.1 mL |
| $Na_4(P_2O_7)$ | 0.1 mL |
| $H_2O$ | 7.3 mL |

4. After drug incubation for two hours, transfer-10 □l/well of 200nM IGF-1 Ligand in PBS to the cells (Final Conc.=20 nM), and incubate at 5% $CO_2$ at 37° C. for 10 minutes.
  5. Remove media and add 100 μL/well HNTG* and shake for 10 minutes. Look at cells under microscope to see if they are adequately lysed.
  6. Use a 12-channel pipette to scrape the cells from the plate, and homogenize the lysate by repeated aspiration and dispensing. Transfer all the lysate to the antibody coated ELISA plate, and shake for 1 hour.
  7. Remove the lysate, wash the plate, transfer anti-pTyr (1:3,000 with TBST) 100 μL/well, and shake for 30 minutes.
  8. Remove anti-pTyr, wash the plate, transfer TAGO (1:3,000 with TBST) 100 μL/well, and shake for 30 minutes.
  9. Remove detection antibody, wash the plate, and transfer fresh ABTS/$H_2O_2$ (1.2 μL $H_2O_2$ to 10 ml ABTS)-100 μL/well to the plate to start color development.
  10. Measure OD at 410 nm with a reference wavelength of 630 nm in Dynatec MR5000.

Example 113

EGF Receptor ELISA

EGF Receptor kinase activity in cells genetically engineered to express human EGF-R was measured as described below:
Materials and Reagents
  The following materials and reagents were used:
  a. EGF Ligand: stock concentration=16.5 μM; EGF 201, TOYOBO, Co., Ltd. Japan.
  b. 05-101 (UBI) (a monoclonal antibody recognizing an EGFR extracellular domain).
  c. Anti-phosphotyrosine antibody (anti-Ptyr) (polyclonal).
  d. Detection antibody: Goat anti-rabbit lgG horse radish peroxidase conjugate, TAGO, Inc., Burlingame, Calif.
  e. TBST buffer:

| | |
|---|---|
| Tris-HCl, pH 7 | 50 mM |
| NaCl | 150 mM |
| Triton X-100 | 0.1 | f. HNTG-5×stock:

| HEPES | 0.1 M |
|---|---|
| NaCl | 0.75 M |
| Glycerol | 50 |
| Triton X-100 | 1.0% | g. ABTS stock:

| Citric Acid | 100 mM |
|---|---|
| Na$_2$HPO$_4$ | 250 mM |
| HCl, conc. | 4.0 pH |
| ABTS* | 0.5 mg/mL |

Keep solution in dark at 4° C. until used.

h. Stock reagents of:

| EDTA | 100 mM pH 7.0 |
|---|---|
| Na$_3$VO$_4$ | 0.5 M |
| Na$_4$(P$_2$O$_7$) | 0.2 M |

Procedure

The following protocol was used:

A. Pre-coat ELISA Plate
 1. Coat ELISA plates (Corning, 96 well, Cat. #25805-96) with 05–101 antibody at 0.5 µg per well in PBS, 150 µL final volume/well, and store overnight at 4° C. Coated plates are good for up to 10 days when stored at 4° C.
 2. On day of use, remove coating buffer and replace with blocking buffer (5% Carnation Instant Non-Fat Dry Milk in PBS). Incubate the plate, shaking, at room temperature (about 23° C. to 25° C.) for 30 minutes. Just prior to use, remove blocking buffer and wash plate 4 times with TBST buffer.

B. Seeding Cells
 1. NIH 3T3/C7 cell line (Honegger, et al., Cell 51:199–209, 1987) can be use for this assay.
 2. Choose dishes having 80–90% confluence for the experiment. Trypsinize cells and stop reaction by adding 10% CS DMEM medium. Suspend cells in DMEM medium (10% CS DMEM medium) and centrifuge once at 1000 rpm at room temperature for 5 minutes.
 3. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 µL per well, in a 96 well microtiter plate. Incubate seeded cells in 5% CO$_2$ at 37° C. for about 40 hours.

C. Assay Procedures
 1. Check seeded cells for contamination using an inverted microscope. Dilute drug stock (10 mg/ml in DMSO) 1:10 in DMEM medium, then transfer 5 µL to a test well for a final drug dilution of 1:200 and a final DMSO concentration of 1%. Control wells receive DMSO alone. Incubate in 5% CO$_2$ at 37° C. for one hour.
 2. Prepare EGF ligand: dilute stock EGF in DMEM so that upon transfer of 10 µL dilute EGF (1:12 dilution), 25 nM final concentration is attained.
 3. Prepare fresh 10 ml HNTG* sufficient for 100 µL per well wherein HNTG* comprises: HNTG stock (2.0 mL), milli-Q H$_2$O (7.3 mL), EDTA, 100 mM, pH 7.0 (0.5 mL), Na$_3$VO$_4$ 0.5 M (0.1 mL) and Na$_4$(P$_2$O$_7$), 0.2 M (0.1 mL).
 4. Place on ice.
 5. After two hours incubation with drug, add prepared EGF ligand to cells, 10 µL per well, to yield a final concentration of 25 nM. Control wells receive DMEM alone. Incubate, shaking, at room temperature, for 5 minutes.
 6. Remove drug, EGF, and DMEM. Wash cells twice with PBS. Transfer HNTG* to cells, 100 µL per well. Place on ice for 5 minutes. Meanwhile, remove blocking buffer from other ELISA plate and wash with TBST as described above.
 7. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.
 8. Remove lysate and wash 4 times with TBST. Transfer freshly diluted anti-Ptyr antibody to ELISA plate at 100 µL per well. Incubate shaking at room temperature for 30 minutes in the presence of the anti-Ptyr antiserum (1:3000 dilution in TBST).
 9. Remove the anti-Ptyr antibody and wash 4 times with TBST. Transfer the freshly diluted TAGO 30 anti-rabbit IgG antibody to the ELISA plate at 100 µL per well. Incubate shaking at room temperature for 30 minutes (anti-rabbit IgG antibody: 1:3000 dilution in TBST).
 10. Remove detection antibody and wash 4 times with TBST. Transfer freshly prepared ABTS/H$_2$O$_2$ solution to ELISA plate, 100 µL per well. Incubate at room temperature for 20 minutes. ABTS/H$_2$O$_2$ solution: 1.2 µL 30% H$_2$O$_2$ in 10 mL ABTS stock.
 11. Stop reaction by adding 50 µL 5N H$_2$SO$_4$ (optional), and determine O.D. at 410 nm.
 12. The maximal phosphotyrosine signal is determined by subtracting the value of the negative controls from the positive controls. The percent inhibition of phosphotyrosine content for extract-containing wells is then calculated, after subtraction of the negative controls.

Example 114

Met Autophosphorylation Assay-ELISA

This assay determines Met tyrosine kinase activity by analyzing Met protein tyrosine kinase levels on the Met receptor.

Materials and Reagents

The following materials and reagents were used:
 a. HNTG (5×stock solution): Dissolve 23.83 g HEPES and 43.83 g NaCl in about 350 mL dH2O. Adjust pH to 7.2 with HCl or NaOH, add 500 mL glycerol and 10 mL Triton X-100, mix, add dH$_2$O to 1 L total volume. To make 1 L of 1×working solution add 200 mL 5×stock solution to 800 mL dH$_2$O, check and adjust pH as necessary, store at 4° C.
 b. PBS (Dulbecco's Phosphate-Buffered Saline), Gibco Cat. #450-1300EB (1×solution).
 c. Blocking Buffer: in 500 ml dH$_2$O place 100 g BSA, 12.1 g Tris-pH7.5, 58.44 g NaCl and 10 mL Tween-20, dilute to 1 L total volume.
 d. Kinase Buffer: To 500 mL dH$_2$O add 12.1 g TRIS pH7.2, 58.4 g NaCl, 40.7 g MgCl$_2$ and 1.9 g EGTA; bring to 1 L total volume with dH$_2$O.

e. PMSF (Phenylmethylsulfonyl fluoride), Sigma Cat. #P-7626, to 435.5 mg, add 100% ethanol to 25 mL total volume, vortex.
f. ATP (Bacterial Source), Sigma Cat. #A-7699, store powder at −20° C.; to make up solution for use, dissolve 3.31 mg in 1 mL dH$_2$O.
g. RC-20H HRPO Conjugated Anti-Phosphotyrosine, Transduction Laboratories Cat. #E120H.
h. Pierce 1-Step (TM) Turbo TMB-ELISA (3,3',5,5'-tetramethylbenzidine, Pierce Cat. #34022.
i. H$_2$SO$_4$, add 1 mL conc. (18N) to 35 mL dH$_2$O.
j. TRIS HCL, Fischer Cat. #BP152-5; to 121.14 g of material, add 600 mL MilliQ H$_2$O, adjust pH to 7.5 (or 7.2) with HCl, bring volume to 1 L with MilliQ H$_2$O.
k. NaCl, Fischer Cat. #S271-10, make up 5 M solution.
l. Tween-20, Fischer Cat. #S337-500.
m. Na$_3$VO$_4$, Fischer Cat. #S454-50, to 1.8 g material add 80 ml MilliQ H$_2$O, adjust pH to 10.0 with HCl or NaOH, boil in microwave, cool, check pH, repeat procedure until pH stable at 10.0, add MilliQ H$_2$O to 100 ml total volume, make 1 mL aliquots and store at −80° C.
n. MgCl$_2$, Fischer Cat. #M33-500, make up 1 M solution.
o. HEPES, Fischer Cat. #BP310–500, to 200 ml MilliQ H$_2$O, add 59.6 g material, adjust pH to 7.5, bring volume to 250 mL total, sterile filter.
p. Albumin, Bovine (BSA), Sigma Cat. #A-4503, to 30 grams material add sterile distilled water to make total volume of 300 mL, store at 4° C.
q. TBST Buffer: to approx. 900 mL dH$_2$O in a 1 L graduated cylinder add 6.057 g TRIS and 8.766 g NaCl, when dissolved, adjust pH to 7.2 with HCl, add 1.0 mL Triton X-100 and bring to 1 L total volume with dH$_2$O.
r. Goat Affinity purified antibody Rabbit IgG (whole molecule), Cappel Cat. #55641.
s. Anti h-Met (C-28) rabbit polyclonal IgG antibody, Santa Cruz Chemical Cat. #SC-161.
t. Transiently Transfected EGFR/Met chimeric cells (EMR) (Komada, et al., *Oncogene*, 8:2381–2390 (1993).
u. Sodium Carbonate Buffer, (Na$_2$CO$_4$, Fischer Cat. #S495): to 10.6 g material add 800 mL MilliQ H$_2$O, when dissolved adjust pH to 9.6 with NaOH, bring up to 1 L total volume with MilliQ H$_2$O, filter, store at 4° C.

Procedure

All of the following steps are conducted at room temperature unless it is specifically indicated otherwise. All ELISA plate washing is by rinsing 4× with TBST.

A. EMR Lysis

This procedure can be performed the night before or immediately prior to the start of receptor capture.
1. Quick thaw lysates in a 37° C. waterbath with a swirling motion until the last crystals disappear.
2. Lyse cell pellet with 1×HNTG containing 1 mM PMSF. Use 3 ml of HNTG per 15 cm dish of cells. Add ½ the calculated HNTG volume, vortex the tube for 1 min., add the remaining amount of HNTG, vortex for another min.
3. Balance tubes, centrifuge at 10,000×g for 10 min at 4° C.
4. Pool supernatants, remove an aliquot for protein determination.
5. Quick freeze pooled sample in dry ice/ethanol bath. This step is performed regardless of whether lysate will be stored overnight or used immediately following protein determination.
6. Perform protein determination using standard bicinchoninic acid (BCA) method (BCA Assay Reagent Kit from Pierce Chemical Cat. #23225).

B. ELISA Procedure
1. Coat Corning 96 well ELISA plates with 5 μg per well Goat anti-Rabbit antibody in Carbonate Buffer for a total well volume of 50 μL. Store overnight at 4° C.
2. Remove unbound Goat anti-rabbit antibody by inverting plate to remove liquid.
3. Add 150 μL of Blocking Buffer to each well. Incubate for 30 min. at room temperature with shaking.
4. Wash 4× with TBST. Pat plate on a paper towel to remove excess liquid and bubbles.
5. Add 1 μg per well of Rabbit anti-Met antibody diluted in TBST for a total well volume of 100 μL.
6. Dilute lysate in HNTG (90 μg lysate/100 μL)
7. Add 100 μL of diluted lysate to each well. Shake at room temperature for 60 min.
8. Wash 4× with TBST. Pat on paper towel to remove excess liquid and bubbles.
9. Add 50 μL of 1×lysate buffer per well.
10. Dilute compounds/extracts 1:10 in 1×Kinase Buffer in a polypropylene 96 well plate.
11. Transfer 5.5 μL of diluted drug to ELISA plate wells. Incubate at room temperature with shaking for 20 min.
12. Add 5.5 μL of 60 μM ATP solution per well. Negative controls do not receive any ATP. Incubate at room temperature for 90 min., with shaking.
13. Wash 4× with TBST. Pat plate on paper towel to remove excess liquid and bubbles.
14. Add 100 μL per well of RC20 (1:3000 dilution in Blocking Buffer). Incubate 30 min. at room temperature with shaking.
15. Wash 4× with TBST. Pat plate on paper towel to remove excess liquid and bubbles.
16. Add 100 μL per well of Turbo-TMB. Incubate with shaking for 30–60 min.
17. Add 100 μL per well of 1 M H$_2$SO$_4$ to stop reaction.
18. Read assay on Dynatech MR7000 ELISA reader. Test Filter=450 nm, reference filter 410 nm.

Example 115

Biochemical src assay ELISA

This assay is used to determine src protein kinase activity measuring phosphorylation of a biotinylated peptide as the readout.

Materials and Reagents

The following materials and reagents were used:
a. Yeast transformed with.
b. Cell lysates: Yeast cells expressing src are pelleted, washed once with water, re-pelleted and stored at −80° C. until use.
c. N-terminus biotinylated EEEYEEYEEEYEEEYEEEY is prepared by standard procedures well known to those skilled in the art.
d. DMSO: Sigma, St. Louis, Mo.
e. 96 Well ELISA Plate: Corning 96 Well Easy Wash, Modified flat Bottom Plate, Corning Cat. #25805-96.
f. NUNC-96-well V-bottom polypropylene plates for dilution of compounds: Applied Scientific Cat. #A-72092.

g. Vecastain ELITE ABC reagent: Vector, Burlingame, Calif.
h. Anti-src (327) mab: Schizosaccharomyces Pombe was used to express recombinant Src (Superti-Furga, et al., *EMBO J.*, 12:2625–2634; Superti-Furga, et al., *Nature Biochem.*, 14:600–605). S. Pombe strain SP200 (h-s leu1.32 ura4 ade210) was grown as described and transformations were pRSP expression plasmids were done by the lithium acetate method (Superti-Furga, supra). Cells were grown in the presence of 1 $\mu$M thiamine to repress expression from the nmt1 promoter or in the absence of thiamine to induce expression.
i. Monoclonal anti-phosphotyrosine, UBI 05-321 (UB40 may be used instead).
j. Turbo TMB-ELISA peroxidase substrate: Pierce Chemical.

Buffer Solutions
a. PBS (Dulbecco's Phosphate-Buffered Saline): GIBCO PBS, GIBCO Cat. #450-1300EB.
b. Blocking Buffer: 5% Non-fat milk (Carnation) in PBS.
c. Carbonate Buffer: $Na_2CO_4$ from Fischer, Cat. #S495, make up 100 mM stock solution.
d. Kinase Buffer: 1.0 mL (from 1 M stock solution) $MgCl_2$; 0.2 mL (from a 1 M stock solution) $MnCl_2$; 0.2 mL (from a 1 M stock solution) DTT; 5.0 ml (from a 1 M stock solution) HEPES; 0.1 mL TX-100; bring to 10 mL total volume with MilliQ $H_2O$.
e. Lysis Buffer: 5.0 HEPES (from 1 M stock solution.); 2.74 mL NaCl (from 5 M stock solution); 10 mL glycerol; 1.0 mL TX-100; 0.4 ml EDTA (from a 100 mM stock solution); 1.0 mL PMSF (from a 100 mM stock solution); 0.1 mL $Na_3VO_4$ (from a 0.1 M stock solution); bring to 100 mL total volume with MilliQ $H_2O$.
f. ATP: Sigma Cat. #A-7699, make up 10 mM stock solution (5.51 mg/mL).
g. TRIS-HCl: Fischer Cat. #BP-152-5, to 600 ml MilliQ $H_2O$ add 121.14 g material, adjust pH to 7.5 with HCl, bring to 1 L total volume with MilliQ $H_2O$.
h. NaCl: Fischer Cat. #S271-10, Make up SM stock solution with MilliQ $H_2O$.
i. $Na_3VO_4$: Fischer Cat. #S454-50; to 80 mL MilliQ $H_2O$, add 1.8 g material; adjust pH to 10.0 with HCl or NaOH; boil in a microwave; cool; check pH, repeat pH adjustment until pH remains stable after heating/ cooling cycle; bring to 100 mL total volume with MilliQ $H_2O$; make 1 mL aliquots and store at $-80°$ C.
j. $MgCl_2$: Fischer Cat. #M33-500, make up 1 M stock solution with MilliQ $H_2O$.
k. HEPES: Fischer Cat. #BP 310-500; to 200 mL MilliQ $H_2O$, add 59.6 g material, adjust pH to 7.5, bring to 250 ml total volume with MilliQ $H_2O$, sterile filter (1 M stock solution).
l. TBST Buffer: TBST Buffer: To 900 mL $dH_2O$ add 6.057 g TRIS and 8.766 g NaCl; adjust pH to 7.2 with HCl, add 1.0 mL Triton-X100; bring to 1 L total volume with $dH_2O$.
m. $MnCl_2$: Fischer Cat. #M87-100, make up 1 M stock solution with MilliQ $H_2O$.
n. DTT; Fischer Cat. #BP172-5.
o. TBS (TRIS Buffered Saline): to 900 mL MilliQ $H_2O$ add 6.057 g TRIS and 8.777 g NaCl; bring to 1 L total volume with MilliQ $H_2O$.
p. Kinase Reaction Mixture: Amount per assay plate (100 wells): 1.0 mL Kinase Buffer, 200 $\mu$g GST-$\zeta$, bring to final volume of 8.0 mL with MilliQ $H_2O$.
q. Biotin labeled EEEYEEYEEEYEEEYEEEY: Make peptide stock solution (1 mM, 2.98 mg/ml) in water fresh just before use.
r. Vectastain ELITE ABC reagent: To prepare 14 mL of working reagent, add 1 drop of reagent A to 15 mL TBST and invert tube several times to mix. Then add 1 drop of reagent B. Put tube on orbital shaker at room temperature and mix for 30 minutes.

Procedures
a. Preparation of src coated ELISA plate.
   1. Coat ELISA plate with 0.5 $\mu$g/well anti-src mab in 100 $\mu$L of pH 9.6 sodium carbonate buffer at 4° C. overnight.
   2. Wash wells once with PBS.
   3. Block plate with 0.15 mL 5% milk in PBS for 30 min. at room temperature.
   4. Wash plate 5× with PBS.
   5. Add 10 $\mu$g/well of src transformed yeast lysates diluted in Lysis Buffer (0.1 mL total volume per well). (Amount of lysate may vary between batches.) Shake plate for 20 minutes at room temperature.
b. Preparation of phosphotyrosine antibody-coated ELISA plate.
   1. 4G10 plate: coat 0.5 $\mu$g/well 4G10 in 100 $\mu$L PBS overnight at 4° C. and block with 150 $\mu$L of 5% milk in PBS for 30 minutes at room temperature.
c. Kinase assay procedure.
   1. Remove unbound proteins from step 1–7, above, and wash plates 5× with PBS.
   2. Add 0.08 mL Kinase Reaction Mixture per well (containing 10 $\mu$L of 10×Kinase Buffer and 10 $\mu$M (final concentration) biotin-EEEYEEYEEEYEEEYEEEY per well diluted in water.
   3. Add 10 $\mu$L of compound diluted in water containing 10% DMSO and pre-incubate for 15 minutes at room temperature.
   4. Start kinase reaction by adding 10 $\mu$L/well of 0.05 mM ATP in water (5 $\mu$M ATP final).
   5. Shake ELISA plate for 15 min. at room temperature.
   6. Stop kinase reaction by adding 10 $\mu$L of 0.5 M EDTA per well.
   7. Transfer 90 $\mu$L supernatant to a blocked 4G10 coated ELISA plate from section B, above.
   8. Incubate for 30 min. while shaking at room temperature.
   9. Wash plate 5× with TBST.
   10. Incubate with Vectastain ELITE ABC reagent (100 $\mu$L/well) for 30 min. at room temperature.
   11. Wash the wells 5× with TB ST.
   12. Develop with Turbo TMB.

Example 116
Biochemical lck Assay ELISA
This assay is used to determine lck protein kinase activities measuring phosphorylation of GST-$\zeta$ as the readout.
Materials and Reagents
The following materials and reagents were used:
a. Yeast transformed with lck. Schizosaccharomyces Pombe was used to express recombinant lck (Superti-Furga, et al., *EMBO J*, 12:2625–2634; Superti-Furga, et al., *Nature Biotech.*, 14:600–605). S. Pombe strain SP200 (h-s leu1.32 ura4 ade210) was grown as described and transformations with pRSP expression plasmids were done by the lithium acetate method (Superti-Furga, supra). Cells were grown in the presence of 1 $\mu$M thiamine to induce expression.

b. Cell lysates: Yeast cells expressing lck are pelleted, washed once in water, re-pelleted and stored frozen at −80° C. until use.
c. GST-ζ: DNA encoding for GST-ζ fusion protein for expression in bacteria obtained from Arthur Weiss of the Howard Hughes Medical Institute at the University of California, San Francisco. Transformed bacteria were grown overnight while shaking at 25° C. GST-ζ was purified by glutathione affinity chromatography, Pharmacia, Alameda, Calif.
d. DMSO: Sigma, St. Louis, Mo.
e. 96-Well ELISA plate: Corning 96 Well Easy Wash, Modified Flat Bottom Plate, Corning Cat. #25805-96.
f. NUNC 96-well V-bottom polypropylene plates for dilution of compounds: Applied Scientific Cat. #AS-72092.
g. Purified Rabbit anti-GST antiserum: Amrad Corporation (Australia) Cat. #90001605.
h. Goat anti-Rabbit-IgG-HRP: Amersham Cat. #V010301
i. Sheep ant-mouse IgG (H+L): Jackson Labs Cat. #5215-005-003.
j. Anti-Lck (3A5) mab: Santa Cruz Biotechnology Cat #sc-433.
k. Monoclonal anti-phosphotyrosine UBI-05-321 (UB40 may be used instead).

Buffer Solutions
a. PBS (Dulbecco's Phosphate-Buffered Saline) 1×solution: GIBCO PBS, GIBCO Cat. #450-1300EB.
b. Blocking Buffer: 100 g. BSA, 12.1 g. TRIS-pH7.5, 58.44 g NaCl, 10 mL Tween-20, bring up to 1 L total volume with MilliQ $H_2O$.
c. Carbonate Buffer: $Na_2CO_4$ from Fischer, Cat. #S495; make up 100 mM solution with MilliQ $H_2O$.
d. Kinase Buffer: 1.0 mL (from 1 M stock solution) $MgCl_2$; 0.2 mL (from a 1 M stock solution) $MnCl_2$; 0.2 mL (from a 1 M stock solution) DTT; 5.0 mL (from a 1 M stock solution) HEPES; 0.1 mL TX-100; bring to 10 mL total volume with MilliQ $H_2O$.
e. Lysis Buffer: 5.0 HEPES (from 1 M stock solution.); 2.74 mL NaCl (from 5 M stock solution); 10 mL glycerol; 1.0 mL TX-100; 0.4 mL EDTA (from a 100 mM stock solution); 1.0 mL PMSF (from a 100 mM stock solution); 0.1 mL $Na_3VO_4$ (from a 0.1 M stock solution); bring to 100 mL total volume with MilliQ $H_2O$.
f. ATP: Sigma Cat. #A-7699, make up 10 mM stock solution (5.51 mg/mL).
g TRIS-HCl: Fischer Cat. #BP 152-5, to 600 mL MilliQ $H_2O$ add 121.14 g material, adjust pH to 7.5 with HCl, bring to 1 L total volume with MilliQ $H_2O$.
h. NaCl: Fischer Cat. #S271-10, Make up 5 M stock solution with MilliQ $H_2O$.
i. $Na_3VO_4$: Fischer Cat. #S454-50; to 80 mL MilliQ H20, add 1.8 g material; adjust pH to 10.0 with HCl or NaOH; boil in a microwave; cool; check pH, repeat pH adjustment until pH remains stable after heating/cooling cycle; bring to 100 ml total volume with MilliQ $H_2O$; make 1 ml aliquots and store at −80° C.
j. $MgCl_2$: Fischer Cat. #M33-500, make up 1 M stock solution with MilliQ $H_2O$.
k. HEPES: Fischer Cat. #BP 310-500; to 200 mL MilliQ $H_2O$, add 59.6 g material, adjust pH to 7.5, bring to 250 mL total volume with MilliQ $H_2O$, sterile filter (1 M stock solution).
l. Albumin, Bovine (BSA), Sigma Cat. #A4503; to 150 mL MilliQ $H_2O$ add 30 g material, bring 300 mL total volume with MilliQ $H_2O$, filter through 0.22 μm filter, store at 4° C.
m. TBST Buffer: To 900 mL $dH_2O$ add 6.057 g TRIS and 8.766 g NaCl; adjust pH to 7.2 with HCl, add 1.0 mL Triton-X100; bring to 1 L total volume with $dH_2O$.
n. $MnCl_2$: Fischer Cat. #M87-100, make up 1 M stock solution with MilliQ $H_2O$.
o. DTT; Fischer Cat.#BP172-5.
p. TBS (TRIS Buffered Saline): to 900 mL MilliQ $H_2O$ add 6.057 g TRIS and 8.777 g NaCl; bring to 1 L total volume with MilliQ $H_2O$.
q. Kinase Reaction Mixture: Amount per assay plate (100 wells): 1.0 mL Kinase Buffer, 200 μg GST-4, bring to final volume of 8.0 mL with MilliQ $H_2O$.

Procedures
a. Preparation of Lck coated ELISA plate.
 1. Coat 2.0 μg/well Sheep anti-mouse IgG in 100 μL of pH 9.6 sodium carbonate buffer at 4° C. overnight.
 2. Wash well once with PBS.
 3. Block plate with 0.15 mL of blocking Buffer for 30 min. at room temp.
 4. Wash plate 5× with PBS.
 5. Add 0.5 μg/well of anti-lck (mab-3A5) in 0.1 mL PBS at room temperature for 1–2 hours.
 6. Wash plate 5× with PBS.
 7. Add 20 μg/well of lck transformed yeast lysates diluted in Lysis Buffer (0.1 mL total volume per well). (Amount of lysate may vary between batches) Shake plate at 4° C. overnight to prevent loss of activity.
b. Preparation of phosphotyrosine antibody-coated ELISA plate.
 1. UB40 plate: 1.0 μg/well UB40 in 100 μL of PBS overnight at 4° C. and block with 150 μL of Blocking Buffer for at least 1 hour.
c. Kinase assay procedure.
 1. Remove unbound proteins from step 1–7, above, and wash plates-5× with PBS.
 2. Add 0.08 mL Kinase Reaction Mixture per well (containing 10 μL of 10×Kinase Buffer and 2 μg GST-ζ per well diluted with water).
 3. Add 10 μL of compound diluted in water containing 10% DMSO and pre-incubate for 15 minutes at room temperature.
 4. Start kinase reaction by adding 10 μL/well of 0.1 mM ATP in water (10 μM ATP final).
 5. Shake ELISA plate for 60 min. at room temperature.
 6. Stop kinase reaction by adding 10 μL of 0.5 M EDTA per well.
 7. Transfer 90 μL supernatant to a blocked 4G10 coated ELISA plate from section B, above.
 8. Incubate while shaking for 30 min. at room temperature.
 9. Wash plate 5× with TBST.
 10. Incubate with Rabbit anti-GST antibody at 1:5000 dilution in 100 μL TBST for 30 min. at room temperature.
 11. Wash the wells 5× with TBST.
 12. Incubate with Goat anti-Rabbit-IgG-HRP at 1:20,000 dilution in 100 μL of TBST for 30 min. at room temperature.
 13. Wash the wells 5× with TBST.
 14. Develop with Turbo TMB.

Example 117
ASSAY MEASURING PHOSPHORYLATING FUNCTION OF RAF

The following assay reports the amount of RAF-catalyzed phosphorylation of its target protein MEK as well as MEK's target MAPK. The RAF gene sequence is described in Bonner et al., 1985, *Molec. Cell. Biol.* 5:1400— 1407, and is readily accessible in multiple gene sequence data banks. Construction of the nucleic acid vector and cell lines utilized for this portion of the invention are fully described in Morrison et al., 1988, *Proc. Natl. Acad. Sci. USA* 85: 8855–8859.

Materials and Reagents

1. Sf9 (*Spodoptera frugiperda*) cells; GIBCO-BRL, Gaithersburg, Md.
2. RIPA buffer: 20 mM Tris/HCl pH 7.4, 137 mM NaCl, 10% glycerol, 1 mM PMSF, 5 mg/L Aprotenin, 0.5% Triton X-100;
3. Thioredoxin-MEK fusion protein (T-MEK): T-MEK expression and purification by affinity chromatography were performed according to the manufacturer's procedures. Catalog#K-350-01 and R-350-40, Invitrogen Corp., San Diego, Calif.
4. His-MAPK (ERK-2); His-tagged MAPK was expressed in XL1 Blue cells transformed with pUC18 vector encoding His-MAPK. His-MAPK was purified by Ni-affinity chromatography. Cat#27-4949-01, Pharmacia, Alameda, Calif., as described herein.
5. Sheep anti mouse IgG: Jackson laboratories, West Grove, Pa. Catalog, #515-006-008, Lot#28563
6. RAF-1 protein kinase specific antibody: URP2653 from UBI.
7. Coating buffer: PBS; phosphate buffered saline, GIBCO-BRL, Gaithersburg, Md.
8. Wash buffer: TBST -50 mM Tris/HCL pH 7.2, 150 mM NaCl, 0.1% Triton X-100
9. Block buffer: TBST, 0.1% ethanolamine pH 7.4
10. DMSO, Sigma, St. Louis, Mo.
11. Kinase buffer (KB): 20 mM HEPES/HCl pH 7.2, 150 mM NaCl, 0.1% Triton X-100, 1 mM PMSF, 5 mg/L Aprotenin, 75 mM sodium ortho vanadate, 0.5 MM DTT and 10 mM $MgCl_2$.
12. ATP mix: 100 mM $MgCl_2$, 300 mM ATP, 10 mCi $^{33}P$ ATP (Dupont-NEN)/mL.
13. Stop solution: 1% phosphoric acid; Fisher, Pittsburgh, Pa.
14. Wallac Cellulose Phosphate Filter mats; Wallac, Turku, Finnland.
15. Filter wash solution: 1% phosphoric acid, Fisher, Pittsburgh, Pa.
16. Tomtec plate harvester, Wallac, Turku, Finnland.
17. Wallac beta plate reader #1205, Wallac, Turku, Finnland.
18. NUNC 96-well V bottom polypropylene plates for compounds Applied Scientific Catalog #AS-72092.

Procedure

All of the following steps were conducted at room temperature unless specifically indicated.

1. ELISA plate coating: ELISA wells are coated with 100 mL of Sheep anti mouse affinity purified antiserum (1 mg/100 mL coating buffer) over night at 4° C. ELISA plates can be used for two weeks when stored at 4° C.
2. Invert the plate and remove liquid. Add 100 mL of blocking solution and incubate for 30 min.
3. Remove blocking solution and wash four times with wash buffer. Pat the plate on a paper towel to remove excess liquid.
4. Add 1 mg of antibody specific for RAF-1 to each well and incubate for 1 hour. Wash as described in step 3.
5. Thaw lysates from RAS/RAF infected Sf9 cells and dilute with TBST to 10 mg/100 mL. Add 10 mg of diluted lysate to the wells and incubate for 1 hour. Shake the plate during incubation. Negative controls receive no lysate. Lysates from RAS/RAF infected Sf9 insect cells are prepared after cells are infected with recombinant baculoviruses at a MOI of 5 for each virus, and harvested 48 hours later. The cells are washed once with PBS and lysed in RIPA buffer. Insoluble material is removed by centrifuigation (5 min at 10000×g). Aliquots of lysates are frozen in dry ice/ethanol and stored at −80° C. until use.
6. Remove non-bound material and wash as outlined above (step 3).
7. Add 2 mg of T-MEK and 2 mg of His-MAEPK per well and adjust the volume to 40 mL with kinase buffer. Methods for purifying T-MEK and MAPK from cell extracts are provided herein by example.
8. Pre-dilute compounds (stock solution-10 mg/mL DMSO) or extracts 20 fold in TBST plus 1% DMSO. Add 5 mL of the pre-diluted compounds/extracts to the wells described in step 6. Incubate for 20 min. Controls receive no drug.
9. Start the kinase reaction by addition of 5 mL ATPmix; Shake the plates on an ELISA plate shaker during incubation.
10. Stop the kinase reaction after 60 min by addition of 30 mL stop solution to each well.
11. Place the phosphocellulose mat and the ELISA plate in the Tomtec plate harvester. Harvest and wash the filter with the filter wash solution according to the manufacturers recommendation. Dry the filter mats. Seal the filter mats and place them in the holder. Insert the holder into radioactive detection apparatus and quantify the radioactive phosphorous on the filter mats.

Alternatively, 40 mL aliquots from individual wells of the assay plate can be transferred to the corresponding positions on the phosphocellulose filter mat. After air drying the filters, put the filters in a tray. Gently rock the tray, changing the wash solution at 15 min intervals for 1 hour. Air-dry the filter mats. Seal the filter mats and place them in a holder suitable for measuring the radioactive phosphorous in the samples. Insert the holder into a detection device and quantify the radioactive phosphorous on the filter mats.

Example 118

FLK-1/KDR ASSAY

Example 119

ZAP-70 ASSAY

Materials and Reagents

1. Corning 96-well Elisa plates Corning Catalog #25805-96

2.

| Reagent | Vendor | Catalog # | Order quantity |
|---|---|---|---|
| Poly Glu-Tyr (4:1) | Sigma | P 0275 | 100 mg |

3. PBS (Dulbecco's Phosphate-Buffered Saline) Gibco Catalog #450-1300EB

| Reagent | Molecular Weight | 10 × Stock Concentration | Amt. per L | 1 × Working Concentration |
|---|---|---|---|---|
| KCl | 74.56 | 27 mM | 2.013 g | 2.7 mM |
| $KH_2PO_4$ | 174.18 | 11 mM | 1.916 g | 1.1 mM |
| $MgCl_2 \cdot 6H_2O$ (anhydrous) | 203.31 | 5 mM | 1.017 g | 0.5 mM |
| NaCl | 58.44 | 1.38 M | 80.65 g | 138 mM |
| $Na_2HPO_4$ | 141.96 | 81 mM | 11.50 g | 8.1 mM |

To make 1 liter of 10× stock solution:

1) To a 1 liter graduated cylinder add ~900ml $dH_2O$

2) Add all reagents except the $MgCl_2$

3) When all reagents have dissolved, pH to 7.2 with HCl

4) Add $MgCl_2$

5) Bring volume to 1 liter $dH_2O$

One does not necessarily have to make this buffer up. There are two sources of stock PBS:

1) Sterile GIBCO PBS (1×) in 500 ml bottles found in the media refrigerator (This is the buffer of choice)

2) Sterile 10× and 1× PBS found in the glass cabinets. If this PBS is used the pH must be adjusted to 7.2 with HCl.

To make a 1× working solution from either of the above 10× stocks:

| Reagent | Amount per L |
|---|---|
| 10 × stock | 100 ml |
| $dH_2O$ | 900 ml |

It is advisable to check the pH after diluting the 10× stock.

*Note-PBS can be left at room temperature, but 4° C. is the preferred storage temp.

4. 50 mM HEPES

Dilute Gibco Tissue Culture Grade 1 M HEPES to a final concentration of 50 mM HEPES using MilliQue $H_2O$.

| Reagent | M.W. | 1 ×Working Concentration | Amount per 1 L |
|---|---|---|---|
| 1 M HEPES | | 50 mM | 50 mL |
| MilliQue $H_2O$ | NA | NA | 950 mL |

5. Blocking Buffer

| Reagent | M.W. | 10 × Stock Concentration | Amount per L | 1 ×Working Concentration |
|---|---|---|---|---|
| BSA | NA | 10% | 100 g | 10 g |
| TRIS-pH 7.5 | 121.14 | 100 mM | 12.1 g | 10 mM |
| NaCl | 58.44 | 1 M | 58.44 g | 100 mM |
| Tween-20 | NA | 1% | 10 mL | 0.1% |

6. Purified GST fusion protein containing the Zap70 kinase domain Biochemistry Lab, SUGEN, Inc., −80° C.

Batch #917 p88, concentration 0.18 mg/mL

7. TBS-W Buffer

| Reagent | M.W. | 1 × Working Concentration | Amount per L |
|---|---|---|---|
| Tris | 121.14 | 50 mM | 6.057 g |
| NaCl | 58.44 | 150 mM | 8.766 g |
| Tween-20 | | 0.05% | 0.5 ml |

To make 1 liter of a 1× working solution:

1) To a 1 liter graduated cylinder add ~900 ml $dH_2O$

2) Add all reagents

3) When all reagents have dissolved, pH to 7.6 with HCl

4) Bring volume to 1 liter $dH_2O$

5) Do not keep a 10% stock solution of Tween20. Add 100% Tween20 to the buffer.

A 10× stock solution can be made by multiplying the amounts by 10 (but keeping the final volume of 1 liter). This stock is then diluted 10 fold with $dH_2O$ and re-phed to 7.2.

1× and 10×TBS (pH 7.6) is supplied by the Media Preparation Department.

8. MilliQue $H_2O$+4% DMSO

| Reagent | M.W. | 1 × Working Concentration | Amount per 1 L |
|---|---|---|---|
| MilliQue $H_2O$ | NA | NA | 960 mL |
| DMSO | NA | 4% | 40 ml |

9. 1 mM ATP

| Reagent | Vendor | Catalog # | Order quantity | M.W. | Amount for 5 ml |
|---|---|---|---|---|---|
| Adenosine-5'-triphosphate (from Equine muscle) | Sigma | A-5394 | 5 g | 551.1 | 2.75 mg |
| $dH_2O$ | | | | | 5 ml |

To make 1 mM Stock solution:

1) Add 5 ml of $dH_2O$ to 2.75 mg ATP

2) Vortex

*Note any mg amount of ATP can be used provided it is kept in the same ATP to $dH_2O$ ratio.

*Note this reagent can be stored at −20 in small aliquots to be taken out just prior to use and kept on ice. Do not freeze/thaw aliquots; discard any unused portion.

10. 1 M MnCl$_2$

| Reagent | M.W. | Amount per 100 ml | Stock Concentration |
|---|---|---|---|
| MnCl$_2$ | 197.91 | 19.79 g | 1 M |

12. Reduced Form Glutathione

| Reagent | Vendor | Catalog # | Order quantity | M.W. | Amount for 1 ml | Stock Concentration |
|---|---|---|---|---|---|---|
| Reduced Form Glutathione | Sigma | G-4251 | 25 g | 307.3 | 30.73 | 100 mM |

Not Stable in resuspension. Prepare fresh stock for every experiment!

13. 2×Kinase Dilution Buffer

| Reagent | Stock solution | Amount per 100 ml | Working Concentration |
|---|---|---|---|
| dH$_2$O | NA | 88.4 mL | |
| Hepes pH 7.5 | 1 M | 10 ml | 100 mM |
| BSA/PBS | 5% | 0.4 mL | 0.02% |
| Na-orthovanadate | 0.1 M | 0.2 mL | 0.2 mM |
| NaCl | 5 M | 3 mL | 150 mM |
| Reduced Form Glutathione | 100 mM | 1 mL | 1 mM |

14. 4×ATP Reaction Mixture

| Reagent | Stock solution | Amount per 10 ml | Working Concentration |
|---|---|---|---|
| dH$_2$O | NA | 9.56 mL | |
| MnCl$_2$ | 1 M | 0.4 mL | 40 mM |
| ATP | 0.01 M | 0.008 mL | 0.8 µM |

15. EDTA

| Reagent | M.W. | Stock solution | Amount per 100 ml | Working Solution |
|---|---|---|---|---|
| ethylenediamine-tetraacetic acid | 292.25 | 500 mM | 14.12 g | 500 mM |

To make stock solution:
1) Add 70 ml dH$_2$O to a 250 ml beaker
2) Add EDTA
3) With pH probe in beaker, add 1ON NaOH dropwise EDTA will not dissolve until pH is around 7.0 as EDTA dissolves the pH will fall, add more NaOH
4) When all EDTA is dissolved, adjust the pH to 8.0
5) Transfer to 100 ml graduated cylinder, bring volume to 100 ml with dH$_2$O.

Stock Solution also available from the Media Preparation Department.

16. Antibody Dilution Buffer

| Reagent | Stock solution | Amount per 100 ml | Working Concentration |
|---|---|---|---|
| TBS | | 88 | NA |
| BSA/PBS | 5% | 1 ml | 0.05% |
| Tween-20 | 10% | 1 mL | 0.1% |

17. HRP-Conjuaged Anti-Ptyr

| Reagent | Vendor | Catalog # | Order quantity |
|---|---|---|---|
| HRP-Conjugated Anti-Ptyr (PY99) | Sant Cruz Biotechnology | SC-7020 (lot G219) | 100 µL |

18. Stable ABTS Solution

| Reagent | Vendor | Catalog # | Order quantity |
|---|---|---|---|
| 2,2'-azino-bis(3-ethylbenzthiazoline-6-sulfonic acid) (ABTS) | Moss | ABTS-2000 | 20 L |

19. NUNC 96-well V bottom polypropylene plates Applied Scientific Catalog #AS-72092.

20. 10% SDS (from in House Stock in Common Reagent Room).

Procedure

1. Coat ELISA plates with 2 µg Poly(Glu-Tyr) in 100 µL PBS overnight at 4 degrees (PolyEY stock 10.0 mg/ml in PBS at −80).
2. Wash using the PBSRINSE program of the Titertek Plate Washer. Block plate with 150 µL of TBB for 60 min. The PBS/BLOCK prgram will add blocking buffer after PBS rinse.
3. Wash plate twice with PBS, once with 50 mM Hepes buffer pH 7.4 (use washer program 1 STWASH). Plates can sit in HEPES buffer if other buffers need to be prepared. The Kinase Dilution Buffer, ATP mixture, and TBS-W should all be prepared before proceeding.
4. Add 25 µL drugs (in 4% DMSO) or DMSO controls (4% in water) to plate.

If starting with a 10 mM stock of compound in 100% DMSO, make a 25 fold dilution into water. The concentration of the drug dilution plate will be 400 µM in 4% DMSO. If creating serial dilutions, dilute in 4% DMSO/water down the drug plate. Final compound concentration (highest) in the assay plate will be 100 µM in 1% DMSO 5. Add 50 µl of diluted kinase into all wells. Purified kinase is diluted into "Kinase Dilution Buffer" to achieve a concentration of 5 ng/well. (Concentration of present purified kinase batch is 0.18 mg/mL). For the current batch, add 3.33 µL to 6 mLs of KDB.

Kinase is unstable when diluted. Start kinase reaction as soon after dilution as possible.

6. Add 25 µL of 0.5 M EDTA to the negative controls wells.

7. Add 25 µL ATP/MnCl₂ mixture to entire plate.

The reaction time is 10 minutes and is the most critical part of the assay. The assay must be stopped with 25 µL 0.5 M EDTA in a manner similar to the addition of ATP. Additions of the enzyme, ATP, primary and secondary antibodies can be added with the Titertek Multidrop. The tubing must be flushed with MilliQue H₂O and primed with reagent. Dispensing volumes are accurate to 20 µL.

9. Wash plate 4× with TBS-W (Washer program WASH1).
10. Detect substrate phosphorylation HRP conjugated anti-Ptyr diluted 1:6,000 in Antibody Dilution Buffer. Add 100 µL per well and incubate at room temperature, with shaking, for one hour.
11. Wash plate 3× with TBS-W and 1× with PBS (Washer Program LASTWASH). Residual Tween20 from the washing buffer can inhibit HRP activity and decrease the delta.
12. Add 100 µl of ABTS solution to each well using the Proline Biohit Repeating Pipetor or Titertek Multidrop
15. If necessary, stop the development reaction with the addition of 20 µl 10% SDS per well.
16. Read plate on Dynatech MR7000 elisa reader.

Test Filter: 410 nM
Reference Filter: 630 nM

| Plate template for Placement of Controls | | |
|---|---|---|
| 0 | 1 | 2 |
| OS | | EG |
| OS | | EG |
| OS | | EG |
| OS | | EG |
| EG | | OS |
| EG | | OS |
| EG | | OS |
| EG | | OS |

Cellular/Biologic Assays

Example 120
GENERAL PROCEDURE FOR BRDU INCORPORATION ASSAYS

The following assays use cells engineered to express a receptor of interest and the evaluate the effect of a compound of interest on the activity of ligand-induced DNA synthesis by determining BrdU incorporation into the DNA.

The following materials, reagents, and procedure are general to each of the following BrdU incorporation assays. Variances in specific assays are noted.

Materials and Reagents
1. The appropriate ligand.
2. The appropriate engineered cells.
3. BrdU Labeling Reagent: 10 mM, in PBS (pH7.4) (Boehringer Mannheim, Germany).
4. FixDenat: fixation solution (ready to use) (Boehringer Mannheim, Germany).
5. Anti-BrdU-POD: mouse monoclonal antibody conjugated with peroxidase (Boehringer Mannheim, Germany).
6. TMB Substrate Solution: tetramethylbenzidine (TMB, Boehringer Mannheim, Germany).
7. PBS Washing Solution: 1×PBS, pH 7.4.
8. Albumin, Bovine (BSA), fraction V powder (Sigma Chemical Co., USA).

General Procedure
1. Cells are seeded at 8000 cells/well in 10% CS, 2mM Gln in DMEM, in a 96 well plate. Cells are incubated overnight at 37° C. in 5% CO₂.
2. After 24 hours, the cells are washed with PBS, and then are serum starved in serum free medium (0%CS DMEM with 0.1% BSA) for 24 hours.
3. On day 3, the appropriate ligand and the test compound are added to the cells simultaneously. The negative control wells receive serum free DMEM with 0.1% BSA only; the positive control cells receive the ligand but no test compound. Test compounds are prepared in serum free DMEM with ligand in a 96 well plate, and serially diluted for 7 test concentrations.
4. After 18 hours of ligand activation, diluted BrdU labeling reagent (1:100 in DMEM, 0.1% BSA) is added and the cells are incubated with BrdU (final concentration=10 µM) for 1.5 hours.
5. After incubation with labeling reagent, the medium is removed by decanting and tapping the inverted plate on a paper towel. FixDenat solution is added (50 µL/well) and the plates are incubated at room temperature for 45 minutes on a plate shaker.
6. The FixDenat solution is thoroughly removed by decanting and tapping the inverted plate on a paper towel. Milk is added (5% dehydrated milk in PBS, 200 µL/well) as a blocking solution and the plate is incubated for 30 minutes at room temperature on a plate shaker.
7. The blocking solution is removed by decanting and the wells are washed once with PBS. Anti-BrdU-POD solution (1:200 dilution in PBS, 1% BSA) is added (50 µL/well) and the plate is incubated for 90 minutes at room temperature on a plate shaker.
8. The antibody conjugate is thoroughly removed by decanting and rinsing the wells 5 times with PBS, and the plate is dried by inverting and tapping on a paper towel.
9. TMB substrate solution is added (100 µL/well) and incubated for 20 minutes at room temperature on a plate shaker until color development is sufficient for photometric detection.
10. The absorbance of the samples are measured at 410 nm (in "dual wavelength" mode with a filter reading at 490 nm, as a reference wavelength) on a Dynatech ELISA plate reader.

Example 121
EGF-Induced BrdU Incorporation Assay

The procedure is the same as the general procedure, outlined above, except for the following changes:

Materials and Reagents
1. Mouse EGF, 201 (Toyobo Co., Ltd., Japan).
2. 3T3/EGFRc7.

Example 122
EGF-Induced Her-2-driven BrdU Incorporation Assay

The procedure is the same as the general procedure, outlined above, except for the following changes:

Materials and Reagents
1. Mouse EGF, 201 (Toyobo Co., Ltd., Japan).
2. 3T3/EGFr/Her2/EGFr (EGFr with a Her-2 kinase domain).

Example 123
EGF-Induced Her-4-driven BrdU Incorporation Assay

The procedure is the same as the general procedure, outlined above, except for the following changes:

Materials and Reagents
1. Mouse EGF, 201 (Toyobo Co., Ltd., Japan).
2. 3T3/EGFr/Her4/EGFr (EGFr with a Her-4 kinase domain).

Example 124
PDGF-Induced BrdU Incorporation Assay

The procedure is the same as the general procedure, outlined above, except for the following changes:

Materials and Reagents
1. Human PDGF B/B (Boehringer Mannheim, Germany).
2. 3T3/EGFRc7.

Example 125
FGF-Induced BrdU Incorporation Assay

The procedure is the same as the general procedure, outlined above, except for the following changes:

Materials and Reagents
1. Human FGF2/bFGF (Gibco BRL, USA).
2. 3T3c7/EGFr

Example 126
IGF1-Induced BrdU Incorporation Assay

The procedure is the same as the general procedure, outlined above, except for the following changes:

Materials and Reagents
1. Human, recombinant (G511, Promega Corp., USA)
2. 3T3/IGF1r.

Example 127
Insulin-Induced BrdU Incorporation Assay

The procedure is the same as the general procedure, outlined above, except for the following changes:

Materials and Reagents
1. Insulin, crystalline, bovine, Zinc (13007, Gibco BRL, USA).

Example 128
HGF-Induced BrdU Incorporation Assay

The procedure is the same as the general procedure, outlined above, except for the following changes:

Materials and Reagents
1. Recombinant human HGF (Cat. No. 249-HG, R&D Systems, Inc. USA).
2. BxPC-3 cells (ATCC CRLL-1687).

Procedure
1. Cells are seeded at 9000 cells/well in RPMI 10% FBS in a 96 well plate. Cells are incubated overnight at 37° C. in 5% $CO_2$.
2. After 24 hours, the cells are washed with PBS, and then are serum starved in 100 μl serum-free medium (RPMI with 0.1% BSA) for 24 hours.
3. On day-3, 25 μl containing ligand (prepared at 1 μg/ml in RPMI with 0.1% BSA; final HGF conc.=200 ng/ml) and test compounds are added to the cells. The negative control wells receive 25 μl serum-free RPMI with 0.1% BSA only; the positive control cells receive the ligand (HGF) but no test compound. Test compounds are prepared at 5 times their final concentration in serum-free RPMI with ligand in a 96 well plate, and serially diluted for 7 test concentrations. Typically, the highest final concentration of test compound is 100 μM, and 1:3 dilutions are used (i.e. final test compound concentration range=0.137–100 μM).
4. After 18 hours of ligand activation, 12.5 μl of diluted BrdU labeling reagent (1:100 in RPMI, 0.1% BSA) is added to each well and the cells are incubated with BrdU (final concentration=10 μM) for 1 hour.
5. Same as General Procedure.
6. Same as General Procedure.
7. The blocking solution is removed by decanting and the wells are washed once with PBS. Anti-BrdU-POD solution (1:100 dilution in PBS, 1% BSA) is added (100 μl/well) and the plate is incubated for 90 minutes at room temperature on a plate shaker.
8. Same as General Procedure.
9. Same as General Procedure.
10. Same as General Procedure.

Example 129
HUV-EC-C Assay

The following protocol may also be used to measure a compound's activity against PDGF-R, FGF-R, VEGF, aFGF or Flk-l/KDR, all of which are naturally expressed by HUV-EC cells.

DAY 0
1. Wash and trypsinize HuV-EC-C cells (human umbilical vein endothelial cells, (American Type Culture Collection; catalogue no. 1730 CRL). Wash with Dulbecco's phosphate-buffered saline (D-PBS; obtained from Gibco BRL; catalogue no. 14190-029) 2 times at about 1 mL/10 $cm^2$ of tissue culture flask. Trypsinize with 0.05% trypsin-EDTA in non-enzymatic cell dissociation solution (Sigma Chemical Company; catalogue no. C-1544). The 0.05% trypsin was made by diluting 0.25% trypsin/1 mM EDTA (Gibco; catalogue no. 25200-049) in the cell dissociation solution. Trypsinize with about 1 mL/25–30 $cm^2$ of tissue culture flask for about 5 minutes at 37° C. After cells have detached from the flask, add an equal volume of assay medium and transfer to a 50 mL sterile centrifuge tube (Fisher Scientific; catalogue no. 05-539-6).
2. Wash the cells with about 35 mL assay medium in the 50 mL sterile centrifuge tube by adding the assay medium, centrifuge for 10 minutes at approximately 200 g, aspirate the supernatant, and resuspend with 35 mL D-PBS. Repeat the wash two more times with D-PBS, resuspend the cells in about 1 mL assay medium/15 $cm^2$ of tissue culture flask. Assay medium consists of F12K medium (Gibco BRL; catalogue no. 21127-014)+0.5% heat-inactivated fetal bovine serum. Count the cells with a Coulter Counter Coulter Electronics, Inc.) and add assay medium to the cells to obtain a concentration of 0.8–1.0×$10^5$ cells/mL.
3. Add cells to 96-well flat-bottom plates at 100 μL/well or 0.8–1.0×$10^4$ cells/well; incubate ~24h at 37° C., 5% $CO_2$.

DAY 1
1. Make up two-fold drug titrations in separate 96-well plates, generally 50 μM on down to 0 μM. Use the same assay medium as mentioned in day 0, step 2 above. Titrations are made by adding 90 μL/well of drug at 200 μM (4× the final well concentration) to the top well of a particular plate column. Since the stock drug concentration is usually 20 mM in DMSO, the 200 μM drug concentration contains 2% DMSO.

Therefore, diluent made up to 2% DMSO in assay medium (F12K+0.5% fetal bovine serum) is used as diluent for the drug titrations in order to dilute the drug but keep the DMSO concentration constant. Add this diluent to the remaining wells in the column at 60 µL/well. Take 60 µL from the 120 µL of 200 µM drug dilution in the top well of the column and mix with the 60 µL in the second well of the column. Take 60 µL from this well and mix with the 60 µL in the third well of the column, and so on until two-fold titrations are completed. When the next-to-the-last well is mixed, take 60 µL of the 120 µL in this well and discard it. Leave the last well with 60 µL of DMSO/media diluent as a non-drug-containing control. Make 9 columns of titrated drug, enough for triplicate wells each for 1) VEGF (obtained from Pepro Tech Inc., catalogue no. 100-200, 2) endothelial cell growth factor (ECGF) (also known as acidic fibroblast growth factor, or aFGF) (obtained from Boehringer Mannheim Biochemica, catalogue no. 1439 600); or, 3) human PDGF B/B (1276-956, Boehringer Mannheim, Germany) and assay media control. ECGF comes as a preparation with sodium heparin.

2. Transfer 50 µL/well of the drug dilutions to the 96-well assay plates containing the 0.8–1.0×10$^4$ cells/100 µL/well of the HUV-EC-C cells from day 0 and incubate ~2 h at 37° C., 5% $CO_2$.
3. In triplicate, add 50 µL/well of 80 µg/mL VEGF, 20 ng/mL ECGF, or media control to each drug condition. As with the drugs, the growth factor concentrations are 4× the desired final concentration. Use the assay media from day 0 step 2 to make the concentrations of growth factors. Incubate approximately 24 hours at 37° C., 5% $CO_2$. Each well will have 50 µL drug dilution, 50 µL growth factor or media, and 100 µL cells, =200 µL/well total. Thus the 4× concentrations of drugs and growth factors become 1× once everything has been added to the wells.

DAY 2
1. Add $^3$H-thymidine (Amersham; catalogue no. TRK-686) at 1 µCi/well (10 µL/well of 100 µCi/mL solution made up in RPMI media+10% heat-inactivated fetal bovine serum) and incubate 24 h at 37° C., 5% $CO_2$. Note: $^3$H-thymidine is made up in RPMI media because all of the other applications for which we use the $^3$H-thymidine involve experiments done in RPMI. The media difference at this step is probably not significant. RPMI was obtained from Gibco BRL, catalogue no. 11875-051.

DAY 3
1. Freeze plates overnight at –20° C.

DAY 4
1. Thaw plates and harvest with a 96-well plate harvester (Tomtec Harvester 96®) onto filter mats (Wallac; catalogue no. 1205-401); read counts on a Wallac Betaplate™) liquid scintillation counter.

In vivo Animal Models

Example 130

Xenograft Animal Models

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Poylsen, 1969, *Acta Pathol. Microbial. Scand.* 77:758–760), many different human tumor cell lines (e.g., mammary, lung, genitourinary, gastrointestinal, head and neck, glioblastoma, bone, and malignant melanomas) have been transplanted and successfully grown in nude mice. The following assays may be used to determine the level of activity, specificity and effect of the different compounds of the present invention.

Suitable cell lines for subcutaneous xenograft experiments include C6 cells (glioma, ATCC #CCL 107), A375 cells (melanoma, ATCC #CRL 1619), A431 cells (epidermoid carcinoma, ATCC #CRL 1555), Calu 6 cells (lung, ATCC #HTB 56), PC3 cells (prostate, ATCC #CRL 1435) and NIH 3T3 fibroblasts genetically engineered to overexpress EGFR, PDGFR, IGF-1R or any other test kinase. The following protocol can be used to perform xenograft experiments:

Female athymic mice (BALB/c, nu/nu) are obtained from Simonsen Laboratories (Gilroy, Calif.). All animals are maintained under clean-room conditions in Micro-isolator cages with Alpha-dri bedding. They receive sterile rodent chow and water ad libitum.

Cell lines are grown in appropriate medium (for example, MEM, DMEM, Ham's F10, or Ham's F12 plus 5%–10% fetal bovine serum (FBS) and 2 mM glutamine (GLN)). All cell culture media, glutamine, and fetal bovine serum are purchased from Gibco Life Technologies (Grand Island, N.Y.) unless otherwise specified. All cells are grown in a humid atmosphere of 90–95% air and 5–10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for 10 min. Pellets are resuspended in sterile PBS or media (without FBS) to a particular concentration and the cells are implanted into the hindflank of the mice (8–10 mice per group, 2–10×10$^6$ cells/animal). Tumor growth is measured over 3 to 6 weeks using venier calipers. Tumor volumes are calculated as a product of length x width x height unless otherwise indicated. P values are calculated using the Students t-test. Test compounds in 50–100 µL excipient (e.g., DMSO, or VPD:D5W) are delivered by IP injection at different concentrations generally starting at day one after implantation.

Example 131

Tumor Invasion Model

The following tumor invasion model has been developed and may be used for the evaluation of therapeutic value and efficacy of the compounds identified to selectively inhibit KDR/FLK-1 receptor or CDK2.

Procedure 8 week old nude mice (female) (Simonsen Inc.) were used as experimental animals. Implantation of tumor cells was performed in a laminar flow hood. For anesthesia, Xylazine/ Ketamine Cocktail (100 mg/kg ketamine and 5 mg/kg Xylazine) are administered intraperitoneally. A midline incision is done to expose the abdominal cavity (approximately 1.5 cm in length) to inject 10$^7$ tumor cells in a volume of 100 µL medium. The cells are injected either into the duodenal lobe of the pancreas or under the serosa of the colon. The peritoneum and muscles are closed with a 6-0 silk continuous suture and the skin was closed by using wound clips. Animals were observed daily.

Analysis

After 2–6 weeks, depending on gross observations of the animals, the mice are sacrificed, and the local tumor metastases, to various organs (lung, liver, brain, stomach, spleen, heart, muscle) are excised and analyzed (measurements of tumor size, grade of invasion, immunochemistry, and in situ hybridization).

Example 134
Measurement of Cell Toxicity

Therapeutic compounds should be more potent in inhibiting protein kinase activity than in exerting a cytotoxic effect. A measure of the effectiveness and cell toxicity of a compound can be obtained by determining the therapeutic index: $IC_{50}/LD_{50}$. $IC_{50}$, the dose required to achieve 50% inhibition, can be measured using standard techniques such as those described herein. $LD_{50}$, the dosage which results in 50% toxicity, can also be measured by standard techniques (Mossman, 1983, *J. Immunol. Methods*, 65:55–63), by measuring the amount of LDH released (Korzeniewski and Callewaert, 1983, *J. Immunol. Methods*, 64:313; Decker and Lohmann-Matthes, 1988, *J. Immunol. Methods*, 115:61), or by measuring the lethal dose in animal models. Compounds with a large therapeutic index are preferred. The therapeutic index should be greater than 2, preferably at least 10, more preferably at least 50.

Example 135
The Activity of the Compounds of the Invention

The biological or biochemical activity of some of the compounds of the invention were tested using the assays described above. The $IC_{50}$ values were measured for several of the compounds of the invention. The results are shown in Table 10 below.

TABLE 10

| Compound No. | bio flkGST $IC_{50}$ ($\mu$M) | bio EGF $IC_{50}$ ($\mu$M) | bio PDGF $IC_{50}$ ($\mu$M) |
| --- | --- | --- | --- |
| IN-001 | 0.86 | >100 | 0.11 |
| IN-002 | 0.03 | 2.87 | 0.38 |
| IN-003 | 1.56 | 61.29 | |
| IN-004 | 0.47 | 2.57 | 21 |
| IN-005 | 0.31 | 16.27 | |
| IN-006 | 0.16 | 4.69 | 1.45 |
| IN-007 | 0.4 | 37.37 | <0.78 |
| IN-008 | 0.22 | 1.97 | 0.29 |
| IN-009 | 9.42 | >100 | <0.78 |
| IN-010 | 0.35 | 88.8 | <0.78 |
| IN-011 | 0.52 | 1.36 | <0.78 |
| IN-012 | 1.95 | >100 | <0.78 |
| IN-013 | 0.1 | 41.26 | 0.008 |
| IN-014 | 0.003 | 43.47 | 0.15 |
| IN-015 | 0.99 | 70.62 | 0 |
| IN-016 | 0.05 | >10 | 0.028 |
| IN-017 | 0.01 | 4.67 | 0.07 |
| IN-018 | 5.41 | >100 | <0.78 |
| IN-019 | 0.16 | 9.55 | 5.65 |
| IN-022 | 0.14 | >20 | |
| IN-023 | 0.24 | >20 | |
| IN-024 | <0.01 | >20 | |
| IN-025 | 0.14 | >20 | |
| IN-026 | 0.76 | >20 | |
| IN-027 | 2.01 | >20 | |
| IN-028 | 0.66 | 6.06 | |
| IN-029 | 0.76 | >20 | |
| IN-030 | <0.009 | >20 | |
| IN-031 | 0.53 | >20 | |
| IN-032 | 1.47 | >20 | |
| IN-033 | <0.009 | 8.2 | |
| IN-034 | 13.98 | >20 | |
| IN-035 | >20 | >20 | |
| IN-036 | >20 | >20 | |
| IN-037 | 4.38 | >20 | |
| IN-038 | >10 | >20 | |
| IN-039 | 0.17 | >100 | 0.91 |
| IN-040 | 0.21 | >100 | 9.3 |
| IN-041 | 0.21 | 8.43 | |
| IN-042 | 1.34 | 7.84 | |
| IN-043 | 0.27 | 4.35 | |
| IN-044 | 0.18 | 1.69 | |
| IN-045 | 0.12 | 8.02 | |
| IN-046 | 1.05 | 1.23 | |
| IN-047 | 0.39 | 0.87 | |
| IN-048 | 1.16 | 2.13 | |
| IN-049 | 0.13 | 4.38 | |
| IN-050 | 0.71 | 2.4 | |
| IN-051 | 0.37 | 3.52 | |
| IN-052 | 1.02 | 1.16 | |
| IN-053 | 1.21 | 15.2 | |
| IN-054 | 4.28 | >20 | |
| IN-055 | 1.5 | 3.5 | |
| IN-056 | 9.96 | 15.53 | |
| IN-057 | >20 | >20 | |
| IN-058 | 8.49 | >20 | |
| IN-059 | 0.63 | >20 | |
| IN-060 | 8.55 | >20 | |
| IN-061 | 0.39 | 4.46 | |
| IN-062 | 15.38 | >20 | |
| IN-063 | 14.33 | >20 | |
| IN-064 | 17.82 | >20 | |
| IN-065 | 11.67 | | 89.41 |
| IN-066 | >20 | >100 | >100 |
| IN-067 | 3.99 | >100 | >100 |
| IN-068 | >20 | >100 | >100 |
| IN-069 | 12.77 | >100 | >100 |
| IN-070 | 2.33 | >100 | 79.22 |
| IN-071 | 11.47 | 22.04 | 69.14 |
| IN-072 | >20 | >100 | >100 |
| IN-073 | >20 | >100 | >100 |
| IN-074 | 1.58 | >100 | >100 |
| IN-075 | 6.51 | >100 | >100 |

CONCLUSION

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

What is claimed is:

1. An indolinone compound having a structure set forth in formula (II):

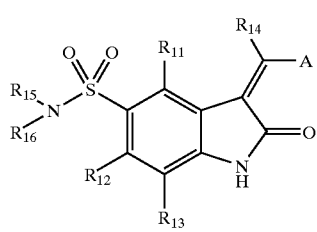

(II)

wherein:

(a) $R_{11}$–$R_{14}$ are hydrogen;

(b) $R_{15}$ and $R_{16}$ are each independently selected from the group consisting of hydrogen, optionally substituted alkyl, optionally substituted aryl, or $R_{15}$ and $R_{16}$ taken together with the nitrogen atom to which they are attached form a ring structure selected from the group consisting of a five-membered or six-membered heteroaromatic ring, a five-membered or six-membered heteroaliphatic ring, a nine-membered fused bicyclic heteroaromatic ring, and a ten-membered fused bicyclic heteroaromatic ring; and (c) A is selected from the group consisting of formula (III), (IV), and (V):

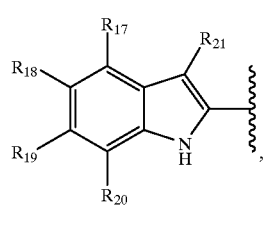

(III)

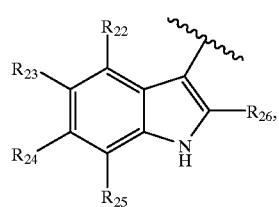

(IV)

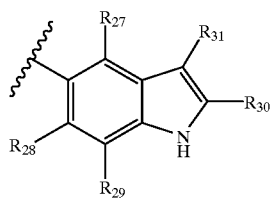

(V)

wherein:

(i) $R_{19}$–$R_{25}$ and $R_{27}$–$R_{31}$ are hydrogen;

(ii) $R_{17}$ and $R_{18}$ are each independently selected from the group consisting of hydrogen, optionally substituted alkyl, and optionally substituted alkoxy provided that both $R_{17}$ and $R_{18}$ are not hydrogen; and (iii) $R_{26}$ is selected from the group consisting of optionally substituted alkyl; or a pharmaceutically acceptable salt thereof.

2. The compound of claim 1, wherein:

(i) $R_{15}$ is hydrogen or alkyl;

(ii) $R_{16}$ is hydrogen, alkyl, phenyl, wherein said phenyl group is optionally substituted with one or two substituents selected from halo or unsubstituted lower alkyl; or $R_{15}$ and $R_{16}$ together with the nitrogen to which they are attached form 2,3-dihydroindol-1-yl, 2,3-dihydro-2H-quinolin-1-yl, or 2,3-dihydro-2H-isoisoquinolin-2-yl ring wherein said rings are optionally substituted with halo or alkyl;

(iii) $R_{17}$ is hydrogen, methyl, or methoxy;

(iv) $R_{18}$ is selected from the group consisting of lower alkoxy substituted with heteroalicyclic; and (v) A is group of formula III.

3. The compound of claim 1, wherein:

(i) $R_{15}$ is hydrogen or methyl;

(ii) $R_{16}$ is hydrogen, methyl, isopropyl, phenyl, 3-chlorophenyl, or 4-chloro-2-fluorophenyl, or $R_{15}$ and $R_{16}$ together with the nitrogen atom to which they are attached form 2,3-dihydroindol-1-yl, 2,3-dihydro-2H-quinolin-1-yl, 5-bromo-2,3-dihydro-2H-quinolin-1-yl, or 2,3-dihydro-2H-isoquinolin-2-yl;

(iii) $R_{17}$ is selected from the group consisting of hydrogen, methyl, and methoxy; and (iv) $R_{18}$ is selected from the group consisting of hydrogen, 2-pyrrolidin-1-yl-ethoxy and 2-morpholin-4-yl-ethoxy.

4. The compound of claim 1, wherein:

(i) $R_{15}$ is hydrogen or alkyl;

(ii) $R_{16}$ is hydrogen, alkyl, phenyl optionally substituted with one or two substituents selected from halo or unsubstituted lower alkyl; or (iii) $R_{15}$ and $R_{16}$ together with the nitrogen to which they are attached form 2,3-dihydroindol-1-yl, 2,3-dihydro-2H-quinolin-1-yl, or 2,3-dihydro-2H-isoisoquinolin-2-yl ring wherein said rings are optionally substituted with halo or alkyl;

(iv) $R_{20}$ is selected from the group consisting of optionally substituted alkyl; and (v) A is group of formula IV.

5. The compound of claim 1, wherein:

(i) $R_{15}$ is hydrogen or methyl;

(ii) $R_{16}$ is hydrogen, methyl, isopropyl, phenyl, 3-chlorophenyl, or 4-chloro-2-fluorophenyl, or $R_{15}$ and $R_{16}$ together with the nitrogen atom to which they are attached form 2,3-dihydroindol-1-yl, 2,3-dihydro-2H-quinolin-1-yl, 5-bromo-2,3-dihydro-2H-quinolin-1-yl, or 2,3-dihydro-2H-isoisoquinolin-2-yl; and (iii) $R_{26}$ is methyl.

6. The compound of claim 1, wherein:

(i) $R_{15}$ is hydrogen or alkyl;

(ii) $R_{16}$ is hydrogen, alkyl, phenyl optionally substituted with one or two substituents selected from halo or unsubstituted lower alkyl; or $R_{15}$ and $R_{16}$ together with the nitrogen to which they are attached form 2,3-dihydroindol-1-yl, 2,3-dihydro-2H-quinolin-1-yl, or 2,3-dihydro-2H-isoisoquinolin-2-yl ring wherein said rings are optionally substituted with halo or alkyl; and (iii) A is group of formula V.

7. The compound of claim 1, wherein:

(i) $R_{15}$ is hydrogen or methyl; and (ii) $R_{16}$ is hydrogen, methyl, isopropyl, phenyl, 3-chlorophenyl, or 4-chloro-2-fluorophenyl, or $R_{15}$ and $R_{16}$ together with the nitrogen atom to which they are attached form 2,3-dihydroindol-1-yl, 2,3-dihydro-2H-quinolin-1-yl, 5-bromo-2,3-dihydro-2H-quinolin-1-yl, or 2,3-dihydro-2H-isoisoquinolin-2-yl; and (iii) A is group of formula V.

8. A compound selected from the group consisting of:

2-oxo-3-[5-(2-pyrrolidin-1-yl-ethoxy)-1H-indol-2-ylmethylene]-2,3-dihydro-1H-indole-5-sulfonic acid amide, 3-[5-(2-morpholin-4-yl-ethoxy)-1H-indol-2-ylmethylene]-2-oxo-2,3-dihydro-1H-indole-5-sulfonic acid amide, 2-oxo-3-[5-(2-pyrrolidin-1-yl-ethoxy)-1H-indol-2-ylmethylene]-2,3-dihydro-1H-indole-5-sulfonic acid methylamide, 2-oxo-3-[5-(2-pyrrolidin-1-yl-ethoxy)-1H-indol-2-ylmethylene]-2,3-dihydro-1H-indole-5-sulfonic acid dimethylamide, 2-oxo-3-[5-(2-pyrrolidin-1-yl-ethoxy)-1H-indol-2-ylmethylene]-2,3-dihydro-1H-indole-5-sulfonic acid isopropylamide, 2-oxo-3-[5-(2-pyrrolidin-1-yl-ethoxy)-1H-indol-2-ylmethylene]-2,3-dihydro-1H-indole-5-sulfonic acid phenylamide, 5-(2,3-dihydro-indole-1-sulfonyl)-3-[5-(2-pyrrolidin-1-yl-ethoxy)-1H-indol-2-ylmethylene]-1,3-dihydro-indol-2-one, 2-oxo-3-[5-(2-pyrrolidin-1-yl-ethoxy)-1H-indol-2-ylmethylene]-2,3-dihydro-1H-indole-5-solfonic acid (3-cloro-phenyl)-amide, 2-oxo-3-[5-(2-pyrrolidin-1-yl-ethoxy)-1H-indol-2-ylmethylene]-2,3-dihydro-1H-indole-5-solfonic acid (3-cloro-phenyl)-methyl-amide, 2-oxo-3-[5-(2-pyrrolidin-1-yl-ethoxy)-1H-indol-2-ylmethylene]-2,3-dihydro-1H-indole-5-solfonic acid (4-cloro-2-flouro-phenyl)-methyl-amide, 5-(3,4-dihydro-2H-quinoline-1-sulfonyl)-3-[5-(2-pyrrolidin-1-yl-ethoxy)-1H-indol-2-ylmethylene]-1,3-dihydro-indol-2-one, 5-(3,4-dihydro-1H-isoquinoline-2-sulfonyl)-3-[5-(2-pyrrolidin-1-yl-ethoxy)-1H-indol-2-ylmethylene]-1,3-dihydro-indol-2-one, 5-(5-bromo-2,3-dihydro-indole-1-sulfonyl)-3-[5-(2-pyrrolidin-1-yl-ethoxy)-1H-indol-2-ylmethylene]-1,3-dihydro-indol-2-one, 3-[5-(2-morpholin-4-yl-ethoxy)-1H-indol-2-ylmethylene]-2-oxo-2,3-dihydro-1H-indol-5-sulfonic acid methylamide, 3-[5-(2-morpholin-4-yl-ethoxy)-1H-indol-2-ylmethylene]-2-oxo-2,3-dihydro-1H-indol-5-sulfonic acid methylamide, 3-[5-(2-morpholin-4-yl-ethoxy)-1H-indol-2-ylmethylene]-2-oxo-2,3-dihydro-1H-indol-5-sulfonic acid isopropylamide, 3-[5-(2-morpholin-4-yl-ethoxy)-1H-indol-2-ylmethylene]-2-oxo-2,3-dihydro-1H-indol-5-sulfonic acid phenylamide, 5-(2,3-dihydro-indole-1-sulfonyl)-3-[5-(2-morpholin-4-yl-ethoxy)-1H-indol-2-ylmethylene]-1,3-dihydro-indol-2-one, 3-[5-(2-morpholin-4-yl-ethoxy)-1H-indol-2-ylmethylene]-2-oxo-2,3-dihydro-1H-indole-5-sulfonic acid (3-cloro-phenyl)-amide, 3-[5-(2-morpholin-4-yl-ethoxy)-1H-indol-2-ylmethylene]-2-oxo-2,3-dihydro-1H-indole-5-sulfonic acid (3-cloro-phenyl)-methyl-amide, 3-[5-(2-morpholin-4-yl-ethoxy)-1H-indol-2-ylmethylene]-2-oxo-2,3-dihydro-1H-indole-5-sulfonic acid (4-cloro-2-flouro-phenyl)-amide, 5-(3,4-dihydro-2H-quinoline-1-sulfonyl)-3-[5-(2-morpholin-4-yl-ethoxy)-1H-indol-2-ylmethylene]-1,3-dihydro-indol-2-one, 5-(3,4-dihydro-1H-isoquinoline-2-sulfonyl)-3-[5-(2-morpholin-4-yl-ethoxy)-1H-indol-2-ylmethylene]-1,3-dihydro-indol-2-one, 5-(5-bromo-2,3-dihydro-indole-1-sulfonyl)-3-[5-(2-morpholin-4-yl-ethoxy)-1H-indol-2-ylmethylene]-1,3-dihydro-indol-2-one, 3-(1H-indol-3-ylmethylene)-2-oxo-2,3-dihydro-1H-indole-5-sulfonic acid amide, 3-(2-methyl-1H-indol-3-ylmethylene)-2-oxo-2,3-dihydro-1H-indole-5-sulfonic acid amide, 3-(1H-indol-5-ylmethylene)-2-oxo-2,3-dihydro-1H-indole-5-sulfonic acid amide, 3-(1H-indol-3-ylmethylene)-2-oxo-2,3-dihydro-1H-indole-5-sulfonic acid methylamide, 3-(2-methyl-1H-indol-3-ylmethylene)-2-oxo-2,3-dihydro-1H-indole-5-sulfonic acid methylamide, 3-(1H-indol-5-ylmethylene)-2-oxo-2,3-dihydro-1H-indole-5-sulfonic acid methylamide, 3-(1H-indol-2-ylmethylene)-2-oxo-2,3-dihydro-1H-indole-5-sulfonic acid methylamide, 3-(1H-indol-3-ylmethylene)-2-oxo-2,3-dihydro-1H-indole-5-sulfonic acid dimethylamide, 3-(2-methyl-1H-indol-3-ylmethylene)-2-oxo-2,3-dihydro-1H-indole-5-sulfonic acid dimethylamide, 3-(1H-indol-5-ylmethylene)-2-oxo-2,3-dihydro-1H-indole-5-sulfonic acid dimethylamide, 3-(1H-indol-2-ylmethylene)-2-oxo-2,3-dihydro-1H-indole-5-sulfonic acid dimethylamide, and 3-(4-methoxy-1H-indol-2-ylmethylene)-2-oxo-2,3-dihydro-1H-indole-5-sulfonic acid methylamide;

or a pharmaceutically acceptable salt thereof.

* * * * *